US009060997B2

(12) United States Patent
Rodriguez-Lopez et al.

(10) Patent No.: US 9,060,997 B2
(45) Date of Patent: Jun. 23, 2015

(54) ANTIFOLATE COMPOUNDS FOR THE TREATMENT OF MELANOMA

(75) Inventors: Jose Neptuno Rodriguez-Lopez, Murcia (ES); Luis Sanchez Del Campo Ferrer, Murcia (ES); Juan Cabezas-Herrera, Murcia (ES); Alberto Tarraga Tomas, Murcia (ES); Magali Maria Saez Ayala, Murica (ES)

(73) Assignee: UNIVERSIDAD DE MURCIA, Murcia (ES)

( * ) Notice: Subject to any disclaimer, the term of this patent is extended or adjusted under 35 U.S.C. 154(b) by 946 days.

(21) Appl. No.: 12/809,713

(22) PCT Filed: Dec. 18, 2008

(86) PCT No.: PCT/IB2008/003727
§ 371 (c)(1),
(2), (4) Date: Jun. 21, 2010

(87) PCT Pub. No.: WO2009/081275
PCT Pub. Date: Jul. 2, 2009

(65) Prior Publication Data
US 2010/0279971 A1 Nov. 4, 2010

(30) Foreign Application Priority Data

Dec. 21, 2007 (GB) .................................. 0725077.2

(51) Int. Cl.
*A01N 43/16* (2006.01)
*A61K 31/35* (2006.01)
*A61K 31/353* (2006.01)

(52) U.S. Cl.
CPC .................................... *A61K 31/353* (2013.01)

(58) Field of Classification Search
None
See application file for complete search history.

(56) References Cited

U.S. PATENT DOCUMENTS

| 5,804,567 | A | 9/1998 | Cheng et al. | |
|---|---|---|---|---|
| 7,041,699 | B2 * | 5/2006 | Netke et al. | 514/456 |
| 2005/0027000 | A1 | 2/2005 | Reed et al. | |

OTHER PUBLICATIONS

Fan et al. Bioorganic & Medicinal Chemistry Letters, vol. 7, No. 24, pp. 3107-3112.*
Waleh et al. "Novel D-ring Analog of Epigallocatechin-3-gallate Inhibits Tumor Growth and VEGF Expression in Breast Carcinoma Cells", AnticancerRes., 2005, vol. 25, pp. 397-402.*
Detich et al. "The Methyl Donor S-Adenosylmethionine Inhibits Active Demethylation of DNA", J.Biol.Chem., 2003, vol. 278, No. 23, pp. 20812-20820.*
Lavis, "Ester Bonds in Prodrugs", ACS Chem.Biol., 2008, vol. 3, No. 4, pp. 203-206.*
Rautio et al., "Prodrugs: design and clinical applications", Nat. Rev. Drug Disc., 2008, vol. 7, pp. 255-270.*
Fan et al. Bioorganic & Medicinal Chemistry Letters, 1997, vol. 7, No. 24, pp. 3107-3112.*
Saez-Ayala, M. et al., Comparison of a Pair of Synthetic Tea-Catechin-Derived Epimers: Synthesis, Antifolate Activity, and Tyrosinase-Mediated Activation in Melanoma, DOI: 10.1002/cmdc. 201000482, ChemMedChem 2011, 6, 440-449 (Exhibit A).
Waleh, Nahid S., et al., Novel D-ring Analog of Epigallocatechin-3-gallate Inhibits Tumor Growth and VEGF Expression in Breast Carcinoma Cells, Anticancer Research 25: 397-402 (2005) (Exhibit B).
Liu et al., "Inhibition of Melanoma Growth and Metastasis by Combination With (−)-Epigalocatechin-3-Gallate and Dacarbazine in Mice," Journal of Cellular Biochemistry 83:631-642 (2001).

(Continued)

*Primary Examiner* — Jeffrey S Lundgren
*Assistant Examiner* — Stephanie Springer
(74) *Attorney, Agent, or Firm* — Vedder Price P.C.; Thomas J. Kowalski; Deborah L. Lu

(57) ABSTRACT

This invention relates to compounds of the formula X) or Xl) (X) (XI) wherein: each —$R^1$, —$R^2$ and —$R^3$ is independently -$Q^1$, —OH or —H, where at least one of —$R^1$, —$R^2$ and —$R^3$ is not —H or —OH; each —$R^4$ and —$R^5$ is independently -$Q^2$ or —H; each -$Q^1$ is independently selected from: —F, —Cl, —$R^A$, —$OR^A$, —SH, —$SR^A$, where each —$R^A$ is independently selected from methyl and ethyl, which may substituted by one or more fluoro or chloro groups; and each -$Q^2$ is selected from: —F, —Cl, —$R^B$, —$OR^B$, —SH, —$SR^B$, where each —$R^B$ is independently selected from methyl and ethyl, which may substituted by one or more fluoro or chloro groups; which are useful in the treatment of melanoma.

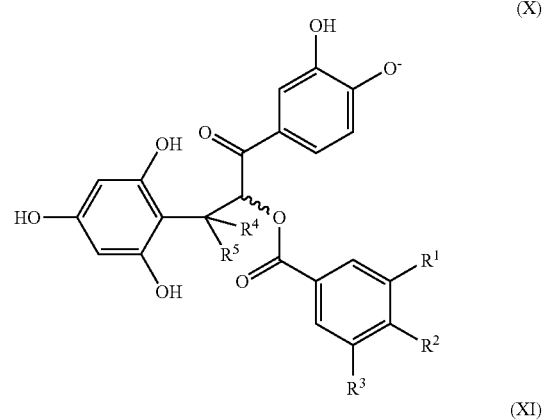

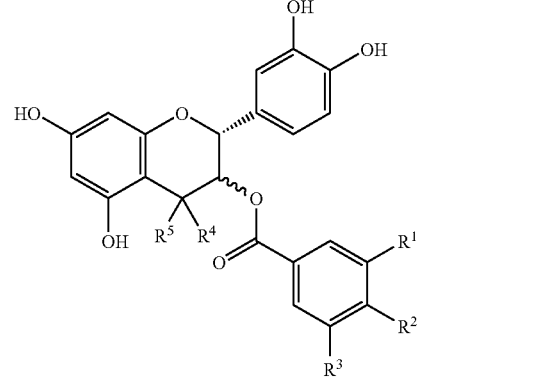

11 Claims, 26 Drawing Sheets

(56) References Cited

OTHER PUBLICATIONS

Ogata et al., "Effects of Catechins on the Mouse Tumor Cell Adhesion to Fibronectin," Planta Med., 61:472-474 (1995).

Park et al., "Anticancer activity of 3-O-acyl and alkyl-(−)-epicatechin derivatives," Bioorganic & Medicinal Chemistry Letters, 14:5189-5192 (2004).

Sanchez-del-Campo et al., Synthesis and Biological Activity of a 3,4,5-Trimethoxybenzoyl Ester Analogue of Epicatechin-3-gallate, J. Med. Chem., 51:2018-2026 (2008).

Sanchez-del-Campo et al., Targeting the methionine cycle for melanoma therapy with 3-O—(3,4,5-trimethoxybenzoyl)-(−)-epicatechin, Int. J. Cancer, 123:2446-2455 (2008).

Suzuki et al., "Inhibitory effect of epigallocatechin gallate on adhesion of murine melanoma cells to laminin," Cancer Letters, 173:15-20 (2001).

International Search Report and Written Opinion from priority PCT application No. PCT/IB2008/003727, 2009.

* cited by examiner

ANTIFOLATE COMPOUNDS FOR THE TREATMENT OF MELANOMA

RELATED APPLICATIONS

This application is the U.S. National Stage of International Application No. PCT/IB2008/003727, filed Dec. 18, 2008, published in English, and claims the benefit of GB Application Number 0725077.2, filed Dec. 21, 2007, the entire teachings of these applications are incorporated herein by reference.

FIELD OF INVENTION

This invention relates to anti-folate compounds for use in the treatment of melanoma.

BACKGROUND OF INVENTION

Melanoma, a malignant neoplasm of melanocytes, is the most deadly form of skin cancer (Chudnovsky et al., 2005). The incidence of melanoma continues to increase despite public health initiatives to promote protection against sun's harmful effects. In Europe, approximately 26,100 males and 33,300 females are diagnosed each year with melanoma, and around 8,300 males and 7,600 females die of it. It is the eighth most commonly diagnosed cancer in females and seventeenth in males. Light skin type, large numbers of nevi and excessive sun exposure, mainly in childhood, are the major modifiers of melanoma risk (Houghon and Polsky, 2002). When melanoma is detected in its early stages it is curable, but once advanced it is very difficult to treat. The primary lesions are located in limbs (22%), trunk (40%), head and neck (15%), and 16% in unknown sites (Capizzi and Donohue, 1994). The most common sites of metastases found in the autopsy are skin and subcutaneous tissue (75%), lung (70%), liver (68%), small intestine (58%), pancreas (53%), heart (49%), brain (39%) and spleen (36%). With visceral metastasis, the 5-year survival drops to approximately 6%, and the median survival from time of diagnosis is 7.5 months (Barth et al., 1995).

The increasing incidence of melanoma and its poor prognosis in advanced stages justify the investigation into novel approaches of prevention, such as chemoprevention, which has been used to reduce the incidence of other cancers. Ideally, medications would be inexpensive, easily administered, and have minimal side effects. Such agents would be especially valuable for high risk patients. In the evaluation of effectiveness, chemoprevention interventions would best be measured by their ability to reduce melanoma incidence and melanoma mortality. Investigation into a possible role in melanoma chemoprevention continues for multiple agents, including sunscreen, lipid-lowering medications, non-steroidal anti-inflammatory drugs, dietary nutrients, immunomodulators, and other drugs, including retinoids, difluoromethylornithine, and T4 endonuclease V (Francis et al., 2006). Although chemoprevention is the ideal strategy, primary melanoma, once formed, should be surgically removed and chemotherapy focuses in metastasis control. At present, limited therapeutic options exist for patients with metastatic melanoma, and all standard combinations used in metastasis therapy have a low efficacy and poor response rates (Koon and Atkins, 2006).

One example of the complications involved in melanoma chemotherapy is the limited use of antifolates. Although methotrexate (MTX), the most frequently used antifolate, is an efficient drug for several types of cancer it is not active against melanoma (Kufe et al. 1980). It is, therefore, of great interest to develop a second generation of antifolate drugs to overcome, these problems and which should present low toxicity for the prophylaxis and treatment of melanoma.

SUMMARY OF INVENTION

The present inventors have produced derivatives of epicatechin-3-gallate and catechin-3-galate which display unexpectedly high anti-proliferative activity against melanoma and other cancers. The derivatives may have the structure of formula (X) or of formula (XI) as described herein.

Aspects of the invention provide methods of treatment of melanoma which comprise administering to an individual in need thereof a therapeutically effective amount of the compound of formula (X) or formula (XI).

In some embodiments, a cytoxic folate receptor alpha (FRα) ligand and/or a methionine cycle inhibitor such as s-adenosylmethionine, adenosine or dipyridamole, may be administered to the individual in combination with the compound of formula (X) or formula (XI).

Other aspects of the invention provide methods of synthesising the compound of formula (X) or formula (XI).

In some embodiments, the compound of formula (XI) is 3,4,5-trimethoxy-epicatechin-3-gallate.

BRIEF DESCRIPTION OF DRAWINGS

FIG. 9A shows spectrophotometric recordings for the oxidation of TMECG (200 µM) in the presence of human tyrosinase (0.5 µg/mL) at pH 5.5. The arrow represents the absorbance direction and the time between recordings was 1 min. FIG. 9B shows a plot of TMECG concentration versus human tyrosinase (0.5 µg/mL) initial rate at pH 5.5. Data was fitted to the Michaelis-Menten equation using non-lineal regression analysis. FIG. 9C shows a representation of the absorbance at 470 nm vs pH. FIG. 9D shows visible absorption spectra of the QM product at pH 5.5 (continuous line) and 8.0 (dashed line). FIG. 9E shows reactions sequence indicating the oxidation of TMECG by tyrosinase and the formation of quinone methide species.

DETAILED DESCRIPTION OF EMBODIMENTS OF THE INVENTION

Figure 1:
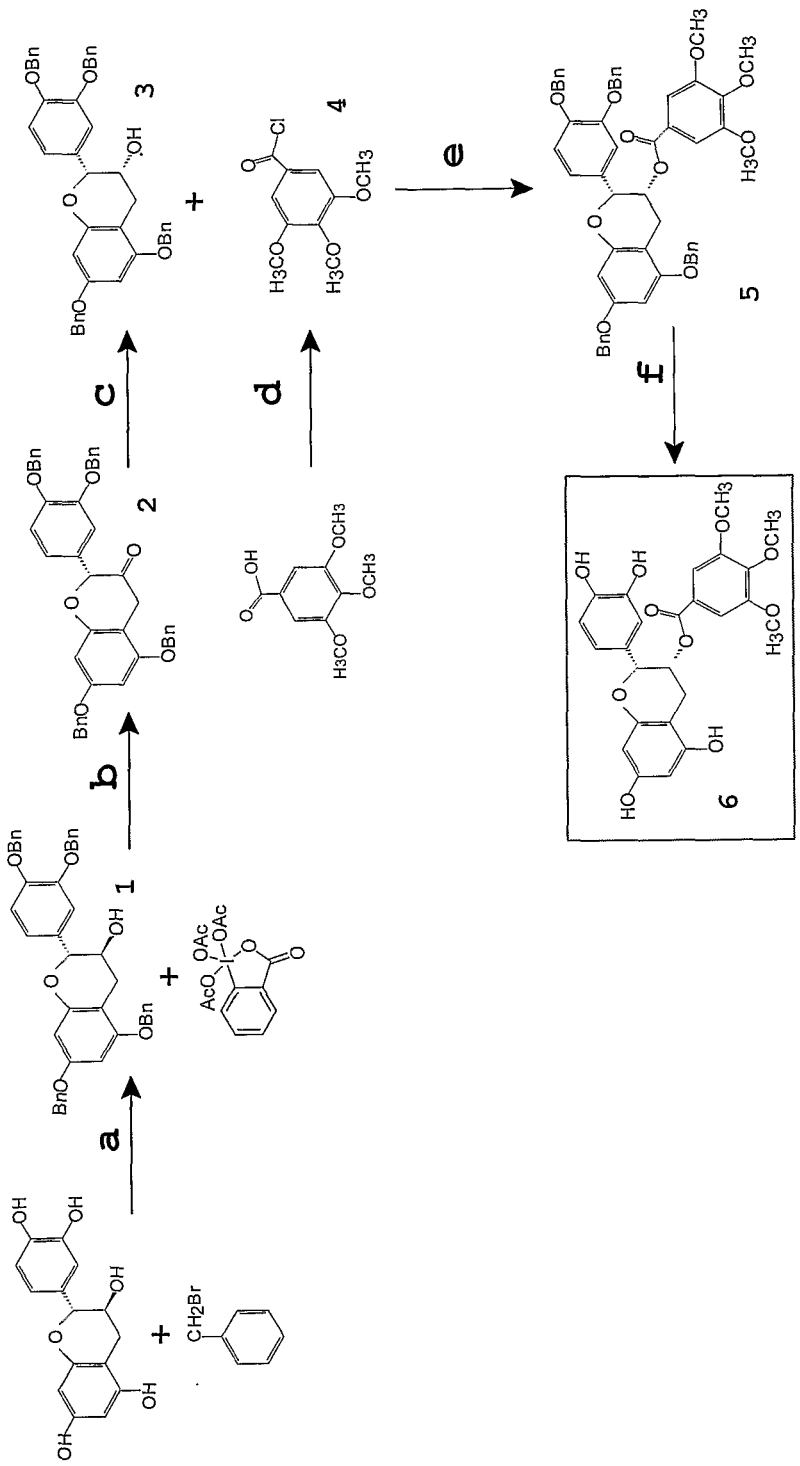
FIG. 1 shows the reaction scheme for the synthesis of 3,4,5-trimethoxy-epicatechin-3-gallate. Reaction conditions were as follows; a: BnBr, $K_2CO_3$, DMF, $-15°$ C. to rt. b: Dess-Martin periodinane, moist $CH_2Cl_2$, rt. c: L-Selectride®, n-$Bu_4$NCl, THF, $-78°$ C. d: 3,4,5-Trimethoxybenzoic acid, $PCl_5$, $C_7H_8$, reflux, e: 3,4,5-trimethoxybenzoyl chloride, $CH_2Cl_2$, DMAP, $-15°$ C. to rt. f: $H_2$, 20% Pd(OH)$_2$/C, THF/MeOH, rt.

An aspect of the invention provides a method of treating melanoma or other cancer comprising administering to an individual in need thereof a therapeutically effective amount of a compound of formula (X) or a compound of formula (XI).

Related aspects provide a compound of formula (X) or a compound of formula (XI) for use in the treatment of melanoma or other cancer, and the use of a compound of formula (X) or a compound of formula (XI) in the manufacture of a medicament for use in the treatment of melanoma or other cancer.

In some embodiments, the compound of formula (XI) is 3,4,5-trimethoxy-epicatechin-3-gallate.

3,4,5-trimethoxy-epicatechin-3-gallate has the formula (I) below. The atom numbering is shown.

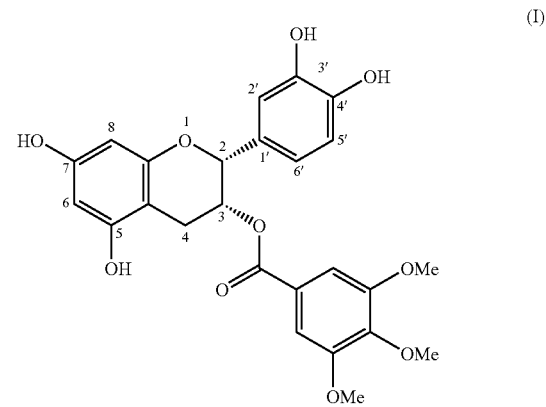 [SMILES: COc1cc(C(=O)O[C@@H]2Cc3c(O)cc(O)cc3O[C@@H]2c2ccc(O)c(O)c2)cc(OC)c1OC]

(I)

The results set out herein show that 3,4,5-trimethoxy-epicatechin-3-gallate is activated within melanoma cells to a quinone methide (QM) metabolite having a deprotonated form at neutral pH which is shown in formulae (II) and (III) below.

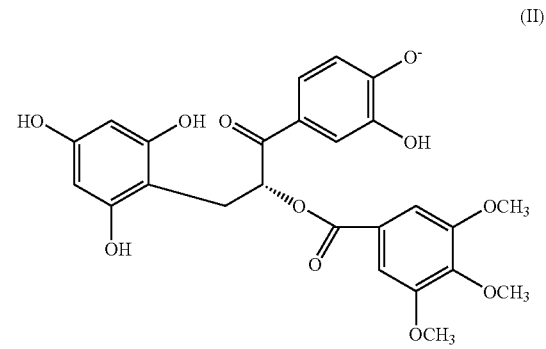

(II)

-continued (III)

[Chemical structure diagram]

In other embodiments, the compound of formula (XI) is 3,4,5-trimethoxy-catechin-3-gallate:

[Chemical structure diagram]

TMCG

For use in the methods described herein, there is provided a compound of formula (X):

[Chemical structure diagram labeled (X)]

wherein:
each —$R^1$, —$R^2$ and —$R^3$ is independently -$Q^1$, —OH or —H, where at least one of —$R^1$, —$R^2$ and —$R^3$ is not —H or —OH;
each —$R^4$ and —$R^5$ is independently -$Q^2$ or —H;
each -$Q^1$ is independently selected from:
 —F, —Cl,
 —$R^A$,
 —$OR^A$,
 —SH, —$SR^A$, where each —$R^A$ is independently selected from methyl and ethyl, which may substituted by one or more fluoro or chloro groups;
each -$Q^2$ is selected from:
 —F, —Cl,
 —$R^B$,
 —$OR^B$,
 —SH, —$SR^B$, where each —$R^B$ is independently selected from methyl and ethyl, which may substituted by one or more fluoro or chloro groups or an isomer, salt, solvate or prodrug thereof.

In some embodiments, the compound is a compound of formula (X) or an isomer thereof.

In some embodiments, when —$R^4$, —$R^5$ are each —H, the following provisos apply:
(i) —$R^1$, —$R^2$, and —$R^3$ are not all —OMe;
(ii) —$R^1$, —$R^2$, and —$R^3$ are not all —F;
(ii) —$R^2$ is not —$OCF_3$, where each of —$R^1$ and —$R^3$ is —H; and
(iv) —$R^2$ is not —H, where each of —$R^1$ and —$R^3$ is —F.

In some embodiments, —$R^1$, —$R^2$ and —$R^3$ are the same.
In some embodiments —$R^1$ and —$R^3$ are the same.
In some embodiments, each of —$R^2$, —$R^3$ and —$R^4$ is independently selected from —H, —F, —Cl, —Br, —I, and —$OR^{A1}$.

In some embodiments, each -$Q^1$ is independently selected from: —F, —Cl, —$R^A$, and —$OR^A$.

In some embodiments, each of —$R^1$, —$R^2$ and —$R^3$ is independently selected from —$OR^A$.

In some embodiments, each —$R^A$ is independently methyl, which may be substituted by one or more fluoro or chloro groups.

In some embodiments, each —$R^A$ is unsubstituted methyl.
In some embodiments, one of —$R^4$ and —$R^5$ is —H.
In some embodiments, both of —$R^4$ and —$R^5$ is —H.
In some embodiments, one of —$R^4$ and —$R^5$ is —$R^B$.

Also suitable for use in the methods described herein is a compound of formula (XI):

[Chemical structure diagram labeled (XI)]

wherein —$R^1$, —$R^2$, —$R^3$, —$R^4$ and —$R^5$ are defined according to the compound of formula (X) or an isomer, salt, solvate or prodrug thereof.

In some embodiments, the compounds are of formula (XIa):

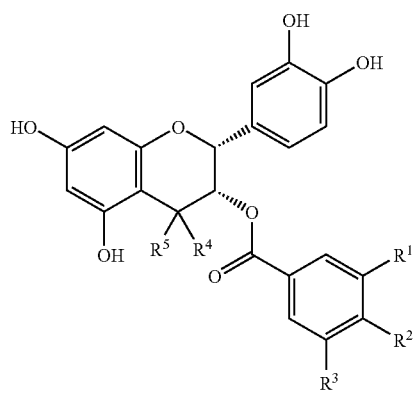
(XIa)

In other embodiments, the compounds are of formula (XIb):

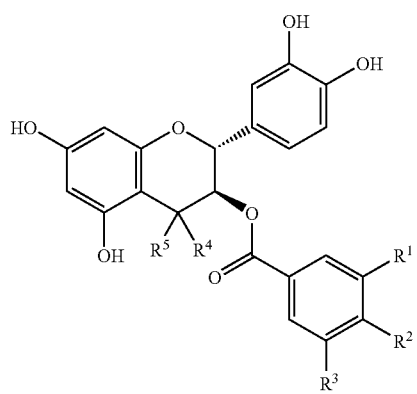
(XIb)

Preferably, the compound is a compound of formula (XI) or an isomer thereof.

Particularly suitable are prodrugs of compound (XI) wherein one or more of the hydroxy groups is esterfied to an —O—C(═O)—$R^C$ group, where $R^C$ is selected from methyl and ethyl.

In some embodiments, $R^C$ is methyl.

In some embodiments, $R^2$ is a hydroxy group and is the only hydroxy esterified to an —O—C(═O)-Me group. In other embodiments, $R^2$ is a hydroxy group and all the hydroxy groups are esterified to an —O—C(═O)—Me group.

Of particular relevance are the prodrug compounds:

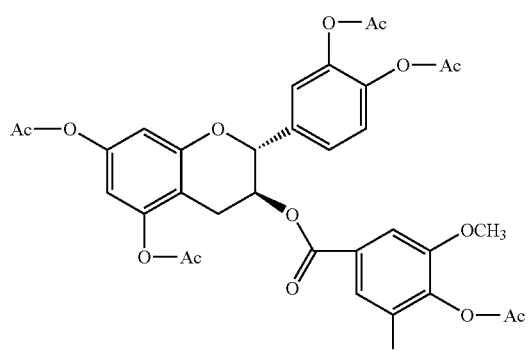

SCGAc(5)

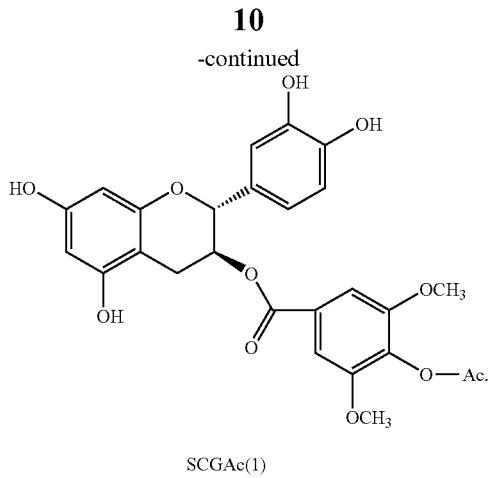

SCGAc(1)

Also of interest are the following compounds of formula (X):

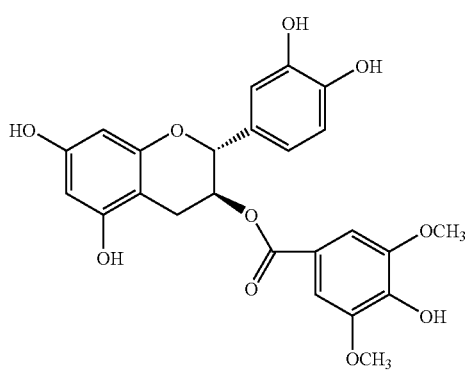

SCG

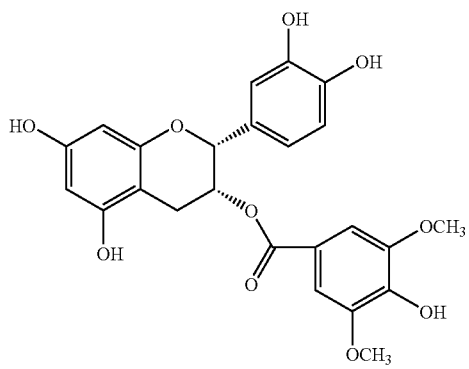

SECG

A reference to a compound of formula (X) also includes reference to the canonical forms of the structure shown. For example, reference to the compound of formula (II) includes reference to the compound of formula (III):

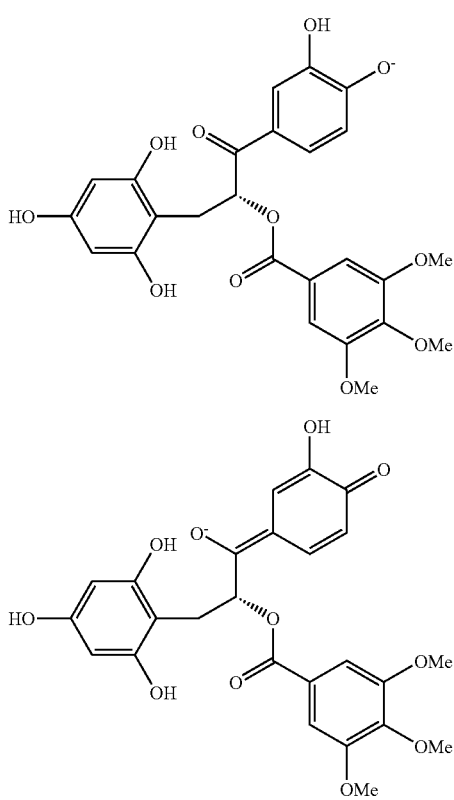

Suitable methods for the synthesis of the compounds of formula (X) and (XI) are described in detail below. Particularly, suitable methods for the synthesis of the compounds 3,4,5-trimethoxy-epicatechin-3-gallate are described.

In one or more aspects of the present invention (e.g., compounds for use in therapy, use of compounds in the manufacture of a medicament, methods, methods of treatment, etc.), the compounds are optionally as defined herein, but without any of the provisos.

Another aspect of the invention provides a method of treating melanoma or other cancer, comprising administering to an individual in need thereof a therapeutically effective dose of a compound of formula (X) or a compound of formula (XI).

Related aspects provide a compound of formula (X) or of formula (XI) for use in the treatment of melanoma or other cancer, and the use of a compound of formula (X) or of formula (XI) in the manufacture of a medicament for use in the treatment of melanoma or other cancer.

In other aspects of the invention there are provided compounds of formula (X) and compounds of formula (XI).

Unless otherwise specified, references to a compound herein also include isomeric, ionic, salt, solvate, and protected forms of the compound. For example, a reference to a hydroxyl group also includes the anionic form (—O⁻), a salt or solvate thereof, as well as conventional protected forms of a hydroxyl group. Ionic forms, salts, solvates, and protected forms of any particular compound are readily apparent to the skilled person.

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

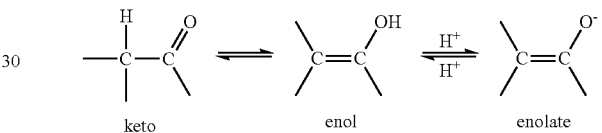

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts", *J. Pharm. Sci.*, Vol. 66, pp. 1-19.

The compounds of formula (X) may be ionic, typically anionic. Where the compound is ionic, there may be a pharmaceutically acceptable counter ion. Where such a counter ion is present, the compounds of formula (X) may be referred to as pharmaceutically acceptable salts.

The compounds of the invention may also be zwitterionic.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., $—NH_2$ may be $—NH_3^+$), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-7}$ alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxycarbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

A prodrug of a compound of formula (X) may include a compound of formula (XI). In this embodiment, the compound of formula (XI) may be activated by hydrolysis of the chromane ring. The activation may be mediated by an enzyme, for example a peroxidase or a tyrosinase. The enzyme is preferably tyrosinase.

A prodrug of a compound of formula (II) or (III) may include 3,4,5-trimethoxy-epicatechin-3-gallate.

Compounds, as described herein, may be in substantially purified form and/or in a form substantially free from contaminants. Each compound described herein may be isolated from a reaction mixture. Isolation refers to the separation of the product from unreacted starting material, other reaction products, reagents and, optionally, solvent.

The substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in some embodiments, the substantially purified form refers to a mixture of stereoisomers, i.e., purified with respect to other compounds. In other embodiments, the substantially purified form refers to one stereoisomer, e.g., optically pure stereoisomer. In some embodiments, the substantially purified form refers to a mixture of enantiomers, for example the substantially purified form may refer to an equimolar mixture of enantiomers (i.e., a racemic mixture, a racemate). In other embodiments, the substantially purified form refers to one enantiomer, e.g. optically pure enantiomer.

In some embodiments, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

The purity may be established by one or more of analytical and spectroscopic techniques including NMR (e.g. $^{13}C$ or $^1H$), LC-MS, HPLC, TLC, UV, IR and gravimetric analysis.

Unless specified, the contaminants refer to other compounds, that is, other than stereoisomers or enantiomers. In some embodiments, the contaminants refer to other compounds and other stereoisomers. In some embodiments, the contaminants refer to other compounds and the other enantiomer.

The substantially purified form may be at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Techniques for the separation of the compounds include, where appropriate, chromatography, including flash column chromatography, preparative HPLC and preparative TLC, crystallisation, distillation, and aqueous-organic extraction amongst others.

Where a compound of formula (XVI) is isolated, it may be isolated from byproducts, including compounds of formula (XVII). Advantageously, compounds of formula (XVII) may be isolated, and can be recycled in a reaction to generate more compound of formula (XVI).

An individual suitable for treatment as described herein may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human. In some preferred embodiments, the individual may be human or equine.

An ECG derivative as described herein may be the sole therapeutic agent which is administered to the individual or the ECG derivative may be administered in combination with one or more additional active compounds.

For example, the data set out herein shows that the ECG derivatives described above increase the amount of folate receptor alpha (FRα) (GeneID: 2348; nucleic acid database entry NM_000802.2 GI: 12056965; amino acid database entry; NP_000793.1 GI: 4758400) in the cell membrane of melanoma cells. The compounds may therefore be useful in sensitising melanoma cells to cytotoxic FRα ligands.

Another aspect of the invention provides a method of treating melanoma or other cancer, comprising administering to an individual in need thereof a therapeutically effective dose of a combination of an ECG derivative described above and a cytotoxic FRα ligand.

Related aspects provide a combination of an ECG derivative described above and a cytotoxic FRα ligand for use in the treatment of melanoma or other cancer, and the use of a combination of an ECG derivative described above and a cytotoxic FRα ligand in the manufacture of a medicament for use in the treatment of melanoma or other cancer.

A cytotoxic FRα ligand is a compound which is imported into cells via the FRα receptor and which exerts a toxic effect on the cells, for example by suppressing cell function, reproduction or growth or promoting or inducing cell death. Examples of cytotoxic FRα ligands include antifolate chemotherapeutic agents such as pemetrexed (2-[4-[2-(4-amino-2-oxo-3,5,7-triazabicyclo[4.3.0]nona-3,8,10-trien-9-yl)ethyl]benzoyl]aminopentanedioic acid) BGC945 and BGC638 and analogues and derivatives thereof.

BGC945 and BGC638 are antifolates which are efficiently taken up into cells solely via FRα but not through the RFC and which have been shown to be selective and highly cytotoxic to α-FR overexpressing tumour cell lines in vitro (A. L. Jackman, et al, *Br. J. Cancer* 88 (2003), p. S21).

Figure 2:
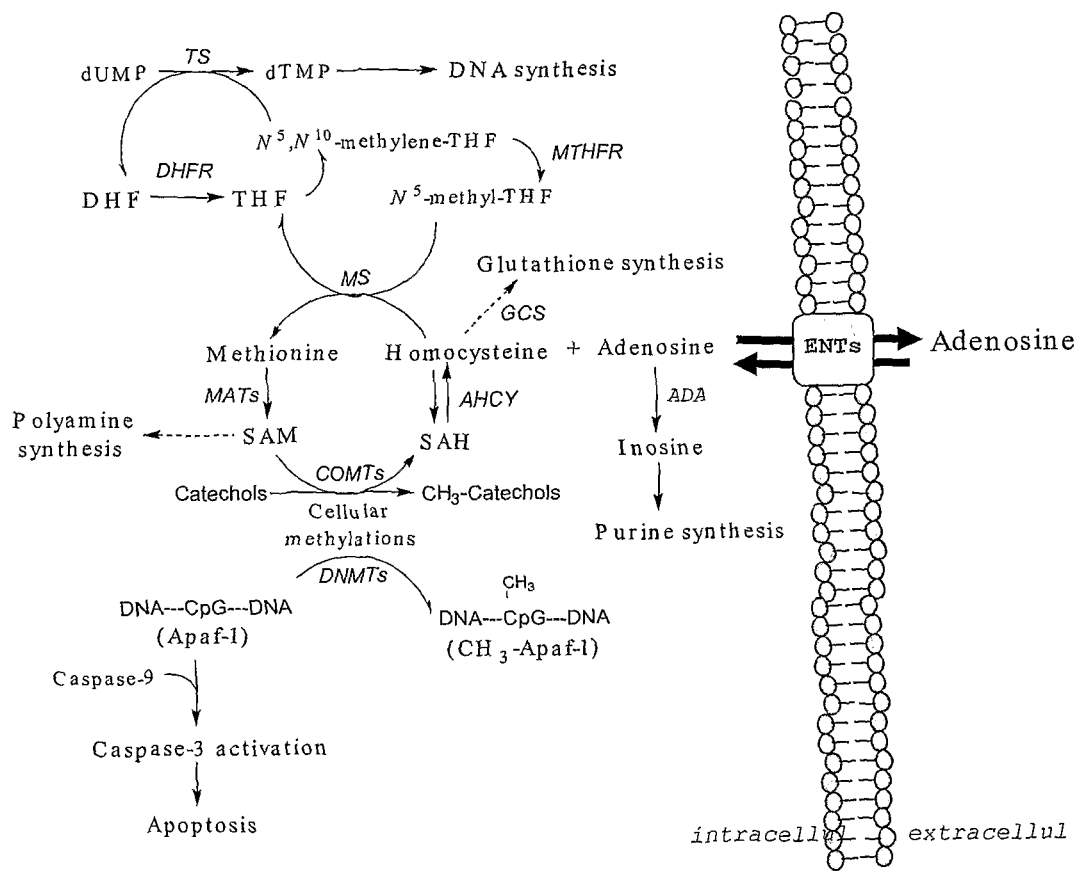
FIG. 2 shows the methionine cycle and its connections with several metabolic and survival cell pathways. Abbreviations: ADA, adenosine deaminase; AHCY, S-adenosylhomocysteine hydrolase; Apaf-1, Apoptosis protease-activating factor-1; DHF, dihydrofolate; DNMT, COMT, catechol-O-methyltransferase; DHFR, dihydrofolate reductase; DNA methyltransferase; ENT, equilibrative nucleoside transporter; GCS, γ-glutamylcysteine synthetase; MAT, methionine adenosyltransferase; MS, methionine synthase; MTHFR, 5,10-methylenetetrahydrofolate reductase; SAH, S-adenosylhomocysteine; SAM, S-adenosylmethionine; THF, tetrahydrofolate; TS, thymine synthase.

The data set out herein shows that the anti-proliferative effect of the ECG derivatives described above on melanoma cells is increased or potentiated by compounds which inhibit the methionine cycle. The substrates and enzymes of the methionine cycle are shown in FIG. 2. Methionine cycle inhibitors may therefore be useful in potentiating the effect of the ECG derivatives described herein.

Another aspect provides a method of treating melanoma or other cancer, comprising administering to an individual in need thereof a therapeutically effective dose of a combination of one or more methionine cycle inhibitors and an ECG derivative described above.

Related aspects provide a combination of an ECG derivative described above and a methionine cycle inhibitor for use in the treatment of melanoma or other cancer, and the use of a combination of an ECG derivative described above and a methionine cycle inhibitor in the manufacture of a medicament for use in the treatment of melanoma or other cancer.

A methionine cycle inhibitor is a compound which directly or indirectly inhibits or reduces the interconversion of methionine and homocysteine in cells. A methionine cycle inhibitor may, for example, reduce intracellular levels of methionine and/or homocysteine in a cell and/or reduce the activity and/or expression of one or more enzymes in the methionine cycle, such as methionine synthase (MS; nucleotide; NM_000254.1 GI:4557764; GeneID: 4548; amino acid NP_000245.1 GI:4557765), methionine adenosyltransferase 1A (MAT1A; GeneID: 4143; nucleotide NM_000429.2 GI:67906818; amino acid NP_000420.1 GI:4557737), methionine adenosyltransferase 2A (MAT2A: GeneID: 41441; nucleotide; NM_005911.4 GI:46852159, amino acid; NP_005902.1 GI:5174529) and S-adenosylhomocysteine hydrolase (AHCY; GeneID: 191; nucleotide; NM_000687.1 GI:9951914 amino acid NP_000678.1 GI:9951915).

Suitable methionine cycle inhibitors may include MAT2A inhibitors, such as s-adenosylmethionine, 5'-methylthioadenosine, 5-azacytidine and 5-aza-2'-deoxycytidine, agents which increase intracellular adenosine levels, such as adenosine and pirydamole, and ornithine decarboxylase inhibitors, such as difluoromethylornithine.

The data set out herein shows that the anti-proliferative effect of the ECG derivatives described above on melanoma cells is increased or potentiated by compounds which reduce or inhibit the level of dihydrotestosterone (DHT) in cells. Anti-androgens and other compounds which reduce or inhibit the level of dihydrotestosterone (DHT) may therefore be useful in potentiating the effect of the ECG derivatives described herein, in particular in male patients.

Another aspect provides a method of treating melanoma or other cancer, such as breast cancer, comprising administering to an individual in need thereof a therapeutically effective dose of a combination of one or more compounds which reduce or inhibit the level of dihydrotestosterone and an ECG derivative described above.

Related aspects provide a combination of an ECG derivative described above and a compound which reduces or inhibits the level of dihydrotestosterone for use in the treatment of melanoma or other cancer, and the use of a combination of an ECG derivative described above and a compound which reduces or inhibits the level of dihydrotestosterone in the manufacture of a medicament for use in the treatment of melanoma or other cancer.

Compounds which reduce or inhibit the level of dihydrotestosterone include anti-androgens. Anti-androgens may be antagonists of the androgen receptors, such as flutamide (Eulexin™), nilutamide (Anandron™, Nilandron™) and bicalutamide (Casodex™), or inhibitors of the testosterone 5α-reductase, such as finasteride (Proscar™, Propecia™) and dutasteride (Avodart™), which prevent the conversion of testosterone into dihydrotestosterone (DHT).

Related aspects provide a combination of an ECG derivative described above and a compound which reduces or inhibits the pentose phosphate pathway for use in the treatment of melanoma or other cancer and the use of a combination of an ECG derivative described above and a compound which reduces or inhibits the pentose phosphate pathway in the manufacture of a medicament for use in the treatment of melanoma or other cancer.

Compounds which reduce or inhibit the pentose phosphate pathway include dehydroepiabdrosterone (DHEA).

Thymidylate synthase inhibitors may also be useful in potentiating the effect of the ECG derivatives described herein, in particular in male patients.

Another aspect provides a method of treating melanoma or other cancer comprising administering to an individual in need thereof a therapeutically effective dose of a combination of one or more thymidylate synthase inhibitors and an ECG derivative described above.

Related aspects provide a combination of an ECG derivative described above and a thymidylate synthase inhibitor for use in the treatment of melanoma or other cancer and the use of a combination of an ECG derivative described above and a thymidylate synthase inhibitor in the manufacture of a medicament for use in the treatment of melanoma or other cancer.

Suitable thymidylate synthase (TS) inhibitors include 5-fluorouracil (5-FU), fluorodeoxyuridine (FdUrd), raltitrexed, or nolatrexed.

The methods described herein may be the sole therapy which is administered to the individual or may be administered in combination with one or more additional therapies. For example, the methods described herein may be administered as an adjunct to surgical interventions such as surgical removal of the tumor; chemotherapy, for example with dacarbazine (also termed DTIC); immunotherapy, for example with IL-2 or IFN, or radiation therapy. The use of such therapies in the treatment of melanoma is well-known in the art. The compounds or combinations of compounds described herein may be administered to the individual before, simultaneous with and/or after treatment with the one or more additional therapies.

ECG derivatives for use in treating melanoma as described herein inhibit the activity of dihydrofolate reductase (DHFR) i.e. they possess anti-folate activity. The ECG derivatives may possess intrinsic activity (drugs) or may be prodrugs of active compounds which may themselves exhibit little or no intrinsic activity. Suitable assays to determine the inhibition of dihydrofolate reductase (DHFR) by a compound are well-known in the art.

Methods of measuring the effect of a compound on the proliferation of melanoma cells are well-known in the art and are exemplified herein. For example, the effect of a compound on the proliferation of melanoma cells may be determined by contacting melanoma cells with the compound, preferably in the form of a pharmaceutically acceptable composition, and determining the growth of the melanoma cells. A reduction in the growth of melanoma cells treated with the compound relative to untreated melanoma cells is indicative that the compound has an anti-proliferative effect on the melanoma cells. Suitable methods may be practiced in vitro or in vivo.

The term "treatment" as used herein in the context of treating a condition, pertains generally to treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, and cure of the condition. Treatment as a prophylactic measure (i.e. prophylaxis) is also included. For example, an individual susceptible to or at risk of the occurrence or re-occurrence of melanoma may be treated as described herein. Such treatment may prevent or delay the occurrence or re-occurrence of melanoma in the individual.

The term "therapeutically-effective amount" as used herein, pertains to that amount of an active compound, or a material, composition or dosage from comprising an active compound, which is effective for producing some desired therapeutic effect, commensurate with a reasonable benefit/risk ratio.

Melanoma is a malignant neoplasm of melanocytes in the skin. Melanoma which may be treated as described herein may include primary melanoma, for example, superficial spreading melanoma, nodular melanoma, acral lentiginous melanoma or lentigo maligna (melanoma); and metastatic melanoma, for example melanoma displaying local or distant metastases. The melanoma may be at any stage. For example, the melanoma may be stage 0, I, II, III or IV melanoma as described in Balch C et al (2001). *J Clin Oncol* 19 (16): 3635-48.

In addition to melanoma, the compounds and combinations described may also be useful in the treatment of other forms of cancer, for example bladder cancer, breast cancer, uterus cancer, ovary cancer, prostate cancer, lung cancer, colorectal cancer, cervical cancer, liver cancer, head and neck cancer, oesophageal cancer, pancreas cancer, renal cancer, stomach cancer, cerebral cancer or non-melanoma skin cancer.

While it is possible for the ECG derivative to be administered alone, it is preferable to present it as a pharmaceutical composition (e.g. formulation) comprising an ECG derivative as defined above and, optionally a compound which reduce or inhibit the level of dihydrotestosterone, a pentose phosphate pathway inhibitor, methionine cycle inhibitor, thymidylate synthase inhibitor and/or cytoxic FRα ligand, as described above, together with one or more pharmaceutically acceptable carriers, adjuvants, excipients, diluents, fillers, buffers, stabilisers, preservatives, lubricants, or other materials well known to those skilled in the art. Optionally, other therapeutic or prophylactic agents may be included.

Thus, the present invention further provides pharmaceutical compositions, as defined above, and methods of making a pharmaceutical composition comprising admixing an ECG derivative and, optionally a compound which reduce or inhibit the level of dihydrotestosterone, a pentose phosphate pathway inhibitor, methionine cycle inhibitor, thymidylate synthase inhibitor and/or cytoxic FRα ligand, as described above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, Remington's Pharmaceutical Sciences, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded, tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

Other aspects of the invention relate to the identification of compounds which may be useful in combination with the compounds described above in the treatment of melanoma or other cancers.

A method of screening for a compound which is useful for the treatment of melanoma or other cancers in combination with a compound described above may comprise;
    determining the ability of a test compound to inhibit the activity of the methionine cycle or increase the level of adenosine in a cell.

A test compound which inhibits the activity of the methionine cycle and/or increases the level of adenosine in the cell relative to controls may be useful for the treatment of melanoma in combination with an ECG derivative described above. Suitable controls include cells which are not treated with the test compound.

Inhibition of the methionine cycle may be determined by a reduction in the activity and/or expression of one or more enzymes in the methionine cycle and/or the intracellular level of one or more intermediates in the cycle, such as methionine and homocysteine, in the presence of the compound, relative to its absence.

Suitable methods for determining the activity and/or expression of one or more enzymes in the methionine cycle and intracellular levels of intermediates in the methionine cycle are well known in the art.

Expression of a methionine cycle enzyme in a cell may be determined by measuring the amount of protein or the amount of transcribed nucleic acid which encodes the protein, in the cell.

Increases in the level of adenosine in the cell may be determined by measuring intracellular adenosine levels in the presence relative to the absence of a test compound.

Suitable methods for determining intracellular levels of adenosine are well known in the art.

Another method of screening for a compound which is useful for the treatment of melanoma or other cancers in combination with a compound described above may comprise;
    determining the ability of a test compound to reduce or inhibit the level of dihydrotestosterone in a cell.

A test compound which reduces or inhibits the level of dihydrotestosterone in the cell relative to controls may be useful for the treatment of melanoma or other cancers in combination with an ECG derivative described above. Suitable controls include cells which are not treated with the test compound Another method of screening for a compound which is useful for the treatment of melanoma or other cancers in combination with a compound described above comprising;
    determining the ability of a test compound to reduce or inhibit the pentose phosphate pathway in a cell.

A test compound which inhibits pentose phosphate pathway in the cell relative to controls may be useful for the treatment of melanoma or other cancers in combination with an ECG derivative described above. Suitable controls include cells which are not treated with the test compound Another method of screening for a compound which is useful for the treatment of melanoma or other cancers in combination with a compound described above comprising;

determining the ability of a test compound to inhibit thymidylate synthase in a cell.

A test compound which inhibits thymidylate synthase in the cell relative to controls may be useful for the treatment of melanoma or other cancers in combination with an ECG derivative described above. Suitable controls include cells which are not treated with the test compound Methods may be in vitro methods using isolated cells in culture. Test compound may be contacted with the cells by supplementing the buffer or culture medium with the test compound.

Methods may be in vivo methods using cells which are comprised in a non-human animal, for example a mammal, such as a mouse. Test compound may be contacted with the cells by administering the test compound to the non-human animal.

Compounds which may be screened using the methods described herein may be natural or synthetic chemical compounds used in drug screening programmes. Extracts of plants, microbes or other organisms which contain several characterised or uncharacterised components may also be used.

A method may, for example, comprise identifying the test compound as a compound which inhibits the activity of the methionine cycle; increases the level of adenosine in a cell; or other activity described above; and which may be useful in combination with an ECG derivative described herein in the treatment of melanoma.

A test compound identified using one or more initial screens as having ability to inhibit the activity of the methionine cycle or increase the level of adenosine in a cell, or other activity described above, may be assessed further using one or more secondary screens. A secondary screen may, for example, involve testing for a biological function such as an effect on the proliferation of melanoma in combination with an ECG derivative described above.

Other aspects of the invention provide a method of producing compounds of formula (X) and (XI).

A compound of formula (XI) may be synthesised by deprotecting a compound of formula (XV):

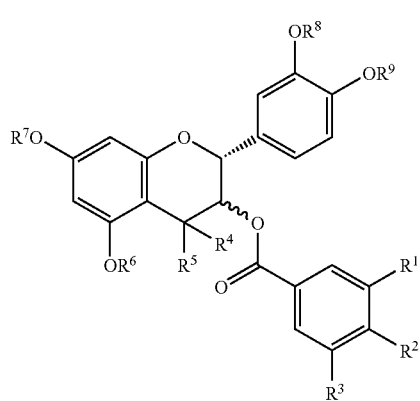

(XV)

wherein each of $R^6$, $R^7$, $R^8$ and $R^9$ are hydroxy protecting groups, as are well known in the art.

A compound of formula (XV) may be synthesised by coupling a compound of formula (XIV):

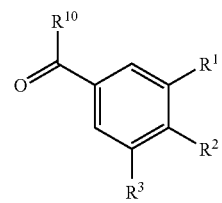

(XIV)

with a compound of formula (XIII):

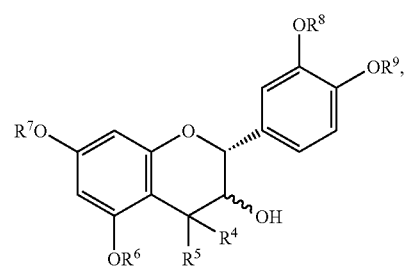

(XIII)

wherein $R^{10}$ is independently selected from —OH, —F, —Cl, —Br, and —I.

If the compound of formula (XI) is of formula (XIa) then the compound of formula (XIIIa):

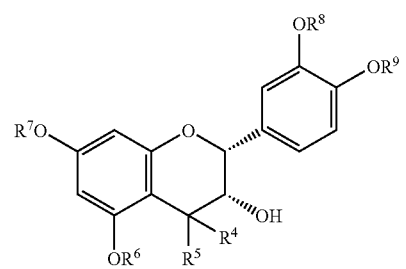

(XIIIa)

may be synthesised from a compound of formula (XIIIb) by inverting the stereochemistry of the compound of formula (XIIIb) at the C-3 position:

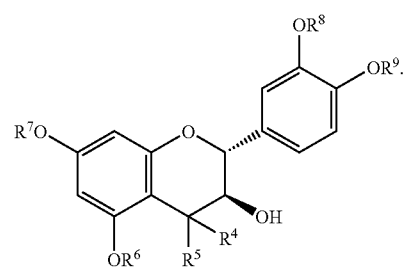

(XIIIb)

The preferences for the compounds of formula (X) are also applicable to the compounds of formulas (XII), (XIII), (XIV), and (XV), where appropriate.

In some embodiments, —$R^6$, —$R^7$, —$R^8$, and —$R^9$ are the same, for example benzyl.

In some embodiments, —$R^{10}$ is —OH.

In some embodiments, —$R^{10}$ is —F, —Cl, —Br, and —I.

In some embodiments, —$R^{10}$ is —Cl.

In some embodiments, (XIV) is 3,4,5-trimethoxybenzoyl chloride.

The compound of formula (XIV) may be used in the reaction as a carboxylic acid ($R^{10}$ is —OH) or as an acyl halide ($R^{10}$ is —F, —Cl, —Br, or —I). The acyl halide may be generated from the carboxylic acid form. For example, 3,4,5-trimethoxybenzoic acid may be converted to 3,4,5-trimethoxybenzoyl chloride in the presence of a halide source such as $PCl_5$.

Coupling (or condensation) reagents, such as DMAP, may be used to facilitate the coupling reaction between (XIII) and (XIV). Other coupling reagents include HOBt, water soluble carbodiimide (WSC), MSNT, BOP, PyBOP, TBTU, HBTU, HATU, and CDI. An organic or inorganic base may be used along with the coupling agent.

In other aspects of the invention, the compound of formula (XIII) encompasses the active ester formed when the carboxylic acid is treated with a coupling mixture comprising one or more of the coupling reagents listed above.

In some embodiments, the method comprises the preliminary step of preparing a compound of formula (XIII), wherein catchecin or gallocatechin, where appropriate, is converted to a compound of formula (XIII). In some embodiments, catechin or gallocatechin, where appropriate, is reacted with X—$R^{OPROT}$, where —X is selected from —F, —Cl, —Br, and —I, and —$R^{OPROT}$ is the hydroxy protecting group as defined for the compounds of formula (XI).

The step of inverting the stereochemistry of the compound of formula (XIIIb) at the C-3 position comprises the step of oxidising the compound of formula (XIIIb) to produce a compound of formula (XVI)

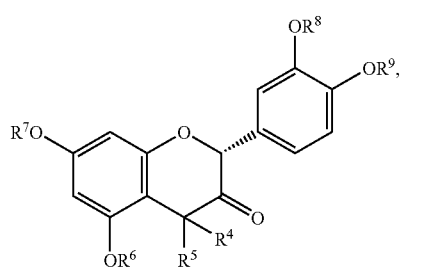

(XVI)

then reducing the compound of formula (XVI) to give a compound of formula (XIIIa), wherein —$R^4$, —$R^5$, —$R^6$, —$R^7$, —$R^8$, and —$R^9$ are defined according to the compounds of formula (XIII).

In some embodiments, the compound of formula (XIIIb) is oxidised in the presence of Dess-Martin periodinane, TPAP-NMO, Oppenauuer reagents (fluorenone, $KOCMe_3$), DMSO/$Ac_2O$, pyridinium dichromate or Swern reagents.

In some embodiments, the compound of formula (XIIIb) is oxidised in the presence of Dess-Martin periodinane, Oppenauuer reagents or DMSO/$Ac_2O$.

In some embodiments, the compound of formula (XIIIb) is oxidised in the presence of Dess-Martin periodinane.

Swern reagents include oxalyl chloride, DMSO and an amine base. The amine base may be selected from triethylamine (TEA), and diisopropylethylamine (DIPEA). Triethylamine is most preferred. DMSO may be replaced with dodecyl methyl sulfide. Oxalyl chloride may be replaced with trifluoroacetic anhydride. Other variations may be used, such as those described in Tidwell, *Synthesis* 1990, 857-870.

In some embodiments, the compound of formula (XVI) is reduced in the presence of L-Selectride® (Lithium tri-sec-butylborohydride), DIBALH, sodium borohydride ($NaBH_4$), $LiBHEt_3$ and $LiAlH_4$.

In some embodiments, the compound of formula (XVI) is reduced in the presence of L-Selectride®, DIBALH, sodium borohydride and $LiBHEt_3$.

In some embodiments, the compound of formula (XVI) is reduced in the presence of L-Selectride®.

In some embodiments, the compound of formula (XVI) is reduced in the presence of one or more reducing agent additives. Each additive may selected from $ZnCl_2$, $CeCl_3$, LiBr and n-$Bu_4NCl$.

In some embodiments, the reducing agent is an agent that is capable of diastereoselective reduction. That is, the reducing agent allows the production of a product that is at least 70% optically pure, at least 80% optically pure, at least 90% optically pure, at least 95% optically pure, at least 97% optically pure, at least 98% optically pure, or at least 99% optically pure. In some embodiments, the product is at least 90% optically pure.

The deprotection step may be carried out using the appropriate agents to remove the hydroxyl protecting groups. For example, if the hydroxyl protecting group is benzyl, then these may be removed by a hydrogenation reaction.

In some embodiments, there is provided a method of producing 3,4,5-trimethoxy-epicatechin-3-gallate comprising the steps:

i) reacting catechin with benzyl bromide to produce a compound of formula (IV),

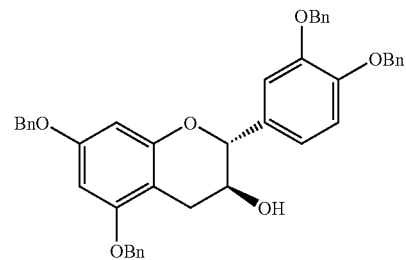

(IV)

ii) inverting the stereochemistry of the compound of formula (IV) at the C-3 position to produce a compound of formula (VI)

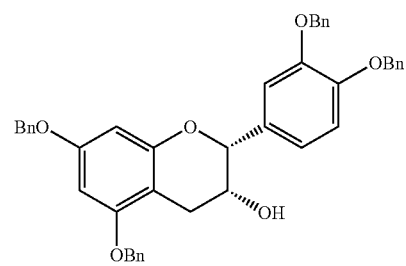

(VI)

iii) reacting the compound of formula (VI) with 3,4,5-trimethoxybenzoyl chloride to produce a compound of formula (VII),

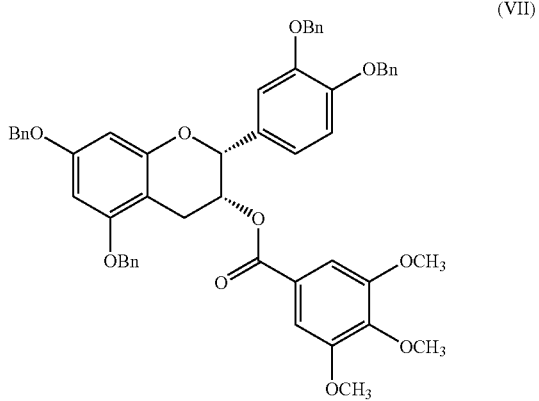 [SMILES: COc1cc(C(=O)O[C@@H]2Cc3c(OCc4ccccc4)cc(OCc4ccccc4)cc3O[C@@H]2c2ccc(OCc3ccccc3)c(OCc3ccccc3)c2)cc(OC)c1OC]

(VII)

iv) deprotecting the compound of formula (VII) to produce 3,4,5-trimethoxy-epicatechin-3-gallate.

In some embodiments, the step of inverting the stereochemistry of the compound of formula (IV) comprises oxidising the compound of formula (IV) to produce a compound of formula (V),

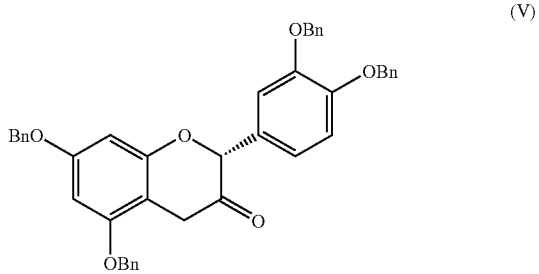 [SMILES: O=C1Cc2c(OCc3ccccc3)cc(OCc3ccccc3)cc2O[C@@H]1c1ccc(OCc2ccccc2)c(OCc2ccccc2)c1]

(V)

then reducing the ketone at the C-3 position to produce a compound of formula (VI).

Compounds (IV), (V) and (VI) may be obtained using the experimental procedures described in JASC 1999, 121, 12073-12081.

Suitable conditions for step i) include the presence of $K_2CO_3$ in DMF at −15° C. to room temp.

Suitable conditions for the oxidation described as an embodiment step ii) include the presence of Dess-Martin periodinane, moist $CH_2Cl_2$, at room temp.

Suitable conditions for step the reduction described as an embodiment in step ii) include the presence of L-Selectride®, n-$Bu_4$NCl, THF, at −78° C.

Suitable conditions for step iii) include the presence of 3,4,5-trimethoxybenzoyl chloride, $CH_2Cl_2$, DMAP, at −15° C. to room temp.

Suitable conditions for step iv) include the presence of $H_2$, 20% $Pd(OH)_2$/C, THF/MeOH, at room temp.

Trimethoxybenzoyl chloride may be conveniently produced, for example by refluxing 3,4,5-trimethoxybenzoic acid in the presence of $PCl_5$ and $C_7H_8$.

In another aspect of the invention there is provided a method of producing a compound of formula (X) from a compound of formula (XI). In some embodiments, the step of converting the compound of formula (XI) to the compound of formula (X) comprises the step of treating the compound of formula (XI) with a suitable oxidative enzyme. The enzyme may be a tyrosinase or a peroxidase. The enzyme may be a polyphenoloxidase. In these embodiments, the treatment may occur in an acidic environment. Preferably, the product of the treatment step is then exposed to a neutral or alkaline environment. Any or all of these steps may be performed in vivo or in vitro.

In other embodiments, the step of converting the compound of formula (XI) to the compound of formula (X) comprises the step of treating the compound of formula (XI) with aqueous alkaline solution. In principle, any aqueous alkaline solution may be used. However, solutions prepared using hydroxides or carbonates of alkali metals or alkaline earth metals are preferred. Solutions prepared from sodium hydroxide, sodium hydrogen carbonate and sodium bicarbonate are most preferred.

Additionally or alternatively, the compound of formula (XI) may be converted to the compound of formula (X) by the irradiation of the compound of formula (XI) with light. Typically, ultraviolet (UV) light may be used.

In some embodiments, the method of producing a compound of formula (X) may comprise the steps of the methods described above for the production of a compound of formula (XI).

The results set out herein show that a soluble truncated form of the FRα receptor is present in melanoma cells but not in normal melanocytes.

Another aspect of the invention provides a method of identifying a melanoma cell comprising;
  determining the presence or absence of a soluble folate receptor alpha (FRα) polypeptide in a candidate cell,
  wherein the presence of the soluble FRα polypeptide is indicative that the candidate cell is a melanoma cell.

The candidate cell may be comprised in a sample of cells obtained from the individual, for example a cell or tissue sample or biopsy. The present methods may be useful, for example, in determining the presence of a melanoma cell in a sample obtained from an individual. The presence of a melanoma cell is indicative that the individual is suffering from melanoma.

The individual may be healthy or may be suspected of or at risk of suffering from melanoma. In some embodiments, the cell may be suspected of being a cancer cell or a melanoma cell, or may be present in a sample of tissue which is suspected to be cancer tissue or melanoma tissue.

A soluble FRα polypeptide may have the sequence of SEQ ID NO: 1 or may be an allelic variant thereof.

The soluble FRα polypeptide may be encoded by an alternatively spliced mRNA having the nucleotide sequence of SEQ ID NO: 2 An amino acid or nucleotide sequence which is an allelic variant of a soluble FRα polypeptide set out herein may comprise a sequence which shares greater than about 90% sequence identity with the reference sequence, greater than about 95%, greater than about 98%, or greater than about 99%.

For example, a soluble FRα polypeptide may have a sequence with one or more of addition, insertion, deletion or substitution of one or more amino acids from the corresponding sequence in SEQ ID NO: 1. For example, up to about 5, 10, 15, 20, 30 or 40 amino acids may be altered. Such alterations may be caused by one or more of addition, insertion, deletion or substitution of one or more nucleotides in the encoding nucleic acid.

Sequence identity is commonly defined with reference to the algorithm GAP (Genetics Computer Group, Madison, Wis.). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol. Biol. 147: 195-197), or the TBLASTN program, of Altschul et al. (1990) supra, generally employing default parameters. In particular, the psi-Blast algorithm (Nucl. Acids Res. (1997) 25 3389-3402) may be used. Sequence identity may also be determined using Genomequest™ software (Gene-IT, Worcester Mass. USA).

Sequence comparisons are preferably made over at least 30 amino acids, at least 50 amino acids, at least 75 amino acids, at least 100 amino acids, at least 125 amino acids, at least 140 amino acids, at least 150 amino acids, or over the full-length of the relevant sequence described herein The soluble FRα polypeptide may have a molecular weight of about 16 kDa in its mature glycosylated form.

The presence of the soluble FRα polypeptide may be determined by any convenient technique. In some embodiments, the soluble FRα polypeptide may be detected at the amino acid level. Numerous techniques and formats for determining the presence or amount of a target polypeptide using a binding member, such as an antibody, or an antibody fragment or derivative, are well-known in the art, including, for example, Western blot analysis, immunohistochemistry (Angéle S et al (2000) Clin. Cancer Res. 6, 3536-3544) and immunoassays such as ELISA, lateral flow assays such as immunochromatographic strips, flow-through assays, agglutination assays or solid-phase assays such as dipstick or dipstick comb assays. (Butch A W et al (2004) Clinical Chemistry 50, 2303-2308; A Practical Guide to ELISA by D M Kemeny, Pergamon Press 1991; Principles and Practice of Immunoassay, $2^{nd}$ edition, C P Price & D J Newman, 1997, Stockton Press/Macmillan Reference). Antibodies to the soluble FRα polypeptide suitable for use in such methods may be produced using standard techniques. Preferably, antibodies bind to the soluble FRα polypeptide preferentially over the full-length FRα polypeptide. For example, a suitable antibody may bind to the soluble FRα polypeptide and show little or no binding to the full-length FRα polypeptide.

In some embodiments, the presence or amount of soluble FRα polypeptide in a cell may be determined by contacting a sample comprising one or more cells from an individual with a specific binding member directed against the soluble FRα polypeptide, and determining binding of the specific binding member to the sample.

In other embodiments, the presence of soluble FRα polypeptide may be detected at the nucleotide level.

A method of identifying a melanoma cell may comprise;
determining the level or amount of nucleic acid, for example mRNA, encoding a soluble FRα polypeptide in a candidate cell,
the presence of said nucleic acid being indicative that the candidate cell is a melanoma cell.

The level or amount of encoding nucleic acid in a cancer cell may be determined, for example by detecting the amount of transcribed encoding nucleic acid in the cell. This may be performed using standard techniques such as Northern blotting or RT-PCR.

The level of soluble FRα polypeptide, the amount of a nucleic acid encoding such soluble FRα polypeptide may be determined relative to normal (i.e. non-cancer) cells, preferably from the same tissue.

The presence of a melanoma cell identified as described above in a sample obtained from an individual is indicative that the individual has melanoma. The individual may then undergo treatment, for example treatment with an ECG compound as described above.

Various further aspects and embodiments of the present invention will be apparent to those skilled in the art in view of the present disclosure. All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described.

Experiments

Materials

Epicatechin (EC; >98%), ECG (>98%), NADPH, MTX and leucovorin (5-formyl-THF) were from Sigma Chemical Co. DHF (90%) was obtained from Aldrich Chemical Co. Recombinant human DHFR (rHDHFR) was purchased from Sigma and its concentration was determined by MTX titration of enzyme fluorescence (Smith et al., 1979).

Synthesis

TMECG was successfully synthesized (70% recovery) from catechin with the subsequent inversion of the stereochemistry at C-3 (Tuckmantel et al., 1999) and by reaction of with 3,4,5-trimethoxybenzoylchloride. The reaction sequence is outline in Scheme 1. This method yielded a 70% of recovery. Mushroom tyrosinase (Sigma) was used to synthesize its quinone methide (QM) related product.

Compounds 1, 2 and 3 were obtained using the experimental procedures described in J. Am. Chem. Soc. 1999, 121, 12073-12081.

3,4,5-trimetoxybenzoylchloride (4)

A mixture of 3,4,5-trimetoxibezoyl acid (3.0 g, 14.14 mmol) and phosphorous pentachloride (3.53 g, 16.95 mmol) in dry toluene (50 ml) was stirred at reflux temperature and under nitrogen for 3 h. The reaction is allowed to reach room temperature and the solvent was removed under vacuum. The product was obtained pure enough to be used in the next step without further purification.

5,7,3',4'-tetra-O-benzyl-3-(3",4",5"-trimethoxybenzoyl)-(−)-epicatechin (5)

To a solution of 3 (0.547 g, 0.84 mmol) in dry $CH_2Cl_2$ (50 ml) a solution of 4 (0.386 g, 1.68 mmol) in the same solvent was added dropwise under nitrogen. The reaction mixture was stirred at room temperature for 24 hours and then a solution of saturated sodium bicarbonate (30 ml) and ethyl acetate (50 ml) were added. Afterwards, the mixture was extracted twice with water (2×100 ml). The organic layers were dried with anhydrous magnesium sulphate and the solvent removed under vacuum. The resulting red oil was chromatographed on a silica gel column using n-Hex/AcOEt (6:4, v:v) as solvent ($r_f$=0.64). The solvent was removed under reduced pressure and the solid was recrystallized from $Et_2O$/n-Hex to obtain a white solid (yield=71%). MS (FAB$^+$) m/z (%) 845 (M$^+$+1, 10). $^1$H NMR (CDCl$_3$, 400 MHz) δ 7.30-7.43 (m, 20H, Ph), 7.17 (s, 2H, H2" y H6"), 7.13 (d, 1H, $^4$J=1.9 Hz, H2'), 7.07 (dd, 1H, $^3J$=8.4 Hz, $^4J$=1.9 Hz, H6'), 6.89 (d, 1H, $^3J$=8.4 Hz, H5'), 6.30 (d, 1H, $^4J$=2.2 Hz, H6), 6.28 (d, 1H, $^4J$=2.2 Hz, H8), 5.11 (s, 4H, 2×CH$_2$O), 5.03 (s, 2H, CH$_2$O), 5.02 (s, 2H, CH$_2$O), 4.97 (d, 1H, $^3J$=11.7 Hz, H2), 4.87 (d, 1H, $^3J$=11.7 Hz, H3), 3.83 (s, 3H, OCH$_3$), 3.80 (s, 6H, OCH$_3$), 3.10 (m, 2H, H4). $^{13}$C NMR (CDCl$_3$, 100 MHz) δ 164.9 (q, —COO), 158.4 (q, Ar—O), 157.6 (q, Ar—O), 155.2 (q, Ar—O), 152.5 (2×q, Ar—O), 148.6 (q, Ar—O), 142.0 (q, Ar—O), 136.8 (q, PhCH$_2$), 136.7 (q, PhCH$_2$), 136.5 (q, PhCH$_2$), 136.4 (q, PhCH$_2$), 130.8 (q, C1'), 128.2 (CH, PhCH$_2$), 128.1 (CH, PhCH$_2$), 128.0 (CH, PhCH$_2$), 127.6 (CH, PhCH$_2$), 127.5 (CH, PhCH$_2$), 127.4 (2×CH, PhCH$_2$), 127.1 (CH, PhCH$_2$), 127.0 (CH, PhCH$_2$), 126.9 (CH, PhCH$_2$), 126.8 (CH, PhCH$_2$), 124.7 (q, C1"), 119.6 (CH, C6'), 114.4 (CH, C6), 113.6 (CH, C2'), 106.7 (CH, C2" y C6"), 100.5 (q, C4a), 94.2 (CH, C6), 93.5 (CH, C8), 71.2 (CH$_2$, CH$_2$Ph), 70.9 (CH$_2$, CH$_2$Ph), 69.8 (CH$_2$, CH$_2$Ph), 69.6 (CH$_2$, CH$_2$Ph), 68.5 (CH, C3), 60.5 (CH$_3$, OCH$_3$), 55.8 (CH$_3$, OCH$_3$), 25.5 (CH$_2$, C4). Anal. Calc. for C$_{53}$H$_{48}$O$_{10}$ (844.3): C, 75.34; H, 5.73. Found: C, 75.57; H, 5.94.

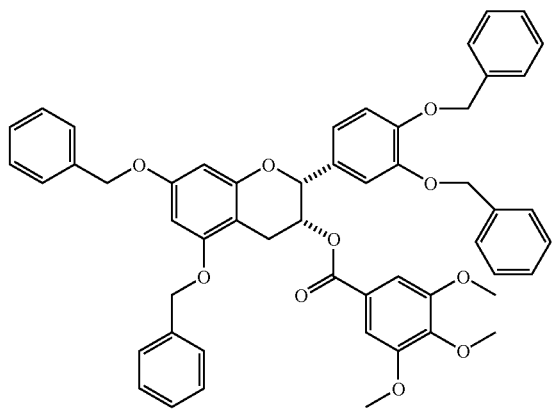 [SMILES: COc1cc(C(=O)O[C@@H]2Cc3c(OCc4ccccc4)cc(OCc4ccccc4)cc3O[C@@H]2c2ccc(OCc3ccccc3)c(OCc3ccccc3)c2)cc(OC)c1OC]

3-O-(3,4,5-trimethoxybenzoyl)-(−)-epicatechin, (6)

Under normal pressure, a solution of 5 (0.600 g, 0.71 mmol) and 10% Pd/C (0.06 g of palladium, 0.56 mmol) in THF/MeOH (1:1, 40 ml) was treated with molecular hydrogen. The solution was stirred for 18 h at room temperature and then filtered on a celite pad which, afterwards, was washed with methanol (300 ml). The solvent was removed under vacuum and the resulting solid was recrystallized from Et$_2$O (yield=62). MS (FAB$^+$) m/z (%) 485 (M$^+$+1, 28). $^1$H NMR (Acetone-d$^6$, 400 MHz) δ 8.31 (bs, 1H, OH), 8.10 (bs, 1H, OH), 7.94 (bs, 1H, OH), 7.80 (bs, 1H, OH), 7.14 (s, 2H, H2" y H6"), 7.11 (d, 1H, $^4J$=2.0 Hz, H2'), 6.90 (dd, 1H, $^3J$=8.2 Hz, $^4J$=2 Hz, H6'), 6.79 (d, 1H, $^3J$=8.2 Hz, H5'), 6.03 (d, 1H, $^4J$=2.2 Hz, H6), 6.02 (d, 1H, $^4J$=2.2 Hz, H8), 5.48 (m, 1H, H3), 5.19 (bs, 1H, H2), 3.80 (s, 6H, OCH$_3$), 3.73 (s, 3H, OCH$_3$), 3.10 (m, 1H, Hgem, H4), 3.05 (m, 1H, Hgem, H4). $^{13}$C NMR (Acetone-d$^6$, 100 MHz) δ 165.9 (q, —COO), 157.9 (q, Ar—O), 157.4 (q, Ar—O), 156.8 (q, Ar—O), 154.0 (q, Ar—O), 145.7 (q, Ar—O), 145.4 (q, Ar—O), 143.3 (q, Ar—O), 131.4 (q, C1'), (126.2 (q, C1"), 118.7 (CH, C6'), 115.6 (CH, C5'), 114.6 (CH, C2'), 107.6 (CH, C2" y C6"), 98.5 (q, C4a), 96.4 (CH, C7), 95.5 (CH, C9), 77.7 (CH, C2), 70.7 (CH, C3), 60.6 (CH$_3$, CH$_3$O), 56.4 (CH$_3$, CH$_3$O), 26.0 (CH$_2$, C4). Anal. Calc. for C$_{25}$H$_{24}$O$_{10}$ (484.1): C, 61.98; H, 4.99. Found: C, 61.69; H, 5.24.

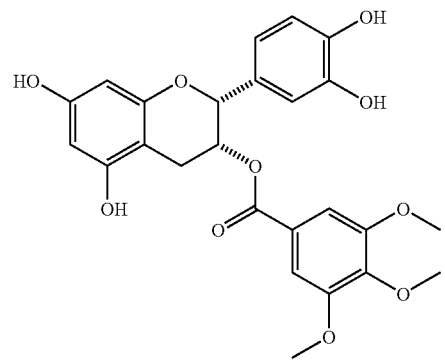 [SMILES: COc1cc(C(=O)O[C@@H]2Cc3c(O)cc(O)cc3O[C@@H]2c2ccc(O)c(O)c2)cc(OC)c1OC]

Cell Culture and Treatments

Four human cancer cells lines (SkMel-28, MCF7, H1264 and Caco-2) were obtained from the American Type Tissue Culture Collection (ATCC) and were maintained in appropriate culture mediums supplemented with 10% fetal calf serum (FCS) and antibiotics, under standard tissue culture conditions (e.g. modified Eagle's medium (MEM) containing 1 mM sodium pyruvate and 10% fetal bovine serum (FES) under 5% CO2/95% air atmosphere.). Cell injury was evaluated by a colorimetric assay for mitochondrial function using the 3-(4,5-dimethylthiazolyl-2)-2,5-diphenyltetrazolium bromide (MTT) cell proliferation assay. For this assay cells were plated in a 96-well plate at a density of 1000 cells/well and grown until they reached 50-60% confluence. Human epidermal melanocytes (HeM) were supplied by Gentaur and were cultured in HAM-F10 medium supplemented with 10% FCS, antibiotics and the human melanocyte growth supplement (Gentaur).

Cell injury was evaluated by a colorimetric assay for mitochondrial function using the 3-(4,5-dimethylthiazolyl-2)-2,5-diphenyltetrazolium bromide (MTT) cell proliferation assay. For this assay cells were plated in a 96-well plate at a density of 1000 cells/well and grown until they reached 30% confluence. Co-treatments of SkMel-28 cells with TMECG and other reagents were carried out by supplementing medium cultures with S-adenosylmethionine (SAM), adenosine or dipyridamole (all from Sigma).

Cellular Uptake of ECG, TMECG and QM

For cellular uptake experiments Caco-2 and SkMel-28 cells were grown until reaching 90% confluence. Then, 20 ml of cellular medium containing 50 μM catechins and 0.2 mM ascorbic acid was added and incubated for 60 h in a CO2 incubator. At specified times 1 ml-aliquots were taken and frozen in liquid N2 until the catechin concentrations were determined by HPLC. Catechins were identified by their characteristic elution times and their concentration calculated with respect to calibration curves of known concentrations of catechins.

Tyrosinase Assays

Human tyrosinase was purified to homogeneity from SkMel-28 (1×108 cells) following the protocol designed by Yurkow and Laskin (1989). TMECG oxidation catalyzed by human tyrosinase was followed using a Perkin-Elmer Lambda-35 spectrophotometer. Steady-state kinetic constants were obtained by measuring the initial rates of TMECG oxidation at 412 nm in 30 mM sodium acetate buffer, pH 5.5 and 25° C.

DHFR Inhibition and Binding Assays

The activity of rHDHFR was determined at 25° C. by following the decrease in the absorbance of NADPH and DHF at 340 nm (ε=11800 M-1 cm−1) (Stone and Morrison, 1986). Progress curves were obtained under ordered conditions ([NADPH]>>[DHF]). rHDHFR inhibition constants were calculated as described by Navarro-Perán et al., 2005b. The dissociation constant for the binding of inhibitors to free rHDHFR was determined at 25° C. by fluorescence titration in an automatic-scanning Perkin-Elmer LS50B spectrofluorimeter. Fluorescence emission spectra were recorded when rHDHFR fluorescence was excited at 290 nm. Stopped-flow fluorescence experiments were carried out using an Applied Photophysics Ltd. Pi-Star 180 spectrometer with a stopped-flow unit at 25° C.

In Silico Molecular Modelling

Molecular modeling was carried out using the CAChe software package for molecular modeling v. 7.5 (Fujitsu). On searching the available ligand-bound human DHFR structures in the Protein Data Bank (PDB) (Berman et al., 2000), we identified a 1.8 Å structure (PDB accession code 1S3V (Cody et al., 2004) containing a tetrahydroquinazoline antifolate ligand ((R)-6-{[methyl-(3,4,5-trimethoxyphenyl) amino]methyl}-5,6,7,8-tetrahydroquinazoline-2,4-diamine; TQD) as the best available structural match for TMECG or QM. Using the position of TQD as a guide, compounds were docked into this protein structure and the inhibitor-protein composite was then energy minimized.

RT-PCR

PolyA+ mRNA from human adult skin was purchased from Invitrogen. SkMel-28 and HEM polyA+ mRNA was extracted from 5×106 cells using the Illustra Quick Prep Micro mRNA purification kit (GE Healthcare). mRNA (200 ng) was used to synthesize cDNA using SuperScript First-Strand Synthesis System (Invitrogen). PCR amplification of 2 µL of the cDNA strand generated was carried out in a total volume of 50 µL using an Eppendorf Mastercycler Thermal Cycler. Samples were amplified by 40 cycles at 95° C. (1 min), 62° C. (1 min) and 72° C. (1 min). The amplified PCR products were subjected to electrophoresis in 3% agarose gel and stained with ethidium bromide.

Primers for PCR

Primers were designer using Primer Express version 2.0 software (Applied Biosystems, Foster City, Calif.) and synthesized by Invitrogen. The sequence of the primers are as follow: MS (forward: 5'-GAGAACCACTCT-ACATTGGA-3'; reverse: 5'-GGAAGA-CCTGCATTGGGATA-3'); AHCY (forward: 5'-TGGACATTGCTGAGAACGAG-3'; reverse: 5'-CTCCACGGTCATGTGCAG-3'); MAT1A (forward: 5'-GTGTGACCACT-CTCTAAGTG; reverse: 5'-TGCCG-GTCTTGCACACTGTCT-3'); MAT2A (forward: 5'-CCAC-GAGGCGTTCATCGAGG-3'; reverse: 5'-CAG-CAGCTCTGGATGTAATT-T-3'); (S+Mb)-COMT (forward: 5'-GAACGAGTCATCCTGCAGCCCATC-3'; reverse: 5'-CTGCTCGCAGTAGGTGTCAA-3'); (Mb)-COMT (forward: 5'-GTCGCG-GGAGAGAAATAACA-3'; reverse: 5'-CTGCTCGCAGTAGGTGTCAA-3'); DNMT1 (forward: 5'-CCCCTGAGCCCTACC-GAAT-3'; reverse: 5'-CTCGCTGGAGTGGAC-TTGTG-3'); GCS (forward: 5'-GGCGATGAGGTGGAATACAT-3'; reverse: TGTCC-TTTCCCCCTTCTCTT-3'); Apaf-1 (forward: 5'-GCTCTC-CAAATTGAAAGGTG-AAC-3'; reverse: 5'-ACTGAAAC-CCAATGCACTCC-3'); and Caspase-3 (forward: 5'-TGGAATTGATGCGTGATGTT-3'; reverse: 5'-GGCAG-GCCTGAATAATGAAA-3'). The primers designed to amplify FRα cDNA were: FR1 (forward: 5'-GGAGGCT-CAGA-CAAGGATTG-3'); FR2 (reverse: 5'-AGGTGTC-CTGGATGAAATGC-3'); FR3 (forward: 5'-AGGAAGAAT-GCCTGCTGTTC-3'); FR4 (reverse: 5'-GGTGTAGGAGGTGC-GACAAT-3'); FR5 (forward: 5'-GTGAGCAATGGTGGGAAGAT-3') and FR6 (reverse: 5'-TCATGGCTGCAGCATAGAAC-3').

Quantitative Real-Time PCR cDNA samples (1 µL) were used for real-time PCR in a total volume of 20 µL using SYBR Green Reagent (Applied Biosystems) and specific primers on a 7500 Real Time PCR System of Applied Biosystems. The PCR amplification cycles included denaturation 95° C., 15 min; to activate Hot-Star Taq DNA polymerase and to minimize primer-dimer contribution), and amplification [over 40-50 cycles including denaturation (94° C.; 30 s), annealing (55° C.; 30 s), and extension (72° C.; 1 min)]. All PCR reactions were performed in triplicate and from at least two independent experiments. Non-RT control and negative control samples (without template) were processed in the same manner. The specificity of the amplification was verified by melting curve analysis for all samples, and occasionally by agarosa gel electrophoresis. Amplification of target gene sequences were compared against serial dilutions of know quantities of their purified cDNA fragments, and normalized to the abundance of the house-keeping gene β-actin.

Caspase-3 Activity Assay

Caspase-3 activity in the SkMel-28 cells was measured using the caspase-3 colorimetric activity assay kit (Sigma). Briefly, the cells were washed with cold PBS and lysed with cell lysis buffer included in the kit. The cell lysates were centrifuged (10,000 g for 5 min at 4° C.), and the supernatants were collected. Equal amounts of protein (100 µg), 30 µg of colorimetric caspase-3 substrate (acetyl-Asp-Glu-Val-Asp p-Nitroanilide; Ac-DVED-pNA) and assay buffer were added to each reaction mix, which were then incubated for 4 h at 37° C. Caspase-3 activity was determined by measuring the absorbance at 405 nm. One unit of caspase-3 activity was expressed as 1 pmol of pNA formed per hour, and its specific activity was that unit divided by micrograms of protein. Caspase-3 inhibitor (Ac-DVED-CHO) was used as negative control.

Western Blot Analysis

Protein lysates were prepared from specified cells, separated by SDS-polyacrylamide gel electrophoresis (PAGE), transferred to nitrocellulose membranes, and analyzed by immunoblotting. Membranes were probed with the following antibodies: anti-DHFR (Sigma), anti-RFC (Santa Cruz Biotechnology) and anti-FRα (Santa Cruz Biotechnology). The membranes were then washed with blocking solution and incubated with secondary antibodies conjugated with horseradish peroxidase. Bound antibodies were detected by chemiluminiscence (ECL Plus, GE Healthcare). Soluble and weakly-bound membrane proteins were extracted with PBS, pH 7.4, containing 1% NP-40, 0.5% sodium deoxycholate and 0.1% SDS. Highly-bound membrane proteins were extracted with 10 mM Tris-HCl, pH 8.0, containing 150 mM NaCl, 2.5 mM EDTA, 60 mM N-octylglucoside and 1% Triton X-100.

Confocal Microscopy

SkMel-28 cells were cultured over 35 mm glass bottom microwell dishes. At zero time the cells were treated with 2 µM MTX-fluorescein (Molecular Probes, Invitrogen) in the absence or the presence of 0.1 mM leucovorin. Preparations were visualized at different times in a Leica TCS 4D confocal scanning laser fluorescence inverted microscope at 750-fold magnification. After 60 min cells were extensively washed with PBS and the internal fluorescence content was visualized. For FRα detection, cells were treated as described elsewhere (Doucette and Stevens, 2004) and incubated with PBS containing primary FRα, antibodies (1:25) followed by incubation (1 h) with PBS containing secondary antibodies (Alexa Fluor Dyes, Invitrogen).

Preparation of Melanoma Cells Granular Fractions and Electron Microscopy

Confluent monolayers of SkMel-28 were harvested with a mixture of 0.05% trypsin, 0.53 mmol/L EDTA and washed once in 0.25 mol/L sucrose by centrifugation at 700×g for 5 min at 4° C. They were then homogenized on ice using 20 strokes of an ice-cold Dounce homogenizer and centrifuged at 700×g for 10 min at 4° C. The resultant postnuclear supernatant was centrifuged at 17,000×g for 15 min at 4° C. to yield a melanosome-enriched granular fraction (17). This fraction was resuspended in 0.5-2 ml of ice-cold 0.25 mol/L sucrose, 10 mmol/L HEPES, pH 7.0 and fixed for 1 h at room temperature in 2% glutaraldehyde, 2% paraformaldehyde in 0.1 mol/L sodium cacodylate buffer, pH 7.3. The fixative was then removed and the samples stored in PBS containing 4% sucrose at 4° C. Samples were subsequently dehydrated with graded alcohols and embedded in epoxy resin. This section were stained with uranyl acetate and lead citrate and examined with a Zeiss EM10 electron microscope.

Mouse Tumor Model

Female C57/B16 mice 6-8 weeks old were obtained from the Animal Research Service (University of Murcia, Spain) and were housed in our animal facilities. All animal work was performed in accordance with the government guidelines. The B16 melanoma cell line (ATCC) was culture in RPMI 1640 medium under standard tissue culture conditions. Mice were shaved on the back using a long-hair cutter and 7.5×10⁵ B16 melanoma cells resuspended in 25 μl sterile PBS were injected intradermally on the back. Animals with tumors more than 8 mm in diameter on day 8 or nonvisible tumor growth by day 12 were excluded. Groups consisting of 20 mice per group were differently treated starting at day 8 after tumor cell injection. For TMECG treatments this compound was uniformly mixed in a cosmetic base cream (Thae, Murcia, Spain). Topical treatment of TMECG was given every day at a dose of ≈1 mg/cm2 skin area. Control mice (non-TMECG treated) were topically treated with the some amount of cream alone. Tumor growth and body weight were monitored every second day. A postmortem with histological examination of the lung, liver and brain was performed in all animals. Tissues were fixed in 10% formaldehyde, dehydrated and embedded in paraffin wax. Sections (4 μm) were stained with eosin and hematoxylin. Analyses of gluconic acid content in lungs were carried out as described elsewhere (Pradeep and Kuttan, 2002).

Results

TMECG is More Effective Against Melanoma Cells

Figure 3:
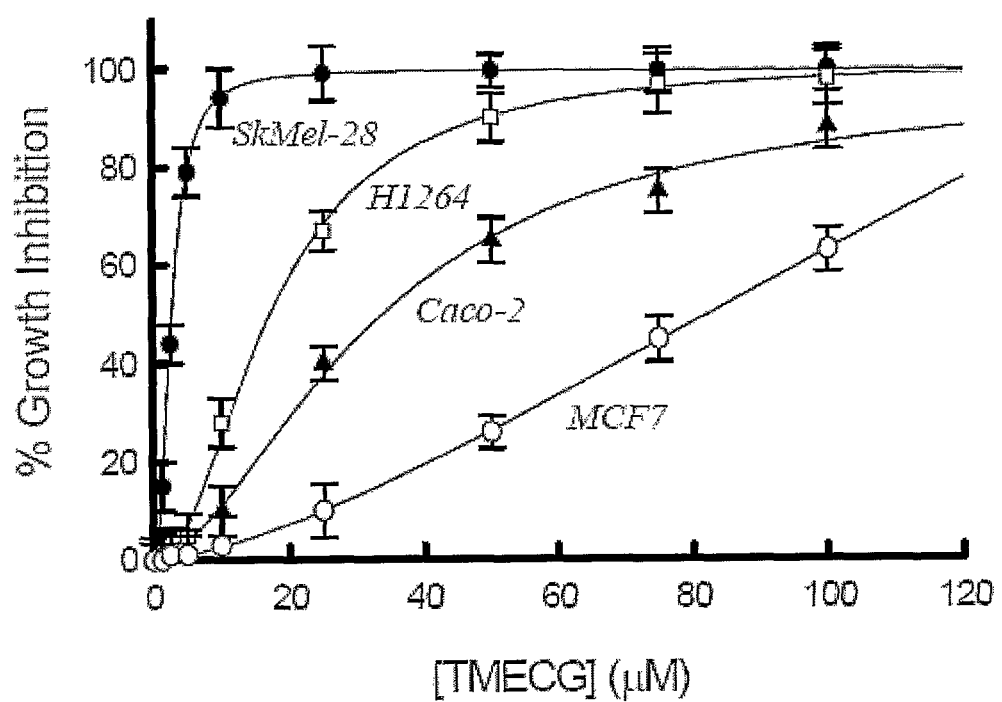
FIG. 3 shows the dose-dependent effect of TMECG on the growth of MCF7, Caco-2, H1264 and SkMel-28 cells after 6 days of treatment compared with untreated cells. The values presented are the mean percentage determined from three independent experiments±SD.
Figure 4:
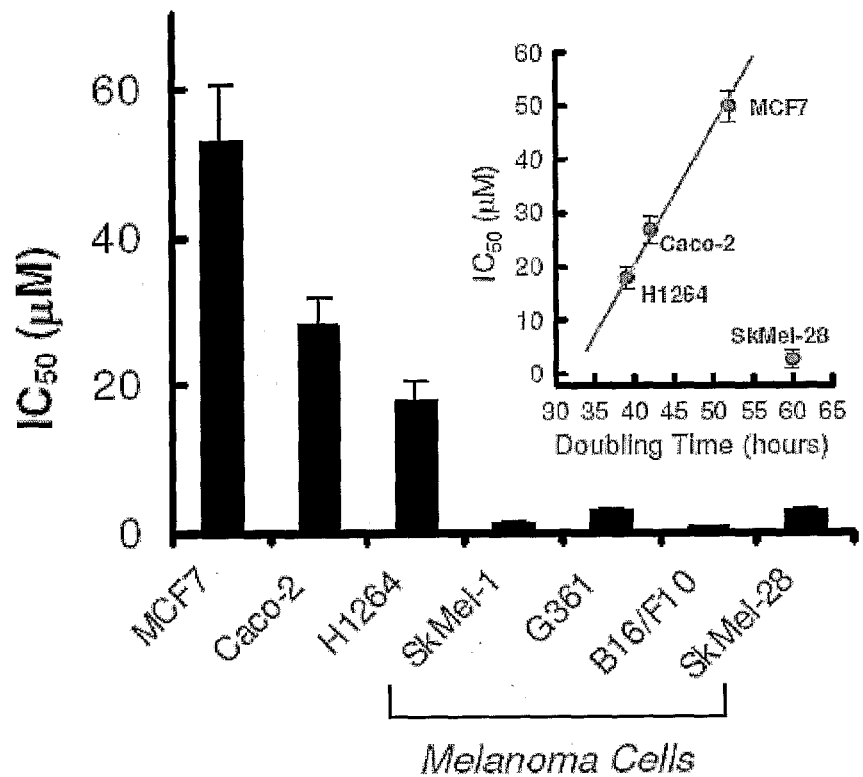
FIG. 4 shows the dependence of TMECG half maximal inhibitory concentration ($IC_{50}$) on cell doubling time.

The antiproliferative activity of TMECG on different human cells was studied using cancer lines from breast (MCF7), lung (H1264), colon (Caco-2) and melanoma (SkMel-28). The effectiveness of TMEG on these cells followed the order SkMel-28>H1264>Caco-2>MCF7 (FIG. 3), with calculated $IC_{50}$-values (at 6 days) of 2.9, 18, 33 and 80 μM, respectively. A linear relationship was observed between the $IC_{50}$ of TMEGC and the doubling time for three of the studied cells; however, TMECG was more active against SkMel-28, which showed the slowest doubling time (FIG. 4). To understand the different degrees of activity of TMECG on these cell systems, we searched for differences in its cellular uptake. Although in all the cell lines tested the transport of TMECG was greater than the uptake of its related natural catechin, ECG, no significant differences were observed in TMECG transport through the membrane of these epithelial cells. A comparison of the transport of TMEGC and ECG into Caco-2 and SkMel-28 cells can be visualized in FIG. 5.

Figure 6:
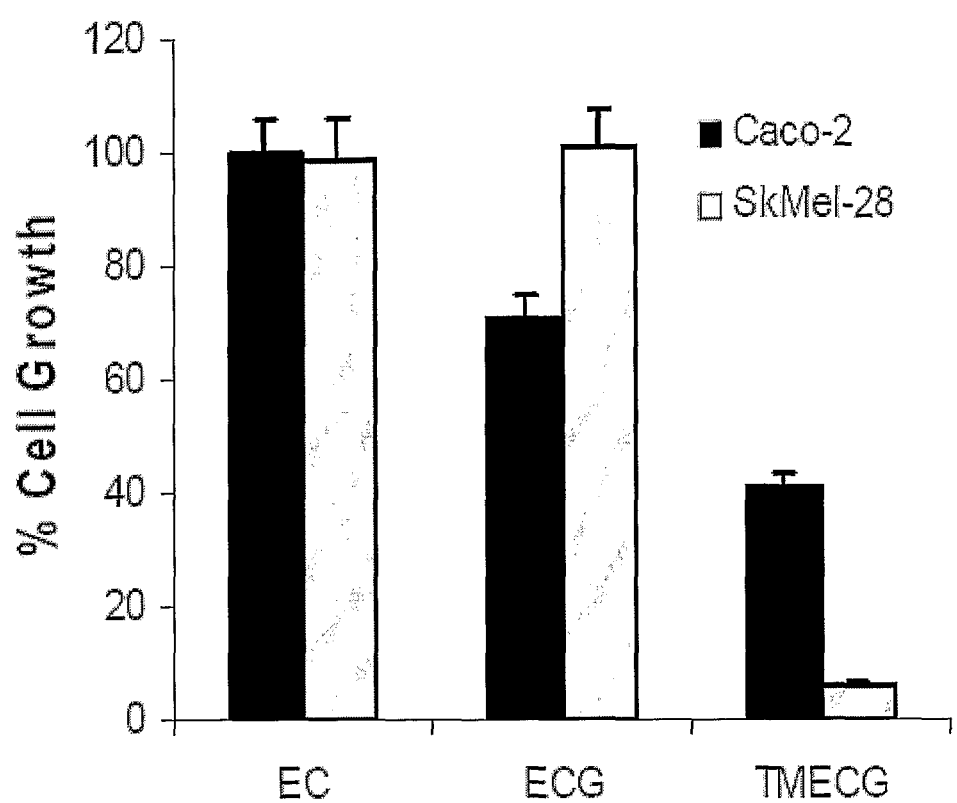
FIG. 6 shows the effect of natural and synthetic catechins on Caco-2 and SkMel-28 growth.

Next, we compared the activity of TMECG with the activity of two natural tea catechins (EC and ECG) using SkMel-28 and Caco-2 cells. EC showed no detectable activity against either cellular systems, while the cell response to ECG and TMECG was different. Caco-2 showed similar sensitivity to both compounds. However, the growth of SkMel-28 was highly inhibited by TMECG but not by ECG (FIG. 6). Many damaged cells were observed after seven days of treatment with 50 μM TMECG. Morphological changes included cell shrinkage, loss of cell-cell contact and the fragmentation of plasmatic and nuclear membranes. However, the only appreciable difference after treatment with 50 μM ECG was the presence of a greater amount of black pigment inside the cells, probably associated with higher melanin content.

A comparison of the results obtained for melanoma and colon cancer cells provided indication that melanoma cells activate TMECG but deactivate ECG. As one of the most appreciable differences between these two cell systems is the presence of tyrosinase in melanoma cells, we further studied whether TMECG cytotoxicity against melanoma cells might be mediated by tyrosinase activation.

TMECG is Activated by Tyrosinase

The role of cellular TYR activation in TMECG cytotoxicity against melanoma was investigated.

Figure 7:
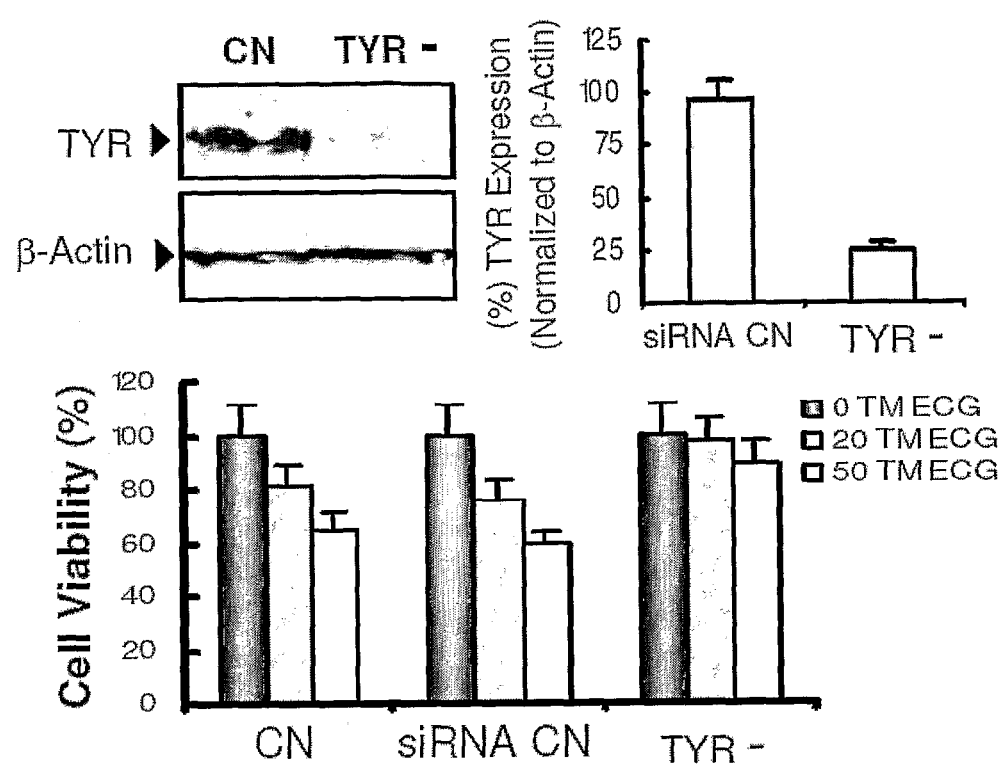
FIG. 7 shows TYR silencing and siRNA prevention of the anti-proliferative action of TMECG (20 and 50 μM) on SkMel-28 cells. Western blot was performed 72 h after siRNA transfection and the percentage of TYR expression was calculated with respect to TYR expression in siRNA-untreated control cells (CN).

First, we silenced TYR expression using siRNA and observed that the anti-proliferative action of TMECG on SkMel-28 cells was mitigated after TYR silencing (FIG. 7).

Second, we delivered TYR into Caco-2 colorectal cancer cells and investigated the ability of this enzyme to enhance the antiproliferative effect of TMECG on this cell line.

Caco-2 cells constitutively express FRα. Folate was conjugated to mushroom TYR using EDC chemistry, and the complex FOL-TYR was used to deliver the enzyme into Caco-2 cells. The efficient uptake of FOL-TYR into Caco-2 cells was confirmed by confocal microscopy and flow cytometry, which compared the internal fluorescence of Caco-2 cells incubated with either fluorescein-labeled FOL-TYR or fluorescein-labeled TYR. The uptake of folate-conjugated TYR was found to be 4.2-fold greater than that of free TYR, providing indication that enhanced endocytosis of FOL-TYR is partially responsible for its greater transport efficacy.

Figure 8:
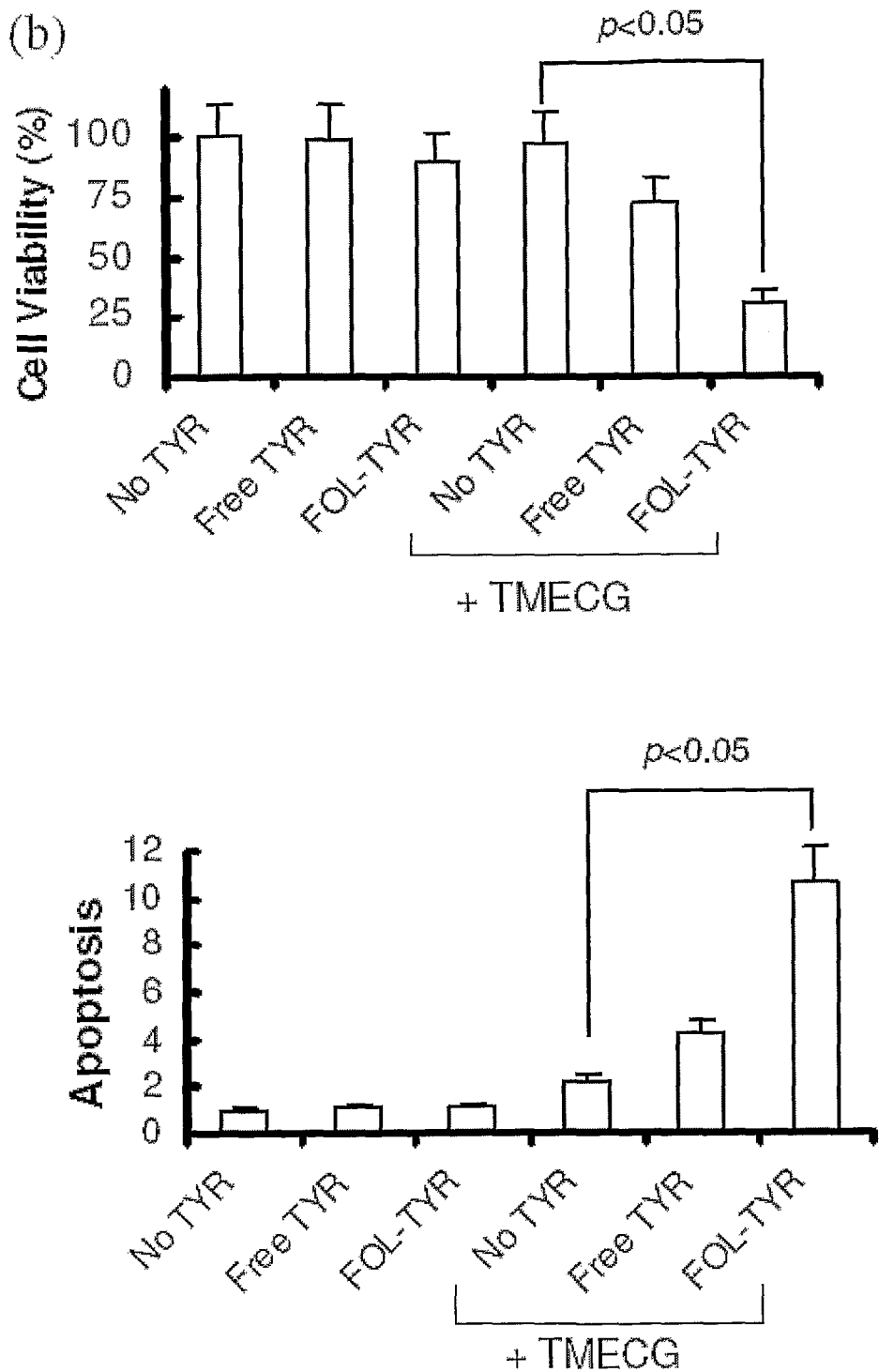
FIG. 8 shows that folate-conjugated TYR efficiently activates TMECG in Caco-2 cells. As demonstrated by the appropriate controls, only the combination of FOL-TYR/TMECG reduced viability (top panel) and induced apoptosis (lower panel) in Caco-2 cells. Significance of the results was determined via the paired t-test between the TMECG-treated cells in the absence of TYR and in the presence of the folate-conjugated enzyme.

The presence of TYR in the cytoplasm of Caco-2 cells strongly enhanced the activity of TMECG, inducing cell growth inhibition (FIG. 8 top panel) and apoptosis (FIG. 8 bottom panel). Together the results indicate that TMECG activation by TYR might explain its greater effects on melanoma cells.

Figure 5:
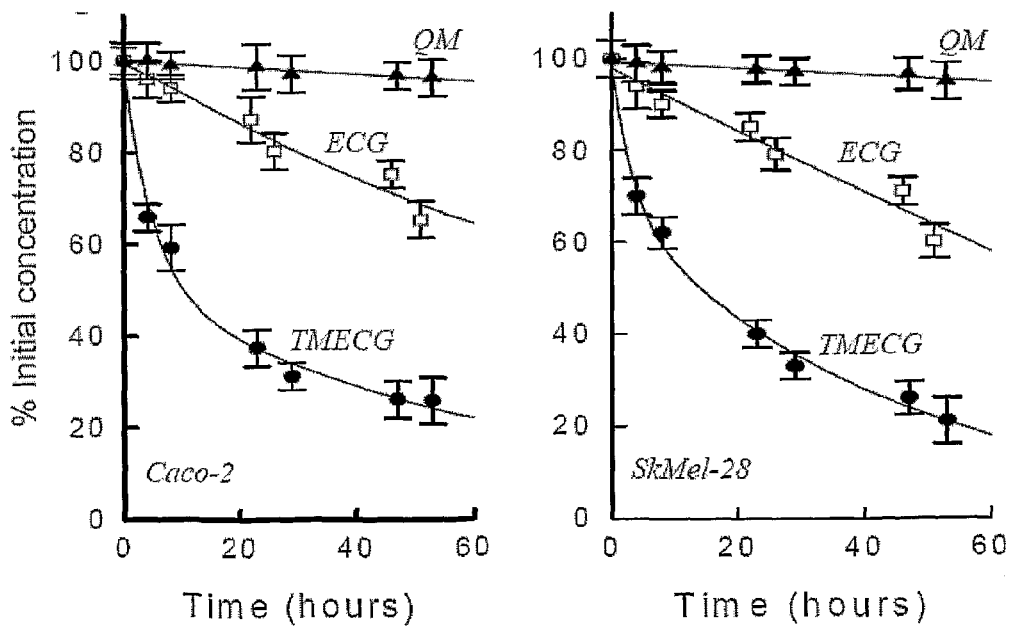
FIG. 5 shows the uptake of ECG, TMECG and QM by Caco-2 and SkMel-28 cells. Cellular uptake was determined by the difference between the initial concentration of catechin and the calculated at specific times in the cellular medium, and expressed as a percentage of catechin at zero time. The values presented are the mean percentage determined from five independent experiments±SD.
Figure 9:
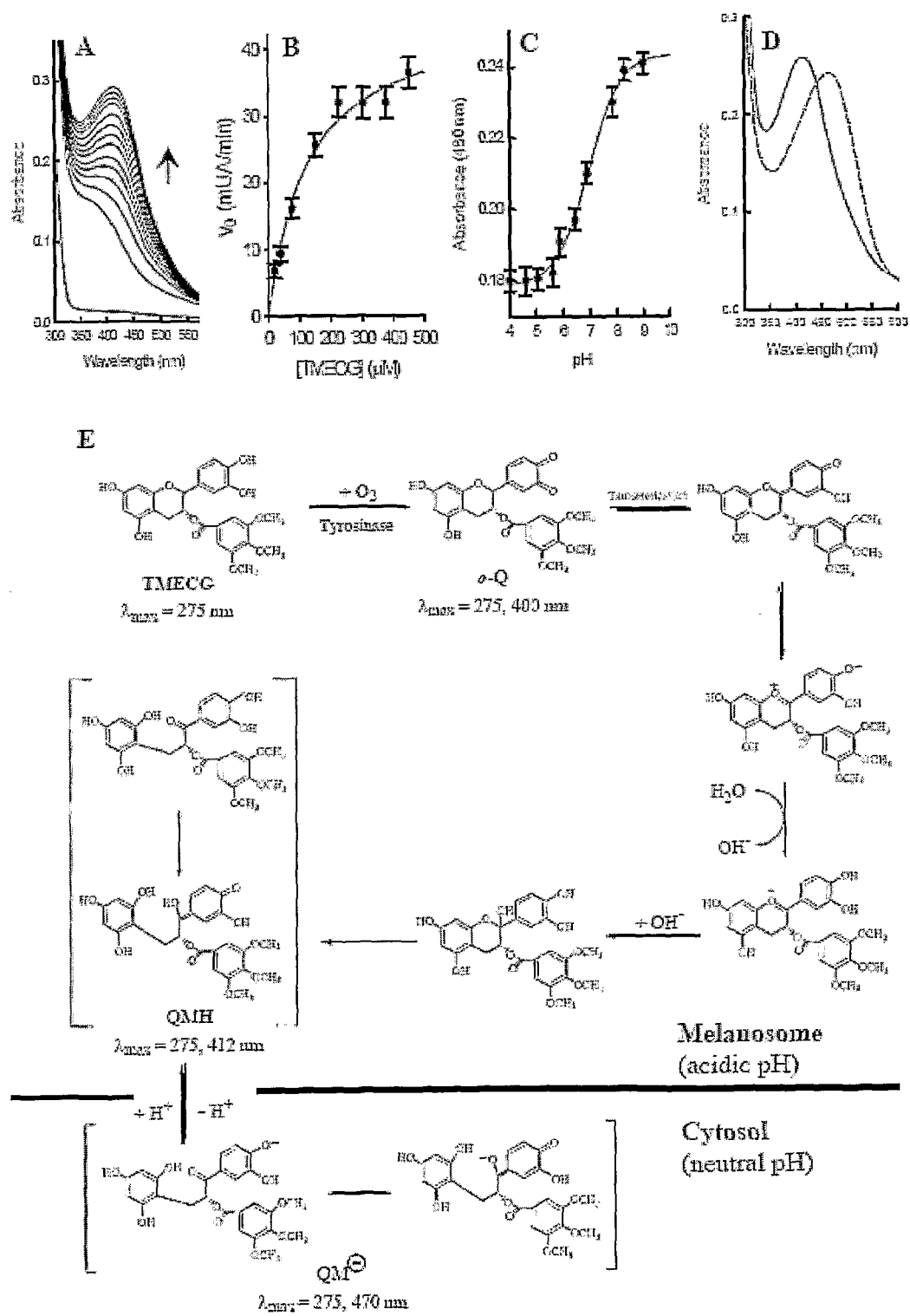
FIG. 9 shows the tyrosinase-catalyzed oxidation of TMECG.

We studied the oxidation of TMECG by tyrosinase at pH 5.5. As can be observed in FIG. 9A, TMECG was efficiently oxidized by human tyrosinase. The Michaelis-Menten constant ($K_m$) for TMECG of the enzyme was 0.12±0.02 mM (FIG. 9B), which was similar to the value reported for L-dopa (0.36 mM) using recombinant human tyrosinase (Kong et al., 2000). It is well known that the primary products obtained from the oxidation of o-diphenols by oxygen catalyzed by tyrosinase are the corresponding o-quinones (Fenoll et al., 2000). The oxidation of TMECG in the presence of oxygen and tyrosinase at pH 5.5 produced an o-quinone (o-Q), which was detected a few seconds after the reaction started. This intermediate ($\lambda_{max}$=400 nm) quickly evolved to a yellowish intermediate with a $\lambda_{max}$ at 412 nm. The initial formation of o-Q was confirmed by including reducing agents such as ascorbic acid or NADPH in the reaction medium. The oxidation of TMEGC by tyrosinase in the presence of ascorbic acid or NADPH involved a lag period proportional to the concentration of reductant, indicating that the o-Q was effectively reduced by these two chemical agents. The final product of the tyrosinase reaction, in contrast, was highly stable and, was not reduced by ascorbic acid or NADPH. The presence of an ionisable group with a pKa of 6.9±0.1 (FIG. 9C) helped us to identify its structure. At basic pH values, its colour changed from yellow to orange with an intense visible band at 470 nm (FIG. 9D). The proposed structure for this compound is depicted in FIG. 9E and was identified as a quinone methide (QM) with an open structure. The pH transition might represent the equilibrium between the protonated form (QMH) and the deprotonated form (QM−), a species which is stabilized by resonance and FIG. 9E represents the possible abundance of QM species in different melanocyte compartments. The anionic nature of this product may also be deduced from its limited degree of cell membrane diffusion (FIG. 5).

QM is an Irreversible Inhibitor of Human DHFR

Figure 10:
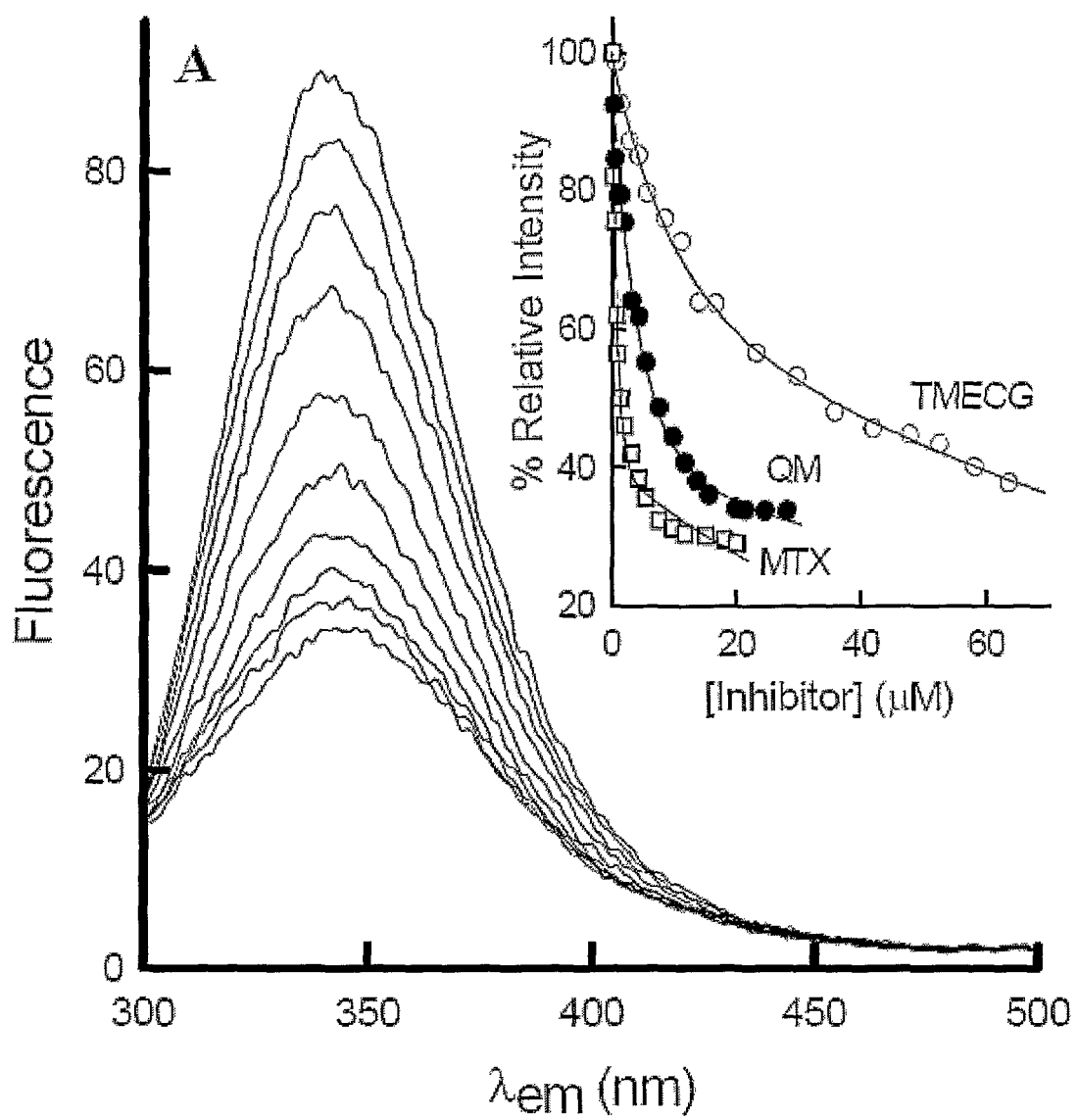
FIG. 10 shows titration fluorescence experiments for the binding of QM to rHDHFR. The experiments were carried out in a buffer containing 2-(N-morpholino)ethanesulfonic acid (Mes, 0.025 M), sodium acetate (0.025 M), tris-(hydroxymethyl)aminomethane (Tris 0.05 M), and NaCl (0.1 M) at pH 7.4 and 25° C. in the presence of QM and rHDHFR (0.5 µM). The inset shows a comparison of the rHDHFR fluorescence quenching by MTX and TMECG in the same assays conditions.
Figure 11:
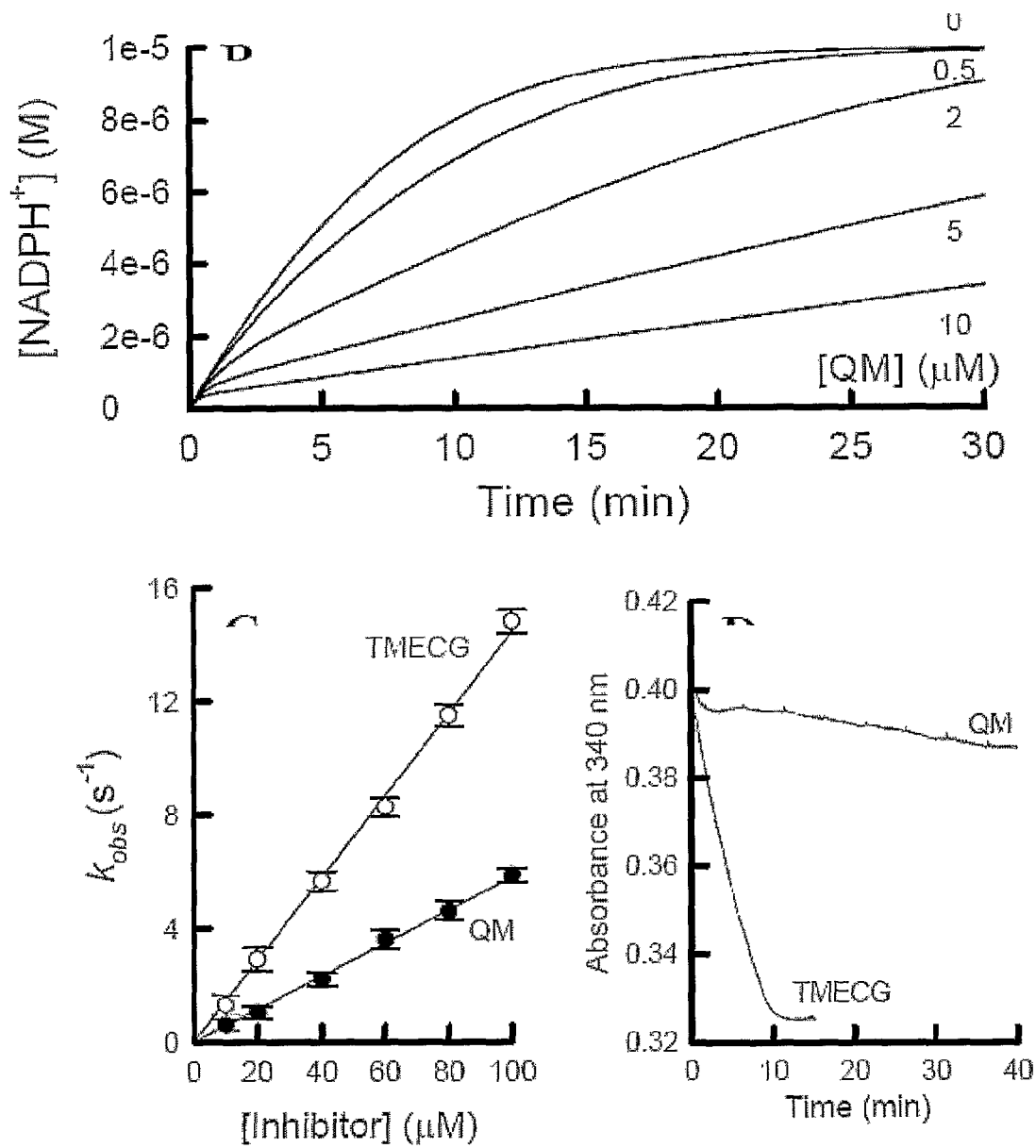
FIG. 11 shows rHDHFR Binding and Inhibition Studies. Top panel shows progress curves for the irreversible inhibition of rHDHFR by QM. The experiments were carried out in the same buffer as fluorescence experiments in the presence of NADPH (100 µM), DHF (10 µM), and rHDHFR (1.5 nM). LH panel shows dependence of the pseudo-first-order rate constant ($k_{obs}$) for the binding of TMECG and QM to rHDHFR on inhibitor concentration. Stopped-flow fluorescence experiments were carried out at pH 7.4 and 25° C. using an enzyme concentration of 0.25 µM. The reaction of rHDHFR with inhibitors was observed under pseudo-first order conditions by fluorescence at 340 nm (excitation at 290 nm). The data points s are the means of at least 3 (normally 5) repeat observations±SD. RH panel shows progress curves for the recovery of the rHDHFR activity after preincubation with TMECG or QM. rHDHFR (75 nM) was preincubated for 30 min at 25° C. in the buffer medium containing 10 µM inhibitors. Aliquots (20 µl) of the incubation mixture was then diluted 50-fold into a reaction mixture containing the buffer, NADPH (100 µM), and DHF (10 µM) to give a final enzyme concentration of 1.5 nM.

The synthetic catechin, TMECG, inhibited rHDHFR with an effective inhibition constant ($K_I^*$) of 0.11 μM (Table 1). Mushroom tyrosinase was used to synthesize the QM and its affinity by rHDHFR at pH 7.4 was assayed employing fluorescence quenching (FIG. 10). When rHDHFR fluorescence is excited at 290 nm its emission spectrum shows a maximum at 340-350 nm. The binding of QM quenched this fluorescence and the data showed a dissociation constant ($K_I$) of 8.2±0.11 nM. Compared with other inhibitors of rHDHFR, QM showed intermediate affinity between MTX and catechins; thus, QM bound more than two-order of magnitude more strongly than EGCG, ECG or TMECG but forty-times less than MTX (Table 1). When the activity was continuously assayed after addition of the enzyme to assay mixtures containing QM and enzyme substrates (NADPH and DHF), the resulting progress curves were representative of irreversible inhibition (FIG. 10) (Navarro-Martinez et al., 2007). The binding of TMECG and QM to free enzyme was investigated at pH 7.4 using stopped-flow fluorescence kinetics. Under pseudo first-order conditions the apparent rate of reaction increased linearly with inhibitor concentration and showed no evidence of saturation at higher concentrations (FIG. 10). Assuming a simple association step the observed rate ($k_{obs}$) can be approximated by the relationship, $k_{obs}=k_{on}[I]+k_{off}$, where $k_{on}$ and $k_{off}$ are the rate constants for the association and dissociation, respectively. Thus, a plot of $k_{obs}$ against [I] gave a straight line of slope $k_{on}$ and intercept $k_{off}$ (FIG. 11 LH panel). Following this scheme, the second-order rate constants for the reaction of rHDHFR with TMECG or QM were obtained (Table 1). In each of these experiments, the intercept value of $k_{off}$ was too small to be measured, although it could be calculated from the $K_I$ expression ($K_I=k_{off}/k_{on}$) (Table 1). As can be observed in this table, the association constants of rHDHFR for TMECG and QM are in the some order but the first-order rate constant for the dissociation of QM to the free enzyme is around 3-order of magnitude lower than for TMECG, which makes the binding of QM to rHDHFR essentially irreversible. Further evidence for this irreversibility was obtained by comparing the results of adding aliquots of preincubation mixtures of rHDHFR with QM or TMECG to assay mixtures containing substrates (FIG. 11 RH panel). This high irreversibility in the binding of QM to rHDHFR also conditioned its action mechanism, which differed from the other assayed compound. MTX and tea catechins act as slow-binding inhibitors of rHDHFR (Appleman et al., 1998; Navarro-Perán et al., 2005a) and so the overall inhibition constant ($K_I^*$) is decreased by further EI-complex reactions (Table 1).

Molecular Modelling Experiments Explains the Irreversible Binding of QM to Human DHFR We performed in silico molecular modelling experiments to explain the high irreversibility on the binding of QM to rHDHFR. TMECG bound to human DHFR in a similar way to that described for EGCG (Navarro-Perán et al., 2005a), with specific hydrogen bonding interactions, most notably involving Glu-30. However, the open structure of the QM increases its molecular flexibility and adopts a different conformation in the active site of human DHFR. QM maintained the hydrogen bond with Glu-30 sidechain (O . . . O distance 1.99 Å), but three new interactions were detected. Thus, the other phenolic group of the ring A of QH forms a hydrogen bond with Ile-7, whereas the other two hydrogen bonds were formed between two oxygens of the methoxy groups of ring D and Ser-59 and Ile-60. This strong interaction between QM and different residues of the protein explains the high irreversibility of the inhibitor-protein complex.

TMECG modulates SkMel-28 Folate Transport

Figure 12:
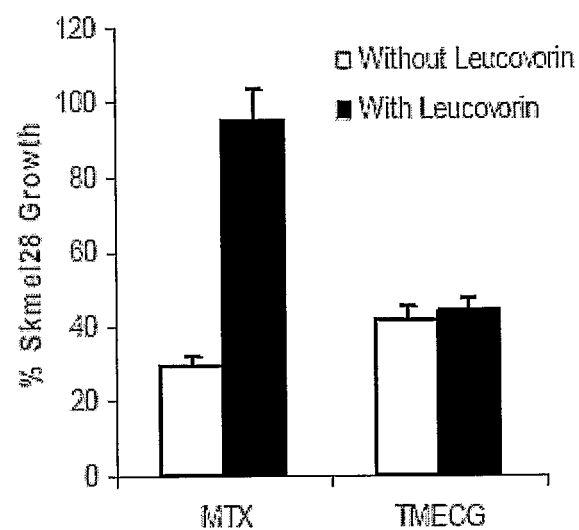
FIG. 12 shows the effect of leucovorin (0.1 mM) on the growth inhibition of SkMel-28 melanoma cells by MTX (1 µM) and TMECG (50 µM) after 3 days of treatment, assuming 100% growth for the untreated control. Bars represent the average for three individual experiments±SD.

Further experiments were performed to show the antifolate activity of QM in culture systems. Antifolates block the de novo biosynthesis of thymine, purines and pyrimidines by inhibiting the synthesis of THF, an essential cofactor in these biosynthetic pathways. Administration of exogenous reduced folates, such as leucovorin, effectively prevents antifolate cytotoxicity in mammalian cells. When SkMel-28 cells were treated with 1 μM MTX for 3-days, their growth was inhibited by 70% and co-treatment with 100 μM leucovorin effectively reversed this inhibition (FIG. 12). However, leucovorin did not "rescue" SkMel-28 cells from TMECG-induced death (FIG. 12).

Figure 13:
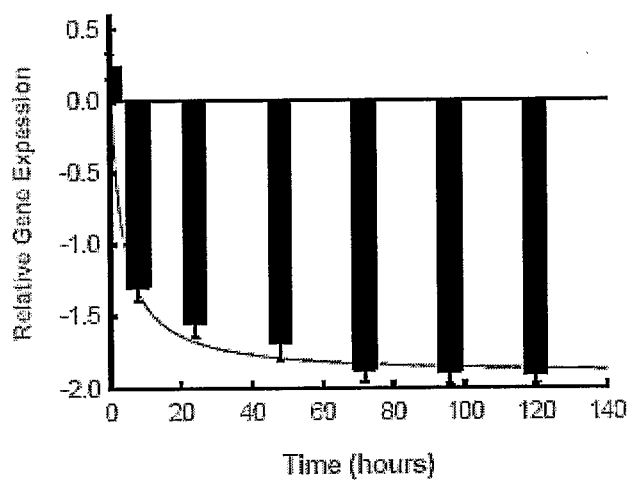
FIG. 13 shows time dependence expression of RFC in SkMel-28 cells treated with 50 µM TMECG. Data were obtained by real time PCR and compared with the relative expression of RFC in normal human skin (zero relative gene expression). Zero time represents the level of RFC in untreated SkMel-28 cells. Differences between different times were statistically significant (P<0.001)

To understand the different response of SkMel-28 to leucovorin-combined treatments and to prove the in vivo antifolate activity of TMECG, the status of folate transporters in this cell line was analyzed. Reduced folate carrier (RFC) mRNA expression was slightly but significantly higher in SkMel-28 than in human adult skin or HeM cells (3.2- and 6.5-fold higher, respectively). Treating SkMel-28 with 50 μM TMECG for 72 h strongly down-regulated RFC gene expression. The level of down-regulation of RFC mRNA ranged from 1200 to 2100-fold the mean of non-treated SkMel-28 cells. Protein levels of this transporter correlated with gene expression. The time-dependent effect of TMECG on SkMel-28 was studied using real-time PCR (FIG. 13), and the data indicated that cells responded quickly to TMECG treatment with a more than 80% reduction in RFC expression after 24 h of treatment.

Figure 14:
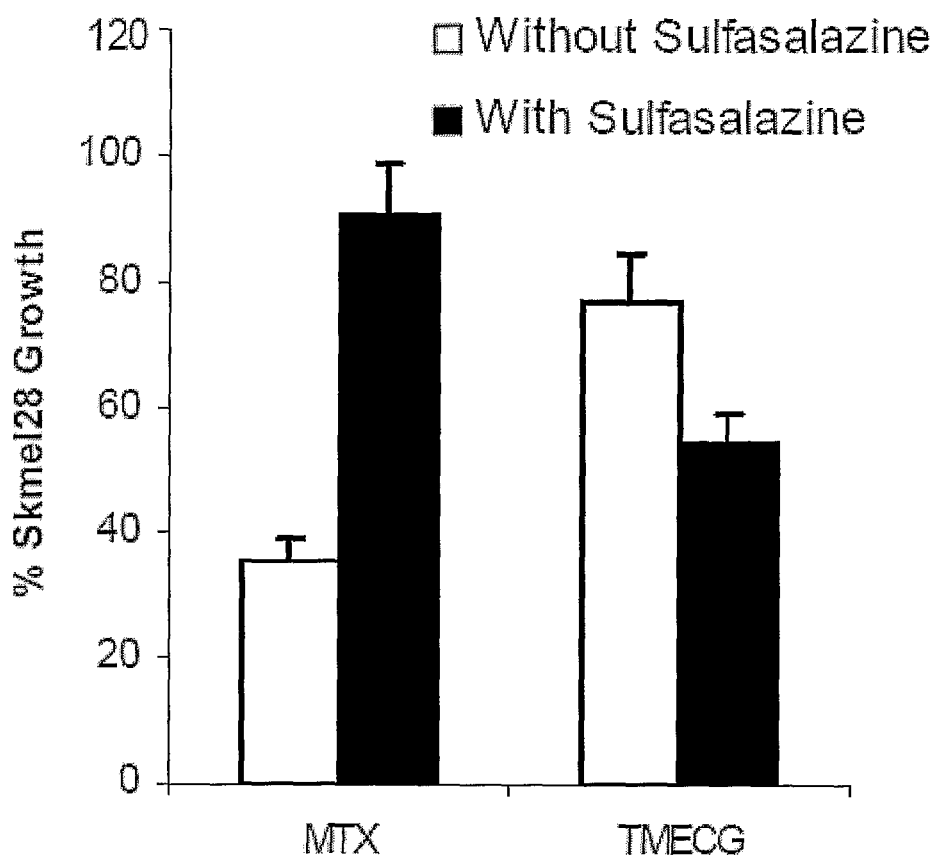
FIG. 14 shows the effect of sulfasalazine (0.5 mM) on the growth inhibition of SkMel-28 melanoma cells by MTX (0.2 µM) and TMECG (10 µM) after 3 days of treatment, assuming 100% growth for the untreated control. Bars represent the average for three individual experiments±SD.

Although TMECG efficiently binds to DHFR, we hypothesized that this hydrophobic compound crosses the cell membrane by a gradient of concentration without needing bind to folate transporters. To demonstrate this, SkMel-28 was incubated with MTX or TMECG in the presence of different concentrations of sulfasalazine, a potent inhibitor of the RFC (Jansen et al., 2004). As can be observed in FIG. 14, sulfasalazine differentially modulated the action of MTX and TMECG. Sulfasalazine inhibited the antiproliferative action of MTX, indicating that both compounds competed for the RFC. However, in the presence of TMECG, sulfasalazine showed an opposite effect, enhancing TMECG antiproliferative activity. This finding explains why leucovorin does not affect the TMECG treatment. As demonstrated above, TMECG highly down-regulated the RFC and, therefore, leucovorin cannot enter into the cells during TMECG treatment and can not, therefore, restore the reduced folate levels in the cells. We also demonstrated that in addition to restoring the folate pool in the cells, leucovorin can also reverse the action of MTX through competition with RFC.

Figure 15:
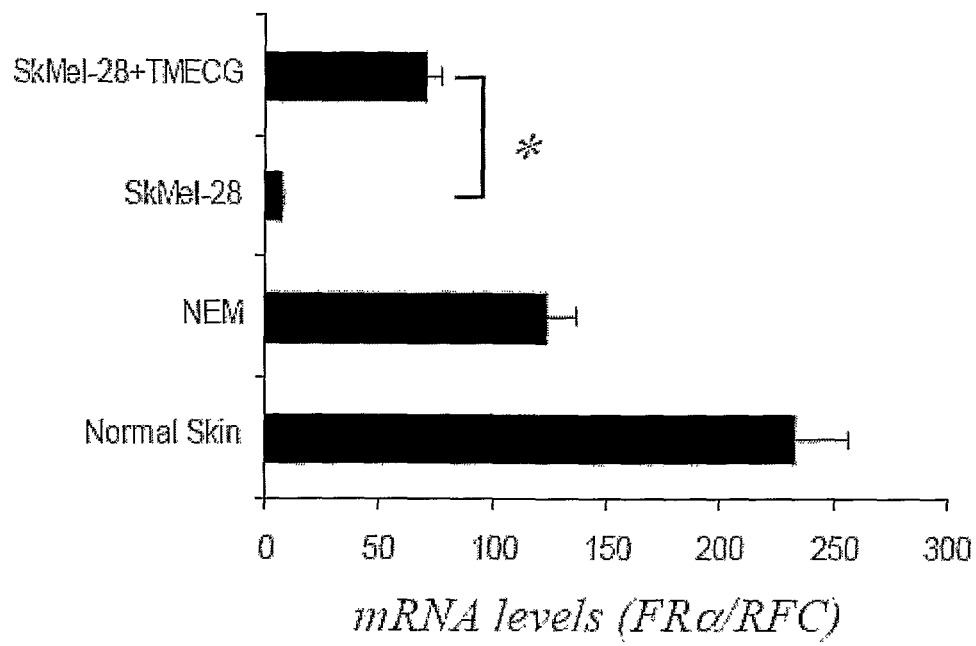
FIG. 15 shows the ratio of FRα versus RFC mRNA levels in different cells and tissues.
Figure 16:
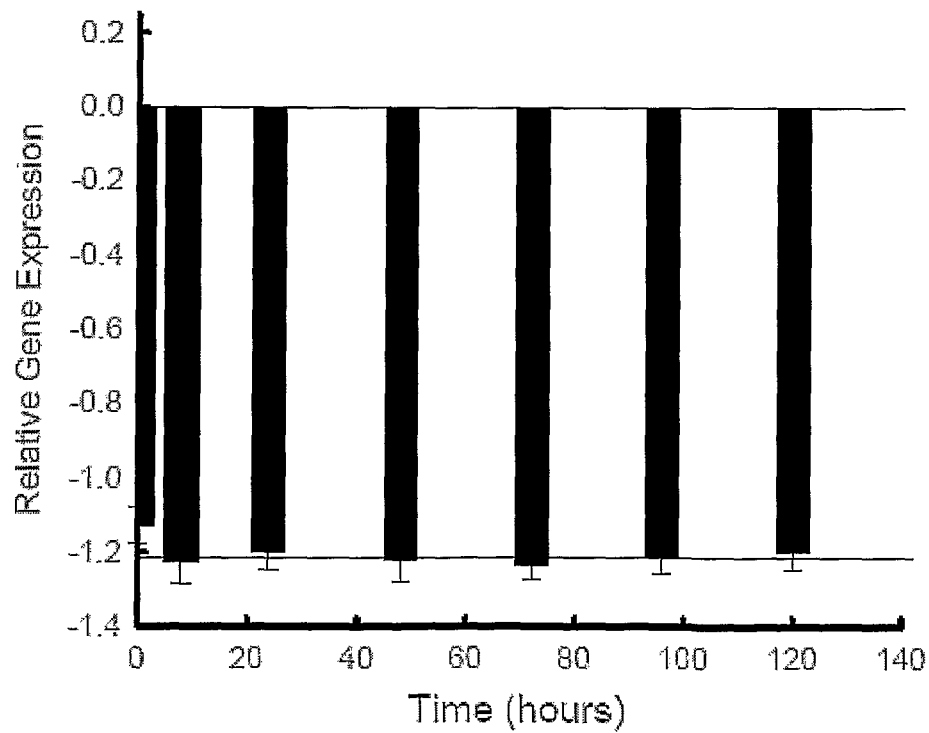
FIG. 16 shows the time dependence expression of FRα in SkMel-28 cells treated with 50 µM TMECG. Data were obtained by real time PCR and compared with the relative expression of FRα in human adult skin (zero relative gene expression). Zero time represents the level of FRα in untreated SkMel-28 cells.
Figure 17:
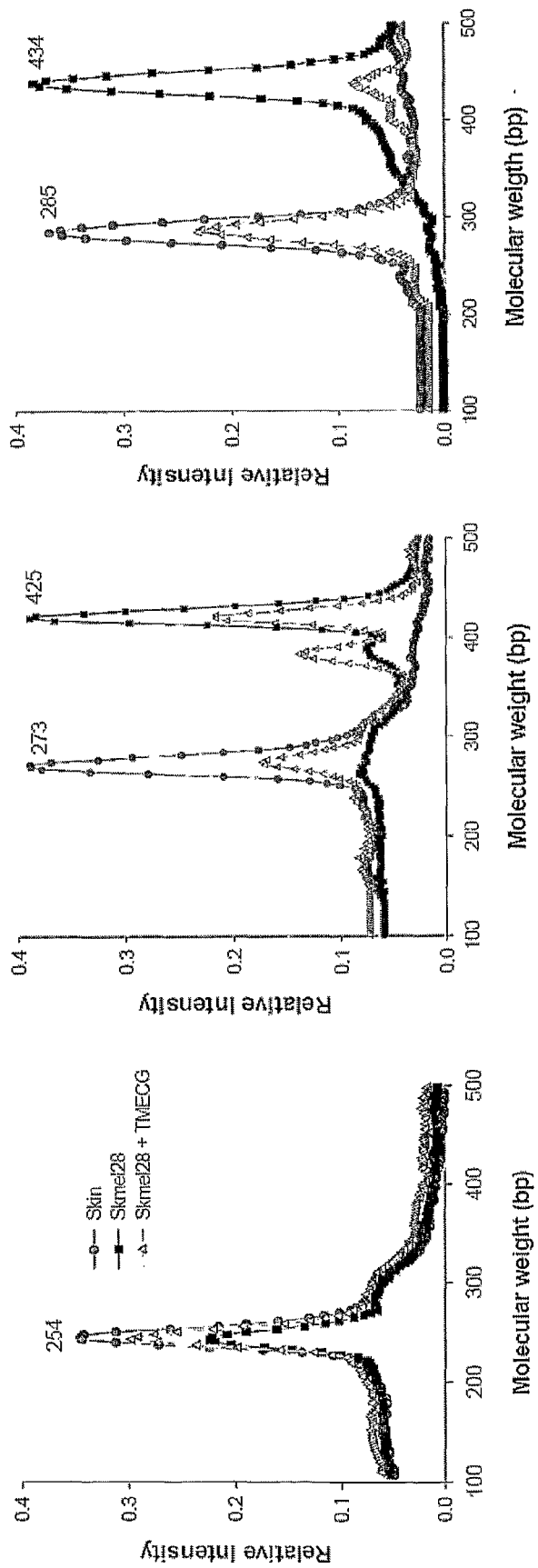
FIG. 17 shows RT-PCR analysis of native and alternative spliced FRα in normal human skin (circles), SkMel-28 (square) and SkMel-28 treated with 50 µM TMECG during 3 days (triangle). The observed PCR products of 254, 273 and 285 represent the native, while the 425 and 434 represent the alternative splicing.
Figure 18:
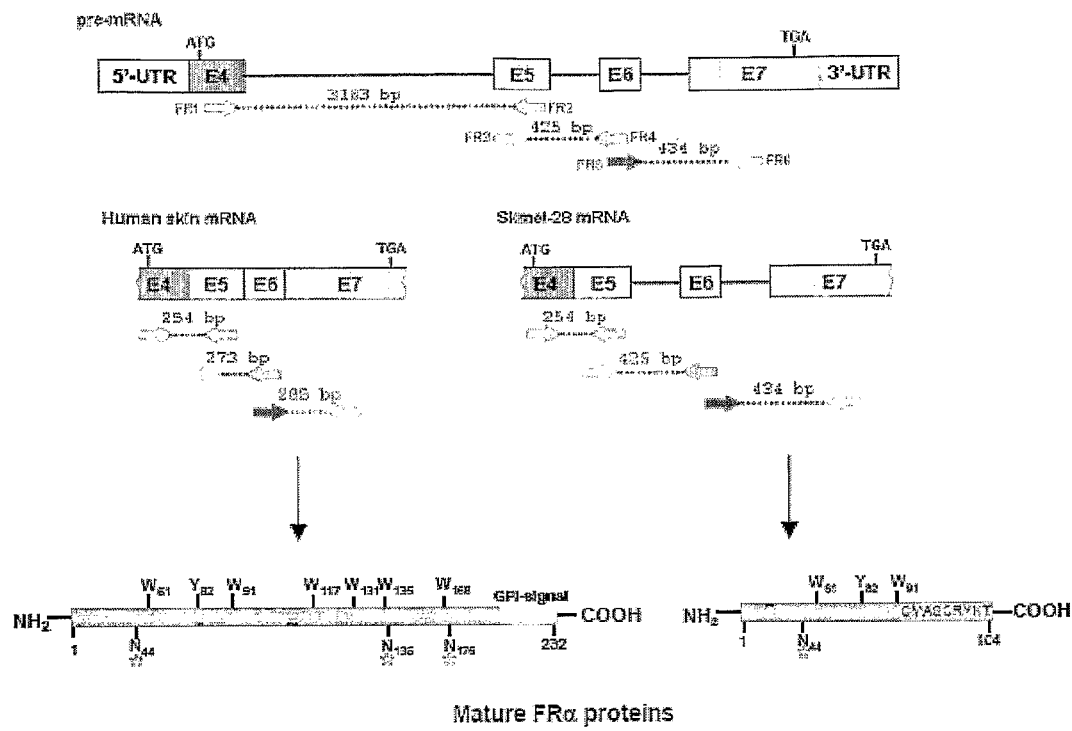
FIG. 18 shows a schematic representation for the alternative splicing of FRα in human melanocytic cells. FRα gene is composed of 7 exons; exons 1 through 4 encode the 5' UTR and exons 4 through 7 encode the open reading frame. The scheme also represents the mature mRNA detected in human normal skin and the alternatively spliced mRNA presented in SkMel-28. Normal mature FRα protein and that deduced from the alternative splicing are also shown. Tryptophan and tyrosine residues important for folate binding (Maziarz et al., 1999) and N-liked glycosylation sites (*) are also represented.

Although the mRNA level of the folate receptor-α (FRα) with respect to RFC was highly dependent on the type of tissue/cell and treatment (FIG. 15), a complex situation was observed when FRα expression was studied. First, two primers were synthesized to amplify an internal region (109 bp) of FRα exon 5, and the level of expression of this receptor was studied by real-time PCR (FIG. 16). It is well-known that FRα expression is limited to normal differentiated epithelial cells (Weitman et al., 1992) and by using polyA+ mRNA from human adult skin, we detected, as expected, an amplified band after RT-PCR amplification. However, the levels of expression of FRα were much lower in SkMel-28 cells and no apparent effect on its expression was observed after 5 days of treatment with TMECG (FIG. 16). These data did not correlate with Western blot experiments designed to detect protein levels in these cells (see above). To understand the situation of this receptor in SkMel-28 cells, we designed 3 pairs of primers (FR1 to FR6), which amplify most of the open reading region of FRα mRNA and which included the complete intron sequences between exons 4/5, 5/6 and 6/7 of its pre-mRNA. Amplification of normal skin cDNA with these primers produced the expected fragments of 254, 273 and 285 bp (FIG. 17), corresponding to mature FRα mRNA. Amplification of SkMel-28 cDNA with primers FR1/FR2 produced the expected band at 254 bp, while higher bands at 425 and 434 bp were observed when the pairs FR3/FR4 and FR5/FR6, respectively, were used for the PCR reaction (FIG. 18). Sequencing of the 425 and 434 bp fragments showed 100% concordance with the corresponding pre-mRNA amplified regions of FRα. The data provide indication of an alternative splicing of FRα in SkMel-28 cells (Scheme 2). Treatment of this melanoma cell line with TMECG for 3 days partially restored the levels of mature FRα mRNA to the cells. As a consequence of the alternative splicing of FRα mRNA in SkMel-28 we were able to observe an alteration in the cellular distribution of this receptor. After extraction of soluble and tightly membrane bond proteins, samples were analyzed by Western blot analysis. Soluble FRα was detected in SkMel-28 but not in normal skin melanocytes. In contrast, solubilization of highly bond membrane proteins with appropriate detergents yielded a elevate membrane FRα fraction in normal melanocytes, which was absent in SkMel-28 cells. Soluble and membrane bound proteins differed in their respective molecular weigh. Treatment of SkMel-28 with TMECG produced an intermediate situation in which the soluble form is decreases and the membrane bound form increases with respect to untreated cells. Confocal studies also revealed that FRα is maintained intracellularly in SkMel-28, while a vast part of the receptor is associated to the plasmatic membrane in SkMel-28 after treatment with TMEGC, as was observed in normal melanocyte cells. The results obtained here concerning folate transport could also be of importance for understanding the poorly understand function of FRα (Kelemen, 2006) and the strong resistance of melanoma cells to classical antifolates (Kufe et al., 1980).

TMECG Efficiently Down-regulates DHFR Expression

Figure 19:
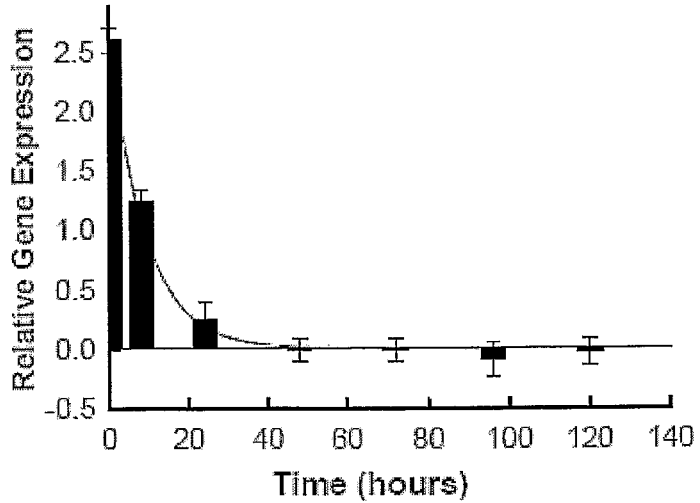
FIG. 19 shows time dependence expression of DHFR in SkMel-28 cells treated with 50 µM TMECG. Data were obtained by real time PCR and compared with the relative expression of DHFR in HeM cells (zero relative gene expression). Zero time represents the level of DHFR in untreated SkMel-28 cells. Differences between different times were statistically significant (P<0.025).

As described for several melanoma tumors and cell lines (Kufe et al., 1980), DHFR is overexpressed in SkMel-28 cells. The level of DHFR polyA+ mRNA in this cancer cell line was estimated as 400-500-fold higher than in the normal melanocyte line HeM, an increase which results in an increased content of DHFR protein. Treatment of SkMel-28 with TMECG rapidly reduced DHFR mRNA and protein to normal levels (FIG. 19). The efficient down-regulation of DHFR by TMECG supports its antifolate activity and provides indication that a deficit in folate coenzymes is responsible for the in vivo activity of this compound.

TMEGC Inhibits Growth and Metastasis of Induced Melanoma Tumors in Mice

Figure 20:
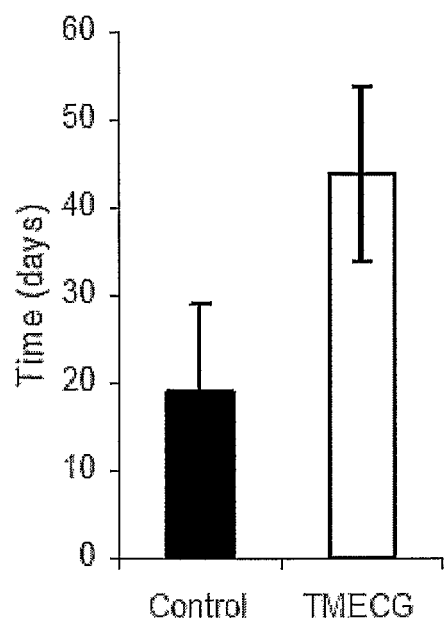
FIG. 20 shows the median survival time of C57/B16 mice bearing the B16 melanoma.
Figure 21:
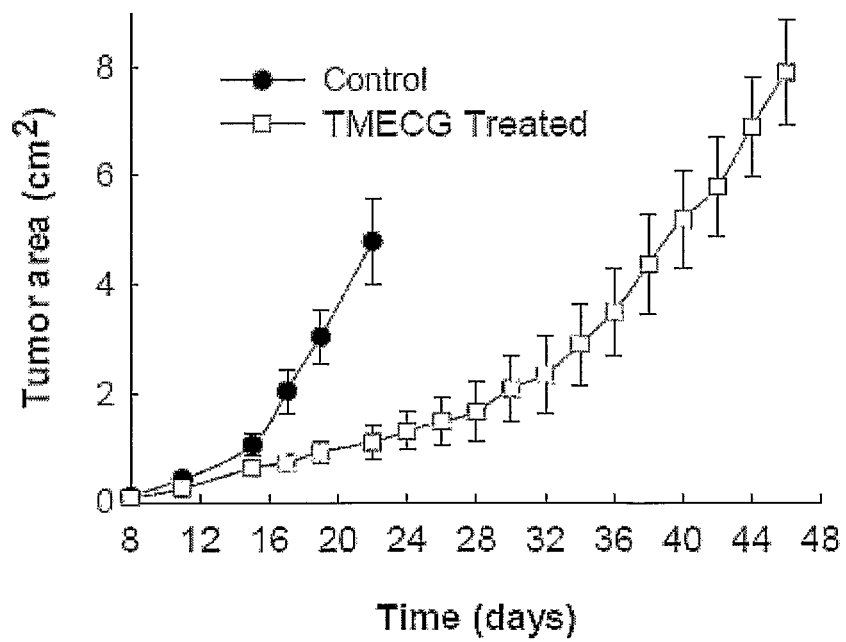
FIG. 21 shows mean tumor size in C57/B16 mice bearing the B16 melanoma. Analysis was stopped when the number of survivors dropped below five per group. The difference at day 21 was significant (P<0.02).
Figure 22:
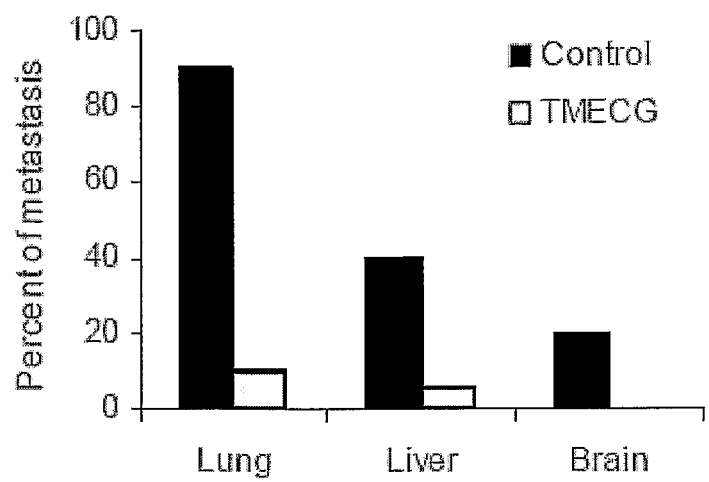
FIG. 22 shows the rate of metastasis in post-mortem and histological examination of lung, liver, and brain of C57/B16 mice bearing the B16 melanoma.
Figure 23:
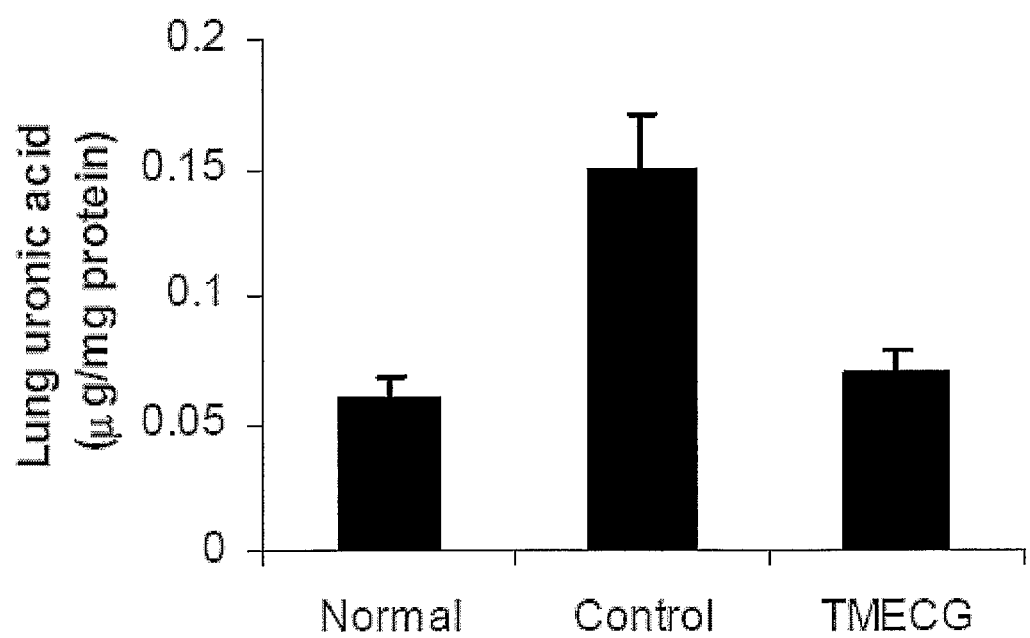
FIG. 23 shows the effect of TMECG on the lung uronic acid levels of tumor-bearing animals. Animals were sacrificed on the 21st day and their lungs were excised. Normal lung was from animals not bearing B16 melanoma. The results are expressed as the mean±SD of three separate experiments. The data are representative of duplicate activity determinations. *P<0.001, significantly different from normal group and **P<0.005, significantly different from untreated group.

The effectiveness of TMECG in induced melanoma tumors in mice was determined. The group receiving TMECG therapy showed longer survival time with the difference between the mean survival times of the treated, group and control being significant (FIG. 20). Tumor growth was significantly reduced by the treatment with TMECG (FIG. 21). TMECG treated animals survived with bigger tumors, indicating that treatment could reduce the metastasis of primary tumors. To confirm this, a third group was inoculated with B16 melanoma cells and treated with TMECG for 21 days (median survival of the control group). After this time the animals were sacrificed and a post-mortem examination was performed, comparing the findings with those for untreated controls. Liver, lung and brain were searched for metastatic lesions semi-quantitively. As can be observed from FIG. 22, secondary metastasis was more frequent in the lung of control mice but treatment with TMECG drastically reduced lung metastasis. The appearance of representative lungs and histological sections from control and treated animals was observed. The lungs of the control animals showed prominent tumor nodules around the terminal bronchiole. These tumor nodules were composed of polygonal tumor cells with a prominent nucleolus. Intracellular melanin deposition and a clear area of necrosis were also present. The lungs of the TMECG-treated tumor-bearing animals showed no significant tumor mass. The alveoli and pleura were tumor free, and the alveolar passage was lined with healthy ciliated columnar epithelial cells. Evident liver and brain metastasis was observed in only 30% and 5%, respectively, of the control mice, whereas no metastasis in these organs was detected in mice receiving TMECG therapy. Finally to demonstrate, from a molecular point of view, the reduction of secondary metastasis in the lungs of treated animals, the uronic acid content of lung (Pradeep and Kuttan, 2002) was compared with its content in untreated mice and those not receiving B16 melanoma injection (FIG. 23). The results indicated that uronic acid in treated mice was similar to that observed in non-inoculated mice but much lower that the content found in the untreated controls.

The Methionine Cycle in Melanoma Cells

Figure 24:
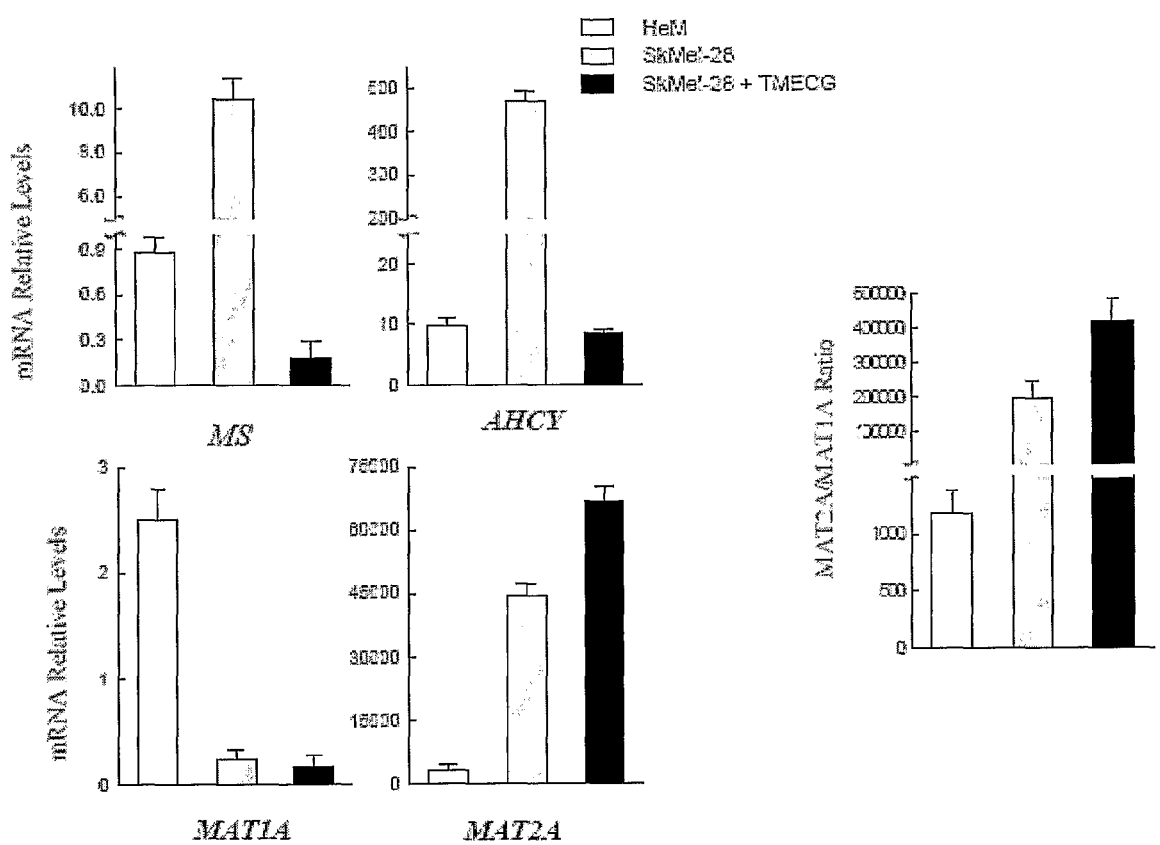
FIG. 24 shows a semi quantitative determination of MS, AHCY and MATs mRNAs. Histograms compare the estimated relative levels of the mRNA with respect to that of β-actin. Values represent the number of copies of mRNA per each $1\times10^6$ copies of β-actin.

The synthesis of methionine is catalyzed mainly by MS or by betaine homocysteine methyltransferase (FIG. 2). Whereas MS occurs in all mammalian tissues, betaine enzyme is mainly present in the liver. The levels of expression of MS mRNA in non-pathological human epithelial melanocytes (HeM) and in the melanoma SkMel-28 cell line were analyzed by real time PCR (FIG. 24). SkMel-28 showed a much higher content of MS mRNA (FIG. 24). Other genes of the methionine cycle including MAT2A and AHYC were also found highly over-expressed in melanoma when compared with normal melanocytes (FIG. 24). However, MAT1A, which was detected in skin cells, showed an opposite behavior being highly down-regulated in SkMel-28 cells. The mRNA ratio MAT2A/MAT1A was found highly increased in melanoma cells when compared with normal melanocytes (FIG. 24).

MAT is an essential cellular enzyme that catalyzes the formation of SAM, the principal biological methyl donor and the ultimate source of the propylamine moiety used in polyamine biosynthesis (Mato et al., 1997). MAT is the product of two different genes, MAT1A and MAT2A, which code for two different enzymes, MATI/III and MATII respectively, with distinct kinetic and regulatory properties and that display a tissue-specific pattern of expression (Garcia-Trevijano et al., 2000). MAT1A is expressed mostly in liver, whereas MAT2A shows a wider distribution and is believe to be the responsible for SAM synthesis in extrahepatic tissues. Although MAT2A was predominant gene expressed in skin cells, the detection of significant mRNA levels of MAT1A in normal melanocytes was, therefore, an unexpected finding. More important was the higher levels of MAT2A with respect to MAT1A in cancerous cells. A switch in gene expression from MAT1A to MAT2A has been reported in various human-derived liver cancer cells and hepatoma tissues resected from patients (Cai et al., 1996), and it has been proposed that such altered gene expression might provide a growth advantage to cancerous liver cells (Cai et al., 1998). In any case, the results obtained of the study of methionine cycle gene expression indicated that this cycle is highly active in melanoma cells when compared with normal melanocytes.
Expression of Methylases and Methylation Status in Melanoma Cells COMT is an enzyme which catalyzes the transfer of a methyl group from the methyl donor SAM to the hydroxyl moiety of the catechol ring of a substrate (Mannisto and Kaakkola, 1999). Human COMT protein exists in two different forms. The soluble form (S-COMT) resides in the cytoplasm and possibly also in nuclei, whereas membrane-bound form (MB-COMT) is an integral membrane protein of the rough endoplasmic reticulum (Tenhunen et al., 1999). Due to the importance of this enzyme for melanocyte survival, we decided to analyze the levels and distribution of COMT mRNAs in human melanoma cells and compared with normal melanocytes. Because S-COMT has no unique sequences compared with MB-COMT mRNA a first set of primer was designed from the carboxy terminal region to amplify both the soluble and membrane-bound forms, (S+MB)-COMT. The second set of primers is specific for the amino terminal portion to provide a measurement of only the membrane bound form, MB-COMT.

Figure 25:
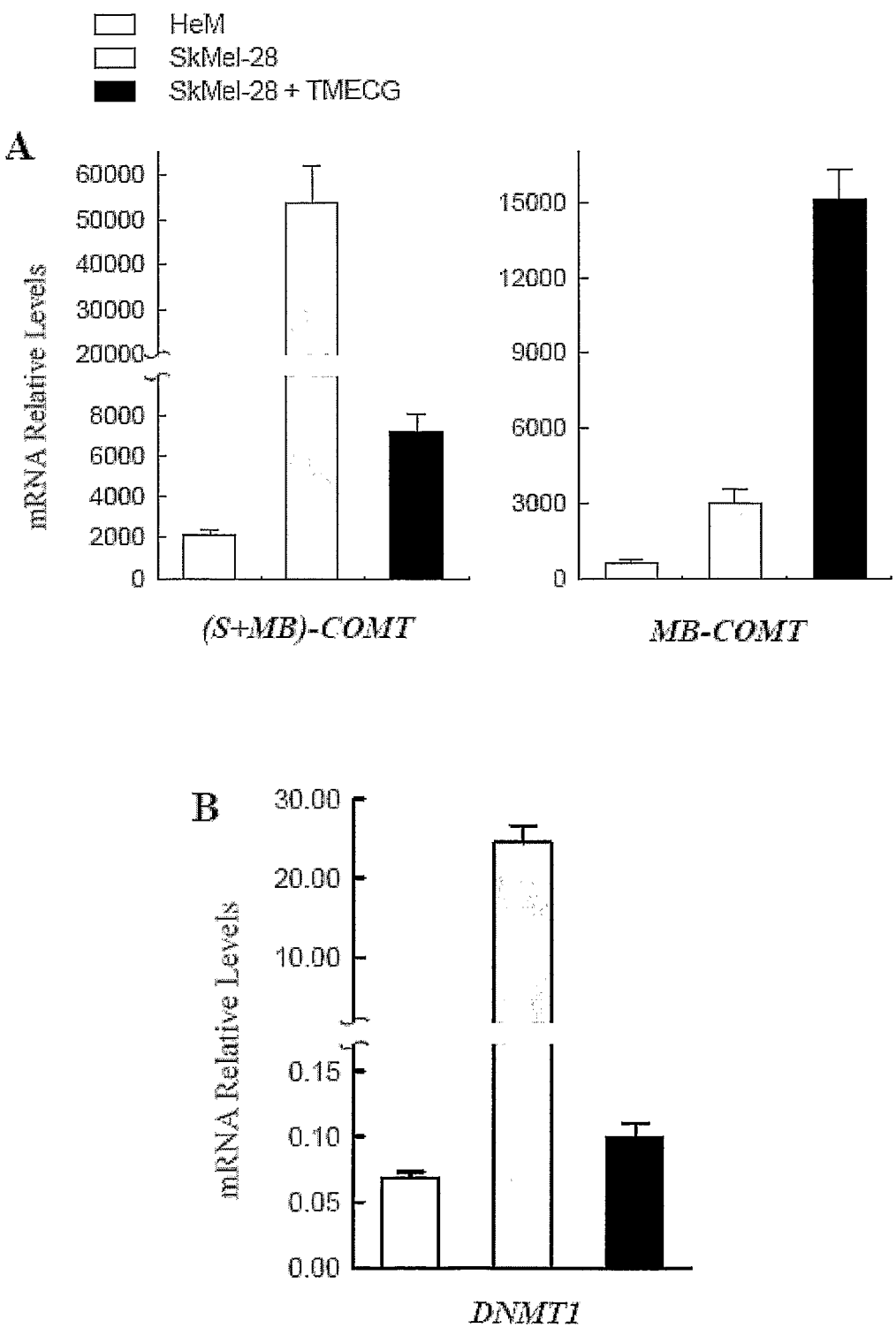
FIG. 25 shows a semi quantitative determination of (A) COMTs and (B) DNMT1 mRNAs. Histograms compare the estimated relative levels of the mRNA with respect to that of β-actin. Values represent the number of copies of mRNA per each $1\times10^6$ copies of β-actin.

FIG. 25 shows that the relative abundance of mRNAs for both COMT isoforms was similar in HeM cells. However, the higher abundance of (S+MB)-COMT compared to MB-COMT mRNA in SkMel-28 provides indication that most of the COMT are of soluble forms in these tumor cells. The high over-expression of S-COMT respect to MB-COMT in melanoma cells could be related to their different mechanisms of regulating their expression.

An indication of the high methylase activity of SkMel-28 was indicated by the high levels of expression of DNMT1 mRNA in these cells, which ranged from 350 to 500-fold higher than in normal melanocytes (FIG. 25). DNA methylation patterns are frequently altered in human cancer, and include genome-wide hypomethylation as well as regional hypermethylation at CpG islands (Jones & Laird, 1999; Widschwendter & Jones, 2002). In mammals, methylation of CpG dinucleotides is mediated by three DNA methyltransferases: DNMT1, DNMT3a, and DNMT3b (Bestor, 2000). DNMT1 has a preference for hemimethylated DNA as a substrate and is considered a maintenance methylase that restores methylation pattern after DNA replication (Li et al., 1992). To investigate whether DNMT1 overexpression is implicated in the overall level of DNA methylation, we study the susceptibility of genomic DNA from SkMel-28 cells to the methylation-sensitive restriction endonuclease Hpa II. The methylation-insensitive isoschizomer Msp I was used as a control. DNA from DNMT1-overexpressing cells (SkMel-28) was highly resistant to digestion with Hpa II, suggesting that DNMT1 mediates aberrant methylation of multiple genes in these tumor cells.
TMECG is an Antifolate that Efficiently Block the Methionine Cycle in Melanoma Cells The effect of TMECG on methionine cycle gene expression was studied. After five days of treatment with 50 μM TMECG the growth of SkMel-28 was significantly inhibited (more than 60%). Cells at this time were collected and the mRNA levels for MS, MAT1A, MAT2A and AHYC were evaluated (FIG. 24). As can be observed the mRNA levels for MS and AHYC were similar to that observed in normal melanocytes and significantly lower than those detected in untreated SkMel-28 cells. However, the level of MAT2A showed a slightly but significant increase with respect to those in SkMel-28, while the level of MAT1A was essentially the some. The data indicated that TMECG-treatment had efficiently blocked the methionine cycle in SkMel-28 cells. In addition to the effects on the methionine cycle the TMECG treatment produced a great effect on the expression of methylases (FIG. 25). DNMT1 recovered normal levels in treated cells and, as a consequence, the overall DNA methylation of the TMECG-treated cells is reduced. TMECG treatment also re-established MB-COMT mRNA levels (FIG. 25), which could be related to unmethylation of its MB promoter (Sasaki et al. 2003).
TMECG Induces Apoptosis in SkMel-28.

Figure 26:
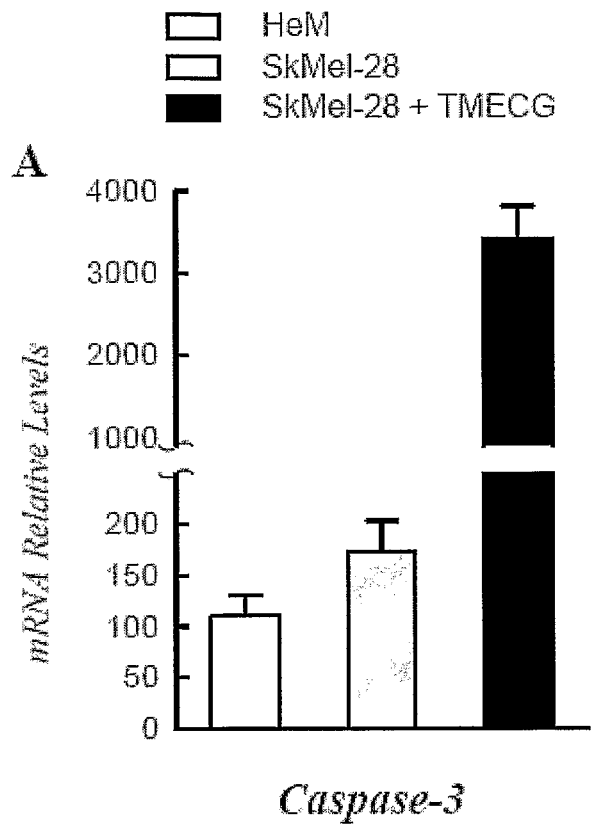
FIG. 26 shows the effect of TMECG on Caspase-3 mRNA expression. Histograms compare the estimated relative levels of the mRNA with respect to that of β-actin. Values represent the number of copies of mRNA per each 1×10⁶ copies of β-actin.

To investigate whether treatment with TMECG induced apoptosis in SkMel-28, cells were treated with 50 μM TMECG for 7 days. DNA fragmentation, which is typical of apoptosis, was visible after treatment. The levels of expression of caspase-3 mRNA and its protein activation, features that indicated apoptotic cell death, were evaluated by real time PCR and activity assays, respectively. Caspase-3 mRNA was estimated around 30-times higher in SkMel-28 TMECG-treated cells than in HeM or untreated Skmel-28 (FIG. 26).

Figure 27:
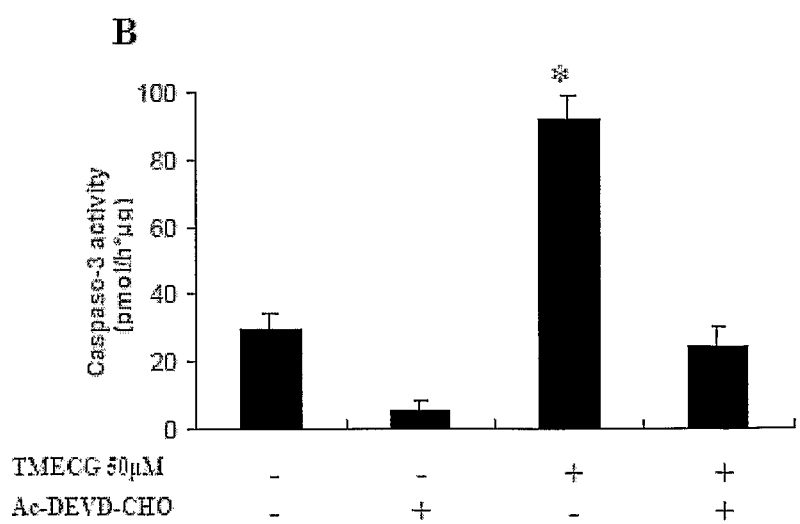
FIG. 27 shows the effect of TMECG on Caspase-3 activity. Cells were treated for 7 days with 50 μM TMECG. Caspase-3 activity was determined in the absence or the presence of Ac-DBVD-CHO. The results are expressed as the mean±SD of three cultures. The data are representative of duplicate activity determinations. *P<0.05, significantly different from non-treated group.

In addition, the cells treated with TMECG showed significantly higher caspase-3 activity, which was specifically inhibited by Ac-DVED-CHO (FIG. 27).

Figure 28:
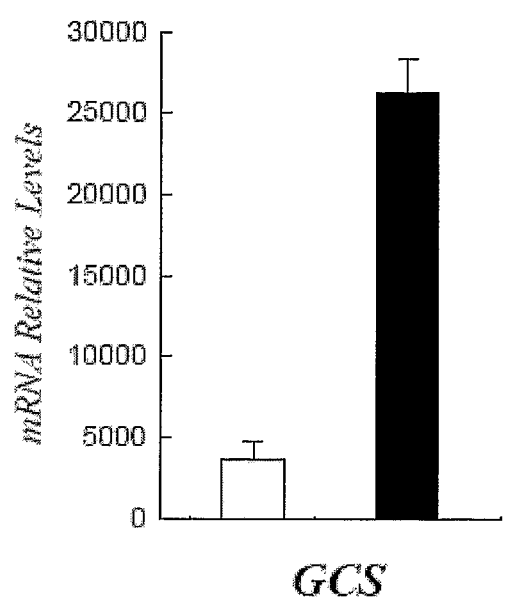
FIG. 28 shows semi-quantitative determination of GCS mRNA before and after TMECG treatment. Histograms compare the estimated relative levels of the mRNA with respect to that of β-actin. Values represent the number of copies of mRNA per each 1×10⁶ copies of β-actin.

All results together indicated the importance of methylation to avoid melanoma cell apoptosis (FIG. 25).
TMECG Activates Glutathione Synthesis in Melanoma Cells Additional confirmation of methionine cycle disruption by TMECG was obtained from an unexpected finding. We noted that SkMel-28 subjected to TMECG treatment experimented and significant cell whitening. To confirm that such effect was associated with the antifolate activity of TMECG, the experiment was carried out in the presence of MTX instead TMECG. MTX produced the same effect on cell whitening. A microscopy study revealed important differences in melanosome melanin content. Untreated SkMel-28 cells showed melanin-full melanosomes, but in cells treated with TMECG or MTX the melanosomes showed a much less melanin content. By analyzing the scheme of FIG. 2, the connection between the folate cycle and the melanin synthesis pathway could be established though the methionine cycle and the synthesis of glutathione. To evaluate the effect of TMECG on glutathione synthesis, we analyzed the levels of γ-glutamylcysteine synthetase (GCS), the rate-limiting enzyme in the biosynthesis of this compound, in Skmel-28 cells. The GCS mRNA ranged from 2600 to 4200 copies per million of copies of β-actin mRNA in untreated SkMel-28 (FIG. 28). Treatment of these cells with TMECG elevated the number of copies of GCS mRNA to a mean value of 26300 (FIG. 28).

The data presented here provides indication that accumulated homocysteine, as a consequence of methionine cycle disruption by TMECG, may serve as a substrate for glutathione synthesis in TMECG-treated cells. This increase of glutathione inhibits melanin synthesis resulting in profound cell whitening. Associated effects of glutathione increase after TMECG treatment are being investigated in our laboratory.
SAM Enhances the Antiproliferative Effects of TMECG Having in mind the effectiveness of TMECG in disrupt the methionine cycle we designed several strategies to block it completely. The first strategy was to inhibit MAT2A enzyme. As described above the expression of MAT2A gene is increased after treatment with TMECG. This observed augmentation could represent a mechanism of cells to escape from TMECG treatment. MAT2A shows a very low Km for methionine (4-10 μM) and in tissues that predominantly express MAT2A the rate of SAM synthesis is near maximal and relatively unaffected by fluctuations in methionine concentration and, therefore, MAT2A can work even a very low concentration of methionine. Another kinetic characteristic of MAT2 is that this enzyme is strongly inhibited by the product of its reaction, SAM, with an IC50 of 60 μM (Sullivan and Hoffman, 1983).

Figure 29:
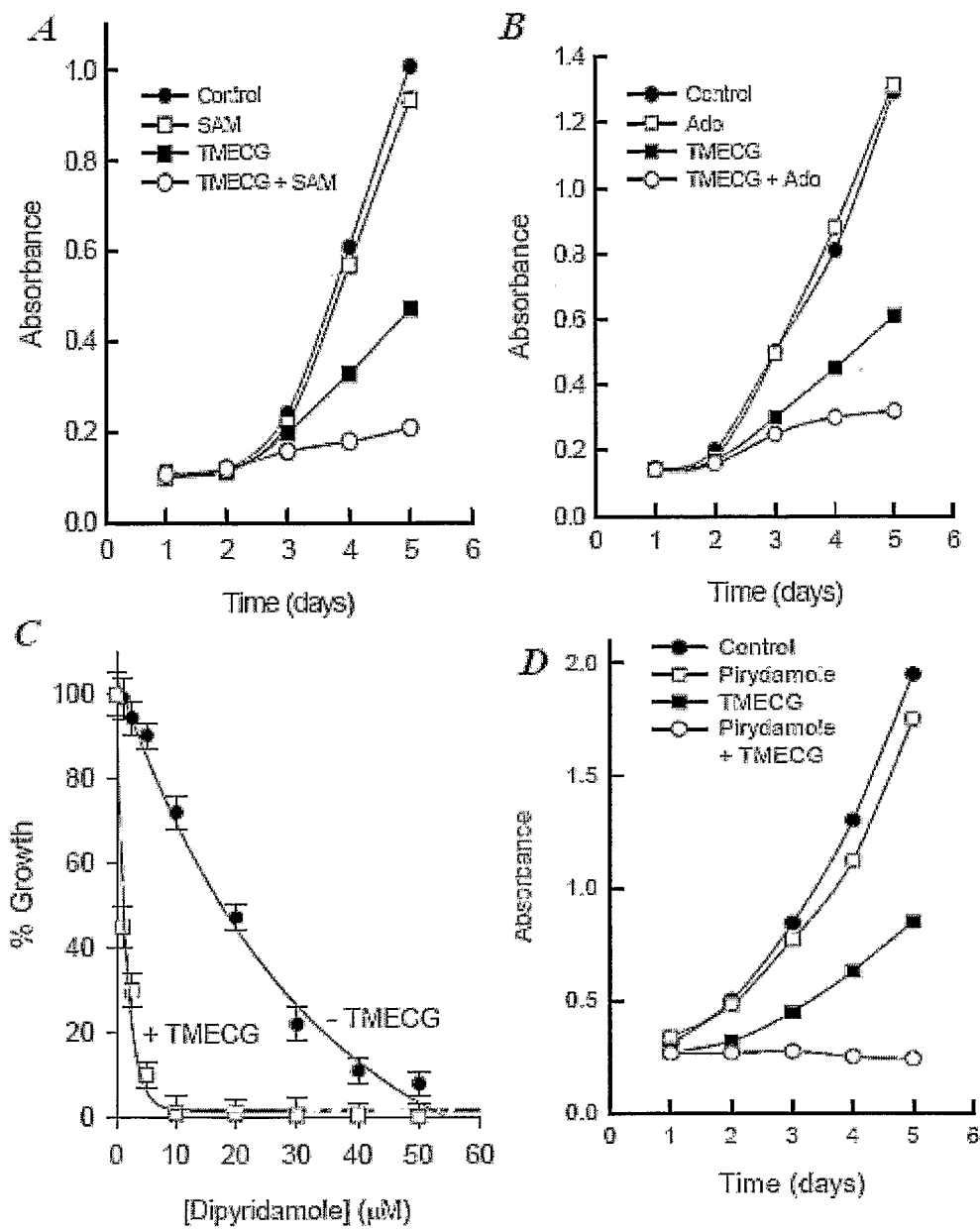
FIG. 29 shows the effects of combinational treatments with TMECG on the growth of SkMel-28 cells. Cell growth was evaluated by a colorimetric assay for mitochondrial function using the MTT cell proliferation assay. For the assay cells were plated in a 96-well plate at a density of 1000 cells/well and grown until they reached 30% confluence. (A) Effect of SAM on cell growth. Cells were treated with vehicle only (control), with SAM (20 μM), with TMECG (50 μM) or with a combination of the same concentration of both SAM plus TMECG. Treatments were done in triplicate and each experiment was done at least twice. (B) Effect of adenosine on cell growth. Cells were treated with vehicle only (control), with adenosine (50 μM), with TMECG (50 μM) or with a combination of the same concentration of both adenosine plus TMECG. (C) Effect of different pirydamole concentrations on SkMel-28 cell growth after 5 days of treatment in the absence (–TMECG series) or the presence (+TMECG series) of 50 μM TMECG. The data was expressed assuming 100% of growth for untreated cells for the series –TMECG or for cells treated with 50 μM TMECG in the series +TMECG. (D) Effect of pirydamole on cell growth. Cells were treated with vehicle only (control), with pirydamole (5 μM), with TMECG (50 μM) or with a combination of the same concentration of both pirydamole +TMECG. Treatments were done five times and each experiment was done at least twice.

We hypothesized that increasing intracellular SAM concentration in the presence of TMECG would block two consecutive steps in the methionine cycle, the synthesis the methionine and the synthesis of SAM (FIG. 2). The effect of adding SAM alone on the growth of SkMel-28 can be visualized in FIG. 29. Only high amount of SAM (up to 100 μM) affected SkMel-28 growth in accordance with its calculated IC50 parameter with MAT2A. However, in the presence of TMECG lower concentrations of SAM showed a synergistic behaviour with this antifolate compound. Thus, the combination 20 μM of SAM and 50 μM of TMECG completely inhibited the growth of SkMel-28 (FIG. 29). The results indicated that when MAT2A is working at limiting concentrations of methionine in the presence of TMECG, it is highly susceptible to inhibition by lower SAM concentrations.

Strategies to Increase the Intracellular Concentration of Adenosine

We hypothesized that accumulation of adenosine in the presence of TMECG may block the methionine cycle at three levels: the synthesis of methionine, the methylase reaction and the synthesis of SAM (FIG. 2).

We increased the extracellular concentration of adenosine. Adenosine alone had not any detectable effect on SkMel-28 growth at the studied concentrations (up to 500 μM). However, in the presence of TMECG adenosine treatment showed a significant synergistic effect, enhancing the antiproliferative action of this antifolate compound. A combination of 50 μM of Adenosine and 50 μM of TMECG completely inhibit the growth of SkMel-28 (FIG. 29).

Adenosine has limited utility as a therapeutic agent as it is rapidly metabolized to inosine and AMP. Therefore, we used other strategies to accumulate adenosine in melanoma cells. Dipyridamole inhibits the cellular reuptake of adenosine by inhibiting ENTs. Moreover, it also inhibits the enzyme ADA which normally breaks down adenosine into inosine. The effect of dipyridamole alone or in combination with TMECG on the growth of SkMel-28 cells is shown in FIG. 29. Dipyridamole alone inhibited SkMel-28 growth with a calculated IC50 (at 5 days) of 20 μM. However, in the presence of 50 μM TMECG the IC50-value dropped to less than 1 μM. The effect of combine 5 μM dipyridamole and 50 μM TMECG can be observed in FIG. 29C. The results indicated the efficacy of this combination treatment against malignant melanoma.

The Combination of TMECG and Dipyridamol in a Primary Tumour Model

As previously observed in SkMel-28 human melanoma cells, the combination of the antifolate, TMECG, with DIPY was highly active on mouse B16/F10 melanoma cells. TMECG and DIPY, at very low concentration, act synergically inducing apoptosis in this cell line. Translational therapy was then designed to probe the efficacy of this combination on mice induced melanoma tumor. Injection of 5×105 B16/F10 melanoma cells in the back of C57/B16 mice formed a blackish tumor mass, which in untreated control mice reached to a tumor area of 3.7±0.7 and 9.3±1.1 cm2 in female and male, respectively, after 21 days of cells inoculation.

Male mice developed larger tumors than females, being this difference significant (p<0.05). This was the first observed gender difference but not the only one. Males and females also differed in the response to the TMECG/DIPY combined therapy.

Figure 30:
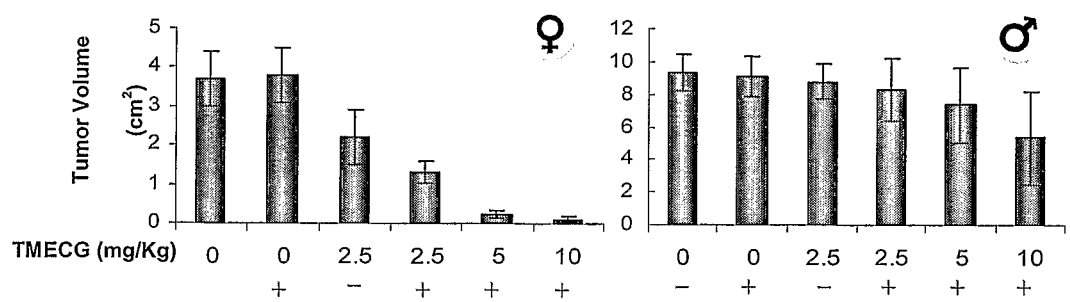
FIG. 30 shows the effect of TMECG/DIPY on the volume of B16/F10 melanoma cell tumours in male and female C57/B16 mice.

As predicted in culture cells experiments, the combination TMECG/DIPY was highly effective in reducing the growth of tumor cells in females, and the synergy between both compounds was also evident. Single treatments with TMECG (2.5 mg/Kg/d) reduced tumor mass in a 27% of the observed in control untreated animals, while treatment with DIPY (10 mg/Kg/d) alone had not visible effects on tumor growth (FIG. 30). However, combination of TMECG/DIPY (2.5/10 mg/Kg/d) reduced tumor masses in more that a 65%, and more efficiency in the treatment was found when the concentration of TMECG was increased in this combination (90% and 95% of tumor mass reduction after treatment with 5/10 and 10/10 mg/Kg/d of TMECG/DIPY, respectively).

In contrast, male mice showed high resistance to the treatments: single treatments with TMECG or DIPY were not effective and the higher tested doses of the combination TMECG/DIPY (10/10 mg/Kg/d) only reduced the tumor mass by a 43% (FIG. 30).

We observed that dihydrotestosterone highly upregulated dihydrofolate reductase (DHFR) expression in melanoma cells and this may be the reason for the resistance to TMECG/DIPY therapy in melanoma cells and also the reason for a higher development of the tumours in males. This upregulation could have important implications for melanoma therapy and provides indication that TMECG may be effective in combination with anti-androgens, especially in male patients.

We have also observed synergy between TMECG and the thymidylate synthase (TS) inhibitor 5-fluorouracil (5-FU) during treatment of melanoma cells.

Toxicity Studies of TMECG and Dipyridamol

Figure 33:
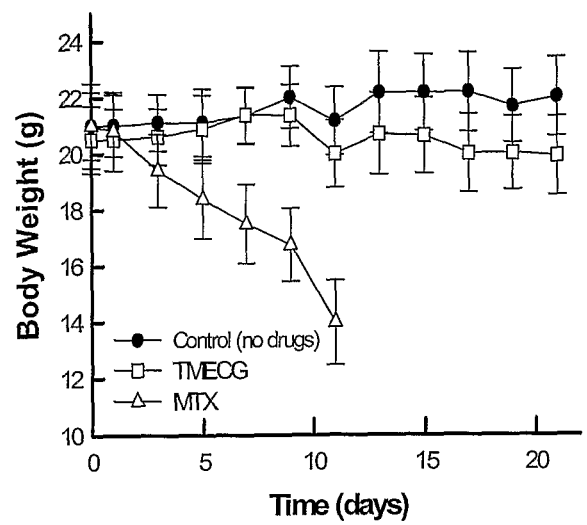
FIG. 33 shows the effect of TMECG/DIPY and MTX on mice body weight. Free tumor female mice (n=10) were subjected to treatments with TMECG/DIPY (10/10 mg/kg/day) or MTX (10 mg/kg/day). At the eleventh day of the treatments, differences in body weight of MTX-treated versus untreated or TMECG-treated groups were statistically significant (p<0.05) and, to avoid unnecessary suffering of the animals, the survivors of the MTX-treated group were sacrificed at this time. Differences between untreated and TMECG-treated groups were not significant during the whole experiment. The graph represents the median of the mice body weight±SD during the treatment.

To explore the toxicity of TMECG/DIPY combination and MTX, these drugs (all at 10 mg/kg/day) were individually administrated intradermally on the back of non-tumor inoculated mice (n=10), and the body weight was monitored every other day. The results are shown in FIG. 33.

Differences between untreated and TMECG/DIPY-treated groups were not found to be significant.

Figure 34:
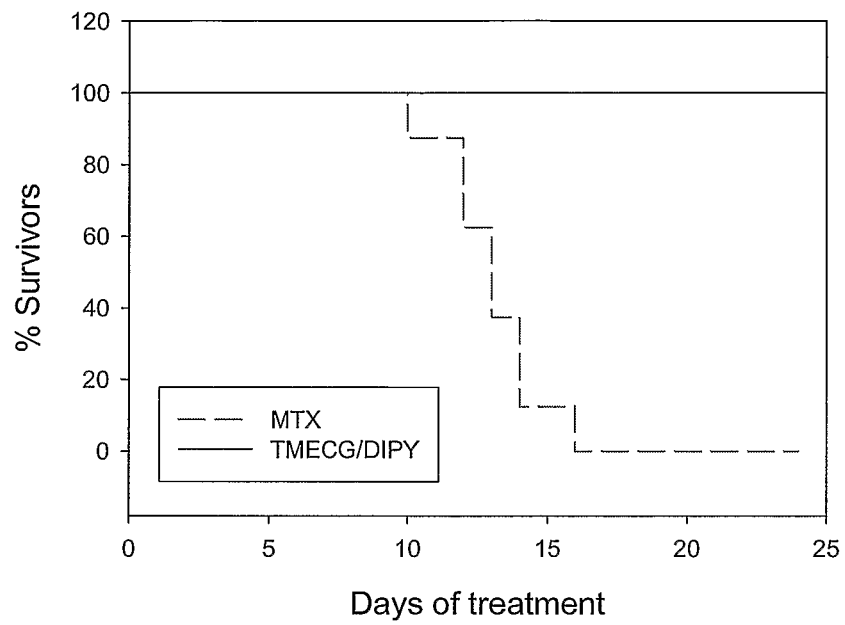
FIG. 34 shows the % survival of tumor free female mice subjected to treatments with TMECG/DIPY (10/10 mg/kg/day) or MTX (10 mg/kg/day) after administration of the drugs. In these experiments to assess survival, mice were killed when they became moribund.

In a further experiment we determined the survival of the animals after administration of the drugs. In these experiments to assess survival, mice were killed when they became moribund. Results are shown in FIG. 34.

TMECG/DIPY treatments were found to be effectively safe for animals. After 21 days, mice had a normal appearance with normal body weight and the level of survival was of 100%.

The Combination of TMECG, Dipyridamol and Anti-Androgens in a Primary Tumour Model A combined therapy using TMECG (10 mg/kg/day), DIPY (10 mg/kg/day) and the antagonists of the androgen receptors flutamide (10 mg/kg/day) was provided to mice (n=14) bearing melanoma B16 tumors injected intradermally in the back.

The combination TMECG/DIPY was injected intradermally on the back, while flutamide (FLU) was intraperitoneally injected the day after of tumour injection. Tumour growth was determined every other day and metastasis at day 31.

Figure 35:
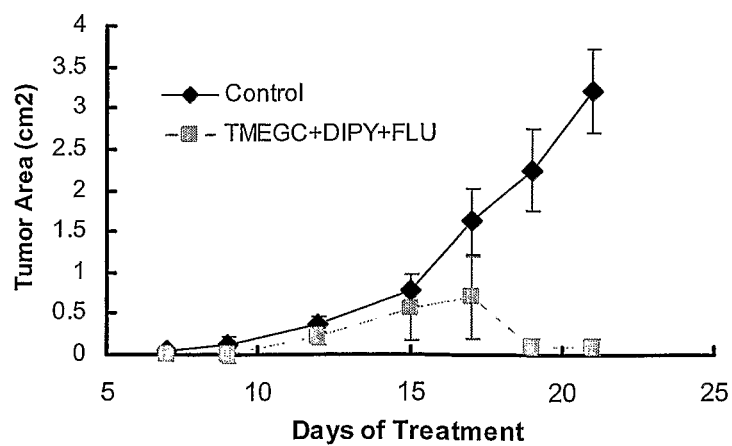
FIG. 35 shows tumor area in mice (n=14) bearing melanoma B16 tumors treated with a combined therapy using TMECG (10 mg/kg/day), DIPY (10 mg/kg/day) and the androgen receptor antagonist flutamide (10 mg/kg/day)

FIG. 35 shows the evolution of the tumors during the treatments. Control group develops prominent tumours with small differences between individuals. The tumors were observed as black-bloody masses with a soft appearance. However, tumors in the treated groups showed a different behaviour from untreated groups. At day 12, the tumors in treated mice were similar to the tumors of untreated mice, but after this day, the tumors became dry and lost the bloody appearance. On the other hand, a great difference was observed between individuals with mice (n=4) developing bigger tumors and the most (n=10) having smaller tumors. The metastasis was evaluated at day 31: 88.8% of untreated animals (eight of 9 survivors at this day) showed visible lung metastasis; however only 16.6% (one of 6 survivors at this day) showed metastasis in treated animals.

Although the triple combination (TMECG/DIPY/FLU) was found to be safe in non-inoculated tumors (the body weight and the general aspect were similar to the found in TMECG/DIPY combinations), seven mice of the treated group became moribund by days 12 and 19, being scarified. Post-mortem analysis of these animals showed no visible metastasis in any body organs, but revealed that the tumors had "exploited" and a hole was present in the place having the primary tumors. The death of these animals was not a consequence of the tumors but was probably due to sepsis following infection by microorganisms.

These results indicated that the combination TMECG/DIPY/FLU is efficient on mice with melanoma tumors, stopping the growth of the tumors and inhibiting their vascularisation or angiogenesis.

Targeting the Pentose Phosphate Pathway with TMECG

We have studied the effects of combinations of TMECG with two inhibitors of the pentose phosphate cycle, dehydroepiabdrosterone (DHEA) and oxythiamine (OT).

The combination of TMECG with OT did not show synergistic activity on melanoma cells. However, a strong synergy was observed between TMECG and DHEA. This indicated that depletion of NADPH by DHEA affected TMECG in a positive manner.

These results indicate that the combination of TMECG or TMECG/DIPY with DHEA may be useful for melanoma treatment.

Effect of TMECG in a Metastasis Model

B16 melanoma cells were injected into the tail vein, allowing microtumours to develop (1 week), then, the animal were treated for 21 days with TMECG (20 mg/Kg/d) plus Dipyridamol (10 mg/Kg/d) by intraperitoneal injection. The animals were sacrifice and lungs and liver analyzed for tumor growth.

Figure 31:
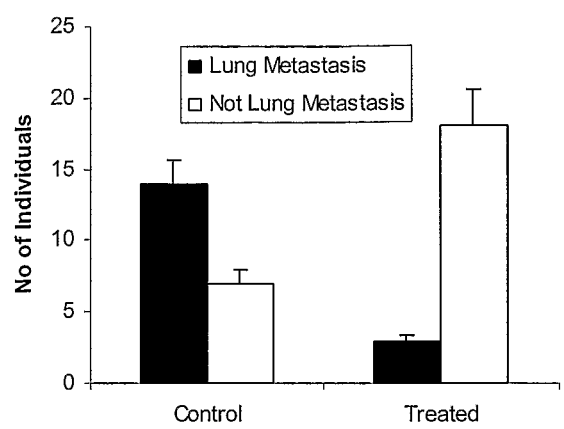
FIG. 31 shows the effect of TMECG/DIPY on the lung metastasis of B16/F10 melanoma cell tumours in male and female C57/B16 mice.

We have now increased the number of treated and control animals (treated 21 female mice compared with 21 control (untreated) females) and the time of treatment (30 days). The results showed a reduction on lung metastasis after intraperitoneal administration of TMECG (FIG. 31).

Effect of 3-O-(3,4,5-Trimethoxybenzoyl)-(−)-Catechin (TMCG) on Breast Cancer

The 4T1 mice breast cancer cell line (ATCC) was used for tumour implantation. This cell line is highly metastatic and after its injection on the back of the Balb/c mice it expanded to the lungs forming metastasis in this organ. Initial experiments were designed for injection in the back to follow tumour growth and lung metastasis.

Figure 32:
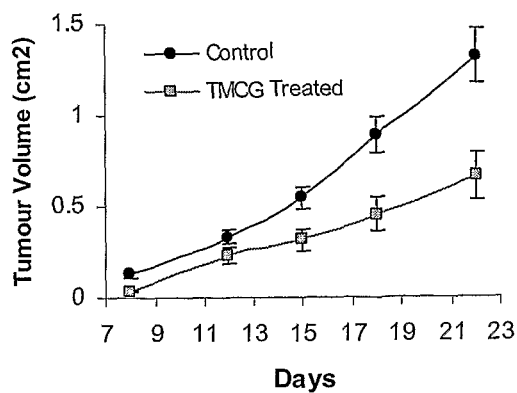
FIG. 32 shows the effect of TMCG (40 mg/Kg/d) on lung tumor volume in Balb/c female mice injected with 4T1 mice breast cancer cell line (ATCC).

We treated 6 Balb/c female mice were treated intraperitoneally with TMCG (40 mg/Kg/d) and compared with 6 untreated (control) mice. When the growth of the tumour was followed with time, we observed a slower growth of metastases in the treated animals, as shown in FIG. 32.

TMECG Is an Antifolate Prodrug

It has been extensively reported that some catechins such as ECG or EGCG inhibit cancer cell proliferation (Jung and Ellis, 2001). To avoid therapeutic problems associated with their poor stability and low cellular uptake, we synthesized a methylated derivative of ECG (TMECG). TMECG was found to be more efficient against melanoma cells. The observation that its effectiveness was directly related with the doubling time in H1264, Caco-2 and MCF7 cells indicated that TMECG may affect their growth by depleting cellular stores of molecules essential for cell survival, particularly in cells that have a faster metabolism, whereas another aspect should be considered when this compound acts on melanoma cells. The expression of tyrosinase, the enzyme responsible for melanin biosynthesis (Rodriguez-López et al., 1992; 1993), is restricted to melanocytes. Therefore, we studied the oxidation of TMECG by this enzyme as a possible explanation of its intracellular activation. Kinetics and spectroscopic data indicated that tyrosinase oxidized TMECG to its corresponding o-quinone, which quickly evolved through a series of chemical reactions to a quinone methide (QM), which showed high stability over a wide pH range. Thus, the data indicated that this highly stable product may be responsible for the observed high activity of TMECG on melanoma cells. Importantly for this work, a series of phenolic compounds, with 4-hydroxyanisole as a representative example, which generated highly stable o-quinones upon oxidation by tyrosinase were identified as potential pro-drugs for the treatment of malignant melanoma (Moridani, 2006).

The action of tyrosinase on TMECG would not only explain why this catechin is activated but also why melanoma cells are essentially resistant to other tea polyphenols such as ECG. Although ECG is also effectively oxidized by tyrosinase, the enzymatically generated product can suffer multiple coupled reactions as a result of the presence of multiple phenolic groups in the ester bonded gallate moiety. These reactions may facilitate its incorporation in melanins, as demonstrated by the stronger pigmentation of the cells treated with ECG, thus preventing the action of ECG.

A mechanism for the activation, cellular distribution and action of TMECG and its products can be now proposed. Competition experiments with sulfasalazine indicated that TMECG does not use the RFC for uptake. This lipophilic drug may passively diffuse across the plasmatic membrane in a manner driven solely by the concentration gradient. Subsequent transport to the melanosome by a concentration gradient would facilitate its tyrosinase-catalyzed oxidation and transformation to the corresponding QM. Because of the low pH of this organelle the predominant form is QMH, which due to its high stability and the absence of formal charge would leave the melanosome and enter the cytosol. The slightly basic pH of the cytosol makes the QM⁻ the predominant form, which is trapped in this compartment due to its formal negative charge. Its concentration increases in this cellular compartment, where it binds to DHFR. As a consequence of DHFR inhibition, intracellular levels of THF coenzymes decrease, resulting in inhibition of TS and consequently DNA biosynthesis, as well as purine synthesis.

TMECG may, therefore, be considered as an anticancer prodrug activated by specific enzyme-catalysis (Rooseboom et al., 2004). The use of a prodrug is a potential strategy to overcome the limitations of chemotherapeutic agents. Prodrugs are compounds that need to be transformed before exhibiting their pharmacological action and are often divided into two groups: (1) those designed to increase the bioavailability to improve the pharmacokinetics of antitumor agents and (2) those designed to deliver antitumor agents locally. The data presented here indicate that TMECG showed both of these characteristics. TMECG is a mild inhibitor of DHFR but highly available to human cells; however, its more active form, QM, is not available at plasma pH. Moreover, intracellular activation of TMECG makes this compound specific for tyrosinase-containing cells. Therapies with TMECG would increase its bioavailability and would archive a high local concentration of the drug. As was indicated in the introductory section, chemoprevention is an ideal strategy for fighting melanoma. Many chemopreventive agents act through the induction of apoptosis as a mechanism for the suppression of carcinogenesis by eliminating genetically damaged cells, initiated cells or cells that have progressed to malignancy. The soft antifolate character of the prodrug (TMECG), its specific activation on melanoma cells and the fact that antifolates are more active on fast-dividing cancer cells make this compound ideal for the prevention and treatment of this skin pathology.

Mechanisms of Folate Transport in Melanocytes and Melanoma Cells

The normal melanocytes used in this study (HeM) co-expressed both FRα and RFC receptors but the abundance of mRNA was substantially greater in the case of FRα than RFC. Assuming this as a normal situation for melanocytes growing in a suitable folate medium, SkMel-28 strongly modifies the expression of its folate transporters, the ratio between FRα and RFC falling from 258 to 7.5. An increase of RFC mRNA and protein levels in SkMel-28 was an expected result for rapidly growing cells that require continuous supplementation of this vitamin. However, the downregulation of FRα in melanoma cells (more than 10-times with respect to normal cells) was an unexpected finding, especially as it has been found to be overexpressed in many malignant tissues of epithelial origin, including the uterus, ovary, breast, and colon (Anthony, 1996). This was the first unexpected finding but not the only one. The alternative splicing of FRα pre-mRNA was observed to maintain two intronic regions in SkMel-28 cells.

Although the existence of several transcript variants for the FRα gene has been extensively reported (Roberts et al., 1997), all these variants differ in the lengths of 5' and 3' UTR, but encode an identical amino acid sequence. Therefore, to our knowledge, this is the first indication of the presence of a transcript encoding for a different size of FRα protein. A schematic representation of the predicted sequence for this folate binding protein (FBP) is depicted in FIG. 18.

TMECG Escapes to Natural Resistance Mechanisms to Antifolates

Human melanomas pose a significant clinical problem since they are resistant to treatment with most chemotherapeutic agents (Kufe et al., 1980). The observation that FRα is not available for folate transport in SkMel-28, together with the rapid cell response in decreasing RFC after folate depletion could explain, in part, the high resistance of melanoma to antifolates. The lack of receptors on the cell surfaces could impede antifolate transport. TMECG does not use folate transporters and may avoid this type of resistance mechanism. The second resistance mechanism is related with antifolate retention. Lack of antifolate polyglutamylation in melanoma cells would maintain a low steady-state concentration of antifolates. In contrast, we obtained no evidence that the active form of TMECG, QM$^-$, needs polyglutamylation. QM$^-$ is trapped in cells due to its negative charge and therefore, the effective concentration of inhibitor should be greater that for antifolates which are dependent on polyglutamylation. Finally, it is now well established that an increase in DHFR activity is a common cause of antifolate resistance. TMECG efficiently down-regulates this enzyme and, therefore, can also escape this resistance mechanism.

In conclusion, we have demonstrated that a synthetic derivative of ECG, TMECG, might be considered as a drug for the treatment of melanoma. TMECG maintains the ability to inhibit DHFR but shows significant and important differences from other classical and non-classical antifolates. TMECG combines the advantages of an anticancer prodrug with the possibility of avoid natural cell resistance mechanisms against antifolates. This compound was seen to be active not only on melanoma cells cultures but was also efficient in animal models, where it inhibited growth and metastasis of preformed tumours.

REFERENCES

Anderson, M. E. (1998) Chem. Biol. Interact., 111-112, 1-14.
Ancans, J. et al. (2001) Exp. Cell Res. 268, 26-35.
Antony, A. C. (1996) Annu. Rev. Nutr. 16, 501-521.
Appleman, J. R. et al. (1988). J. Biol. Chem. 263, 10304-10313.
Barth, A. et al. (1995). J. Am. Coll. Surg. 181, 193-201.
Berman, H. M. et al. (2000) Nucleic Acids Res. 28, 235-242.
Bertocci, B. et al. (1991) PNAS USA, 88, 1416-1420.
Bestor, T. H. (2000) Hum. Mol. Genet., 9, 2395-2402.
Bosson, G. (2003) Br. J. Biomed. Sci. 60, 117-129.
Cai, J. et al. (1996). Hepatology, 24, 1090-1097.
Cai, J. et al. (1998) Cancer Res., 58, 1444-1450.
Capizzi, P. J. et al. (1994). Compr. Ther. 20, 20-23.
Cellarier, E. et al. (2003) Cancer. Treat. Rev., 29, 489-499.
Chattopadhyay, S. et al. (2007). Mol. Cancer. Ther. 6, 404-417.
Chattopadhyay, S. et al. (2006) Mol. Cancer. Ther. 5, 438-449.
Chen, Z. S. et al. (2002) Cancer Res. 62, 3144-3150.
Chudnovsky, Y. et al. (2005) J. Clin. Invest. 115, 813-824.
Cody, V. et al (2004) Acta Crystallogr. D Biol. Crystallogr. 60, 646-655.
Fenoll, L. G. et al. (2000) Eur. J. Biochem. 267, 5865-5878.
Francis, S. O. et al. (2006) J. Am. Acad. Dermatol. 55, 849-861.
Furukawa, Y. et al. (2005) Mol. Cancer. Res., 3, 325-334.
Garcia-Trevijano, E. R. et al. (2000) FASEB J., 14, 2511-2518.
Gaukroger, J. et al. (1983) Br. J. Cancer 47, 671-679.
Hong, J. et al. (2002) Cancer Res. 62, 7241-7246.
Houghon, A. N., and Polsky, D. (2002). Cancer Cell 2, 275-278.
Jansen, G. et al. (2004) Arthritis Rheum. 50, 2130-2139.
Jones P A et al. (1999). Nat. Genet., 21, 163-167.
Jung, Y. D. et al. (2001) Int. J. Exp. Path. 82, 309-316.
Kamen, B. A. et al. (2004) Adv. Drug Deliv. Rev. 56, 1085-1097.
Kelemen, L. E. (2006) Int. J. Cancer 119, 243-250.
Kong, K. H. et al. (2000) Comp. Biochem. Physiol. 125, 563-569.
Koon, H. et al. (2006) N. Engl. J. Med. 354, 758-760.
Kufe, D. W. et al. (1980). J. Invest. Dermatol. 75, 357-359.
Lacey, S. W. et al. (1989) J. Clin. Invest. 84, 715-720.
Li, E. et al. (1992) Cell, 69, 915-926.
Lundstrom, K. et al. (1995) Biochim. Biophys. Acta, 1251: 1-10.
del Marmol, V. et al. (1993) J. Invest. Dermatol., 101, 871-874.
Mannisto, P. T. et al. (1999) Pharmacol. Rev., 51, 593-628.
Matherly, L. H. et al. (2003) Vitam. Horm. 66, 403-456.
Mato, J. M. et al. (1997) Pharmacol. Ther., 73, 265-280.
Maziarz, K. M. et al. (1999) J. Biol. Chem. 274, 11086-11091.
Mena, S. et al. (2007) Clin. Cancer Res., 13, 2658-2666.
Moridani, M. Y. (2006) Cancer Lett. 243, 235-245.
Navarro-Martínez, M. D. et al. (2007) J. Enz. Inhibit. Med. Chem. En prensa.
Navarro-Perán, E., et al. (2005a) Cancer Res. 65, 2059-2064.
Navarro-Perán, E et al. (2005b) Biochemistry 44, 7512-7525.
Navarro-Peran, E. et al. (2007). Int. J. Biochem. Cell Biol., 39, 2215-2225.
Obrador, E. et al. (2002) Hepatology, 35, 74-81.
Pappo, A. et al. (1990) J. Natl. Cancer Inst. 82, 1641-1642.
Park, K. D. et al. (2004) Bioorg. Med. Chem. Lett. 14, 5189-5192.
Pradeep, C. R. et al. (2002) Clin. Exp. Metastasis 19, 703-708.
Roberts, S. J. et al. (1997) Biochem. J. 326, 439-447.
Roberts, S. J. et al. (1998) Arch. Biochem. Biophys. 351, 227-235.
Rodríguez López, J. N. et al. (1993) Biochem. J. 293, 859-866.
Rodríguez López, J. N. et al. (1992) J. Biol. Chem. 267, 3801-3810.
Rooseboom, M. et al. (2004) Pharmacol. Rev. 56, 53-102.
Saikawa, Y. et al. (1993) J. Biol. Chem. 268, 5293-5301.
Sasaki, M. et al. (2003) Cancer Res., 63, 3101-3106.
Smit, N. et al. (1994) Pigment Cell Res., 7, 403-408.
Smith, S. L. et al. (1979) J. Biol. Chem. 254, 11475-11484.
Soengas, M. S. et al. (2001) Nature, 409, 207-211.
Stark, M. et al. (2003) Mol. Pharmacol. 64, 220-227.
Stone, S. R., and Morrison, J. F. (1986) Biochim. Biophys. Acta 869, 275-285.
Sullivan, D. M. et al. (1983) Biochemistry, 22, 1636-1641.
Tabrizchi, R. et al. (2001) Pharmacol. Ther., 91, 133-147.
Tenhunen, J. et al. (1999) Cancer Lett., 144, 75-84.
Theti, D. S. et al. (2004) Clin. Cancer Res. 10, 1080-1089.
Thomas, T. et al. (2001) Cell Mol. Life. Sci., 58, 244-258.
Timbola, A. K. et al. (2006) J. Braz. Chem. Soc. 17, 139-148.
Tse, A. et al. (1998) J. Biol. Chem. 273, 25944-25952.
Tückmantel, W. et al. (1999) J. Am. Chem. Soc. 121, 12073-12081.
Ulmanen, I. et al. (1991) Eur. J. Biochem., 202, 1013-1020.
Wang, X. et al. (1992) Biochem. Pharmacol. 44, 1898-1901.
Weitman, S. D. et al. (1992) Cancer Res. 52, 3396-3401.
Whetstine, J. R. et al. (2002) Biochem. J. 367, 629-640.
Widschwendter, M. et al. (2002) Oncogene, 21, 5462-5482.

Yurkow, E. J. et al. (1989) Arch. Biochem. Biophys. 275, 122-129.

Zhao, R. et al (2003) Oncogene 22, 7431-7457.

SEQUENCES

MAQRMTTQLL LLLVWVAVVG EAQTRIAWAR TELLNVCMNA

KHHKEKPGPE DKLHEQCRPW RKNACCSTNT SQEAHKDVSY

LYRFNWNHCG EMAPACKRHF IQDTCLYECS PNLGPWIQQV

CMASCRYKT

SEQ ID NO:1 (Soluble FR alpha amino acid sequence: sequence identical to membrane bound form is underlined and in italics is represented the amino-terminal sequence eliminated in the mature FRα protein (Lacey et al., 1989)

ATGGCTCAGCGGATGACAACACAGCTGCTGCTCCTTCTAGTGTGGGT

GGCTGTAGTAGGGGAGGCTCAGACAAGGATTGCATGGGCCAGGACTG

AGCTTCTCAATGTCTGCATGAACGCCAAGCACCACAAGGAAAAGCCA

GGCCCCGAGGACAAGTTGCATGAGCAGTGTCGACCCTGGAGGAAGAA

TGCCTGCTGTTCTACCAACACCAGCCAGGAAGCCCATAAGGATGTTT

CCTACCTATATAGATTCAACTGGAACCACTGTGGAGAGATGGCACCT

GCCTGCAAACGGCATTTCATCCAGGACACCTGCCTCTACGAGTGCTC

CCCCAACTTGGGGCCCTGGATCCAGCAGGTATGCATGGCTTCCTGCA

GGTACAAGACCTAGCGGAGCAGCTGAGCTTTCCAGGCATCTCTGCAG

GCTGCAACCCCAGCTCCAGTTCTATTCGGGCTGAGTTGCTGGGATT

CTTGAACCTGAGCCCTTCTTTTGTATCAAAATCACCCAGGTGGATCA

GAGCTGGCGCAAAGAGCGGGTACTGAACGTGCCCCTGTGCAAAGAGG

ACTGTGAGCAATGGTGGGAAGATTGTCGCACCTCCTACACCTGCAAG

AGCAACTGGCACAAGGGCTGGAACTGGACTTCAGGTGAGGGCTGGG

TGGGCAGGAATGGAGGGATTTGGAAGTGGAGGTGTGTGGGTGTGGAA

CAGGTATGTGACAATTTGGAGTTGTAGGGCTGGCAGACCTCAAGATA

GTTCCGGGCCCAGTGGCTAAAGGTGTTCCCTCCTCTCTACAGGGTTT

AACAAGTGCGCAGTGGGAGCTGCCTGCCAACCTTTCCATTTCTACTT

CCCCACACCCACTGTTCTGTGCAATGAAATCTGGACTCACTCCTACA

AGGTCAGCAACTACAGCCGAGGGAGTGGCCGCTGCATCCAGATGTGG

TTCGACCCAGCCCAGGGCAACCCCAATGAGGAGGTGGCGAGGTTCTA

-continued

TGCTGCAGCCATGAGTGGGGCTGGGCCCTGGGCAGCCTGGCCTTTCC

TGCTTAGCCTGGCCCTAATGCTGCTGTGGCTGCTCAGCTGA

Seq ID NO: 2 (Soluble FR alpha nucleotide sequence)

TABLE 1

Inhibition constants for rHDHFR

| Inhibitor | $K_I$ (nM) | $k_{on}$ (M$^{-1}$s$^{-1}$) | $k_{off}$ (s$^{-1}$) | Decrease % further EI reactions (-fold) | $K_I$* (nM) |
|---|---|---|---|---|---|
| EGCG | 920 | $1.3 \times 10^5$ | 0.12 | 28 | 33 |
| ECG | 1780 | $1.7 \times 10^5$ | 0.30 | 19 | 92 |
| TMECG | 2100 | $1.4 \times 10^5$ | 0.29 | 19 | 110 |
| MTX[a] | 0.21 | $4.0 \times 10^8$ | 0.021 | 60 | 0.0035 |
| QM | 8.2 | $5.8 \times 10^4$ | $4.8 \times 10^{-4}$ | 0 | 8.2 |

[a] Data obtained from Appleman et al., 1998

The invention claimed is:

1. A method of treating melanoma comprising administering to an individual in need thereof a therapeutically effective dose of a compound of formula (XI) at neutral pH:

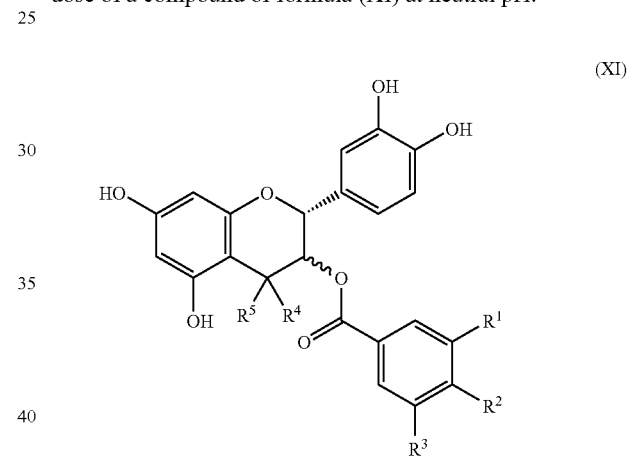

(XI)

wherein:
each —R$^1$, —R$^2$ and —R$^3$ is independently -Q$^1$, —OH or —H, where at least one of —R$^1$, —R$^2$ and —R$^3$ is not a substituent selected from the group consisting of —H and —OH;
each —R$^4$ and —R$^5$ is independently —H;
each -Q$^1$ is independently selected from the group consisting of:
—F, —Cl,
—R$^A$,
—OR$^A$,
—SH, and —SR$^A$,
where each —R$^A$ is independently selected from the group consisting of: methyl and ethyl, each of which may substituted by one or more fluoro or chloro groups;
wherein optionally one or more of the hydroxyl groups in the compound of formula (XI) are esterified to an —O—C(=O)—R$^C$ group, wherein R$^C$ is selected from the group consisting of: methyl and ethyl;
or an isomer, salt or solvate thereof.

2. A method according to claim 1 wherein —R$^1$, —R$^2$, and —R$^3$ are the same.

3. A method according to claim 1 wherein —R$^1$ and —R$^3$ are the same.

4. A method according to claim 1 wherein, each of —R$^2$ and —R$^3$ is independently selected from the group consisting of: —H, —F, —Cl, —Br, —I, and —OR$^A$.

5. A method according to claim 1 wherein each of —$R^1$, —$R^2$ and —$R^3$ is independently —$OR^A$.

6. A method according to claim 1 wherein each —$R^A$ is independently methyl, optionally substituted by one or more fluoro or chloro groups.

7. A method according to claim 1 wherein the compound is of formula (XIa):

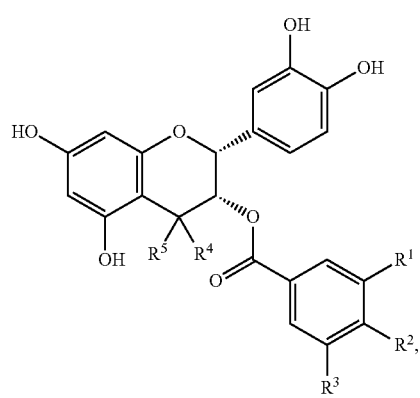

(XIa)

or Formula (XIb):

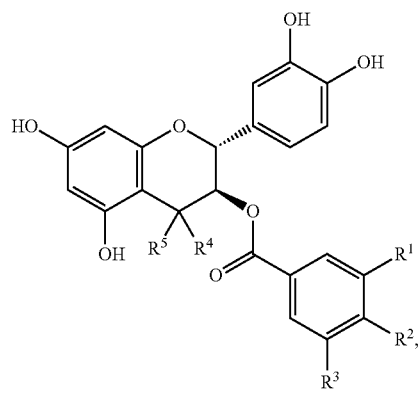

(XIb)

wherein optionally one of more of the hydroxyl groups in the compound of formula (XIa) or formula (XIb) are esterified to an —O—C(=O)—$R^c$ group, where $R^c$ is selected from the group consisting of methyl and ethyl; or an isomer, salt, or solvate thereof.

8. A method according to claim 7 wherein $R^c$ is methyl.

9. A method according to claim 1 wherein the compound of formula (XI) is one of:

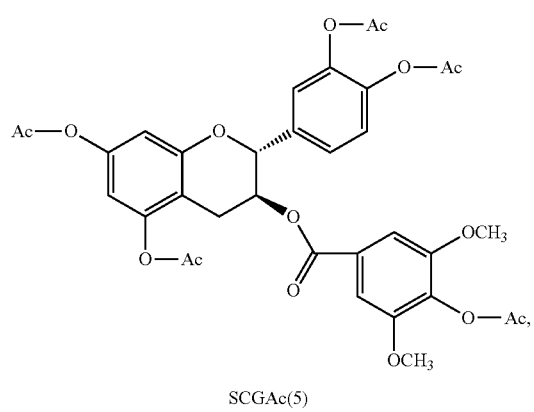

SCGAc(5)

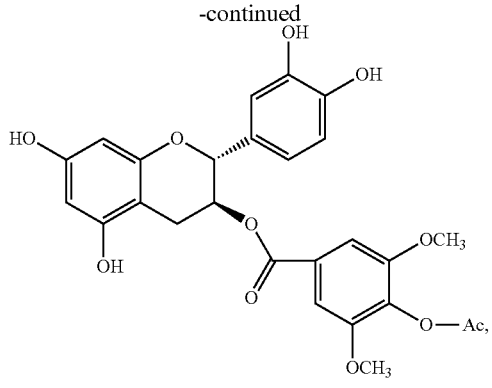

SCGAc(1)

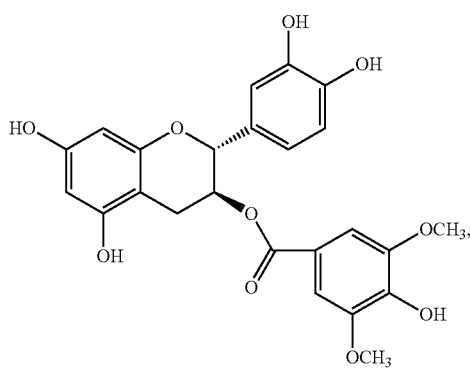

SCG

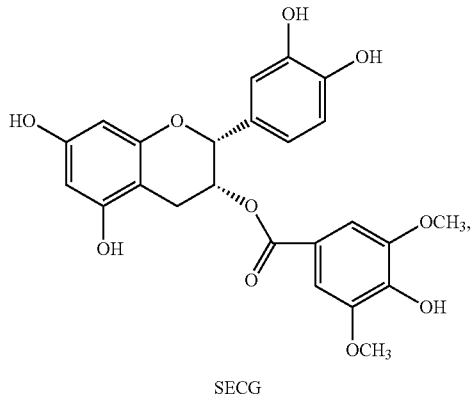

SECG wherein optionally one or more of the hydroxyl groups in the compound are esterified to an —O—C(=O)—$R^C$ group, where $R^C$ is selected from the group consisting of: methyl and ethyl;

or an isomer, salt, or solvate thereof.

10. A method according to claim 1 wherein the compound is 3,4,5-trimethoxy-epicatechin-3-gallate, or an isomer, salt, solvate, chemically protected form thereof.

11. A method according to claim 1 wherein the compound is administered in combination with;

a cytotoxic FRα ligand selected from the group consisting of 2-[4-[2-(4-amino-2-oxo-3,5,7-triazabicyclo[4.3.0] nona-3,8,10-trien-9-yl)ethyl]benzoyl]aminopentanedioic acid, BGC945 and BGC638;

an anti-androgen selected from the group consisting of flutamide, nilutamide, bicalutamide, finasteride and dutasteride;

a methionine cycle inhibitor selected from the group consisting of s-adenosylmethionine, 5'-methylthioadenosine, 5-azacytidine and 5-aza-2'-deoxycytidine, adenosine, dipirydamole, pirydamole and difluoromethylornithine; or, a thymidylate synthase (TS) inhibitor selected from the group consisting of 5-fluorouracil, fluorodeoxyuridine, raltitrexed, and nolatrexed.

* * * * *